US010167323B2

(12) United States Patent
Gao et al.

(10) Patent No.: US 10,167,323 B2
(45) Date of Patent: Jan. 1, 2019

(54) NUCLEIC ACID MOLECULES ENCODING INSECTICIDAL PROTEINS

(71) Applicant: Syngenta Participations AG, Basel (CH)

(72) Inventors: Yan Gao, Research Triangle Park, NC (US); Jared Conville, Research Triangle Park, NC (US); Jeng Shong Chen, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 379 days.

(21) Appl. No.: 14/963,898

(22) Filed: Dec. 9, 2015

(65) Prior Publication Data

US 2016/0201083 A1    Jul. 14, 2016

Related U.S. Application Data

(63) Continuation of application No. 13/499,102, filed as application No. PCT/US2010/050369 on Sep. 27, 2010, now Pat. No. 9,243,262.

(60) Provisional application No. 61/247,986, filed on Oct. 2, 2009.

(51) Int. Cl.
*C07K 14/325* (2006.01)
*C12N 15/82* (2006.01)
*C12N 15/10* (2006.01)

(52) U.S. Cl.
CPC .......... *C07K 14/325* (2013.01); *C12N 15/102* (2013.01); *C12N 15/8286* (2013.01); *Y02A 40/162* (2018.01)

(58) Field of Classification Search
CPC .................................................. C07K 14/325
See application file for complete search history.

(56) References Cited

U.S. PATENT DOCUMENTS

| | | | | |
|---|---|---|---|---|
| 5,530,197 A | * | 6/1996 | Peferoen | A01N 63/02 424/93.2 |
| 5,628,995 A | | 5/1997 | Peferoen et al. | |
| 6,121,521 A | * | 9/2000 | Desai | A01N 63/02 800/320.1 |

FOREIGN PATENT DOCUMENTS

WO    WO2011/041256 A2    4/2011

OTHER PUBLICATIONS

Bohorova et al 2001, Theoretical and Applied Genetics 103: 817-826.*
International Search Report for International Patent Application No. PCT/US2010/050369 dated Jun. 9, 2011.

* cited by examiner

*Primary Examiner* — David H Kruse
(74) *Attorney, Agent, or Firm* — Gregory W. Warren

(57) ABSTRACT

Improved compositions and methods for controlling pests are disclosed. In particular, nucleic acid molecules encoding novel engineered Cry1Ba (eCry1Ba) proteins having improved toxicity to lepidopteran insect pests are provided. By substituting at least one amino acid in domain I of a Cry1Ba protein an engineered Cry1Ba protein having substantially altered insecticidal properties is designed. Further, methods of making and using the ecry1Ba nucleic acid sequences, for example in transgenic plants to express eCry1B proteins to confer protection from insect damage are disclosed.

29 Claims, 6 Drawing Sheets
Specification includes a Sequence Listing.

| Pos | Cry Name | SEQ ID No. | Start | End | Length | Matches | % Identity |
|---|---|---|---|---|---|---|---|
| Ref 1 | Cry1Ba1 | 45 | 1 | 1228 | 1228 aa | | |
| 2 | Cry1Ba2 | 46 | 1 | 1228 | 1228 aa | 1227 | 99 |
| 3 | Cry1Ba3 | 47 | 1 | 1228 | 1228 aa | 1227 | 99 |
| 4 | Cry1Ba4 | 48 | 1 | 1228 | 1228 aa | 1227 | 99 |
| 5 | Cry1Ba5 | 49 | 1 | 1228 | 1228 aa | 1228 | 100 |
| 6 | Cry1Ba6 | 50 | 1 | 1228 | 1228 aa | 1220 | 99 |

```
Cry1Ba1  641  scydleragavusifiutnprriktdvtuynidpvenivactsdefcldekreliekvkyskrledernltrqtpfttsi
Cry1Ba2  641  ................................................................................
Cry1Ba3  641  ................................................................................
Cry1Ba4  641  ................................................................................
Cry1Ba5  641  ................................................................................
Cry1Ba6  641  ................................................................................

Cry1Ba1  721  nkrpdtistnegenitatheqsehqwageenittrecnutefkenyvtipgtfeecyptylyqkiyeseikaytryqlryy
Cry1Ba2  721  ................................................................................
Cry1Ba3  721  ................................................................................
Cry1Ba4  721  ................................................................................
Cry1Ba5  721  ................................................................................
Cry1Ba6  721  .......................................s...................................*..

Cry1Ba1  801  iedsrgtleiyliryriakhetidvpgteslxplsvespigregepntcaphleswpildescdgercsiiusttfeldidv
Cry1Ba2  801  ................................................................................
Cry1Ba3  801  ................................................................................
Cry1Ba4  801  ................................................................................
Cry1Ba5  801  ................................................................................
Cry1Ba6  801  ................................................................................

Cry1Ba1  881  gctdlhenigvwvfkiktgeqhaetgaieffeekpllgnalsrvxraekkwndkrakiqietkryteakescusllyd
Cry1Ba2  881  ................................................................................
Cry1Ba3  881  ................................................................................
Cry1Ba4  881  ................................................................................
Cry1Ba5  881  ................................................................................
Cry1Ba6  881  ................................................................................

Cry1Ba1  961  sqydriqaditnigaihaadklvhrixaayiseigvipgvnaelfewleghlitatslydacavvkngdfnngltcwevkg
Cry1Ba2  961  ................................................................................
Cry1Ba3  961  ................................................................................
Cry1Ba4  961  ................................................................................
Cry1Ba5  961  ................................................................................
Cry1Ba6  961  ................................................................................
```

FIG 1C

| Cry1Ba1 | 1041 | hvdvggnhhrsdlvlpewnasvsqavrvqpqcgyllrvtaykegyqegcvtlbelemntdelkfksressevyptdtqtc |
| Cry1Ba2 | 1041 | ............................................................................ |
| Cry1Ba3 | 1041 | ............................................................................ |
| Cry1Ba4 | 1041 | ............................................................................ |
| Cry1Ba5 | 1041 | ............................................................................ |
| Cry1Ba6 | 1041 | ......................s..................................................... |

| Cry1Ba1 | 1121 | ndytshqgtaqcadacnsrnaqyedaysvdthasvnykptyseetytdvrrdnhceydrgyvnyppvjaqyvtkeleyfp |
| Cry1Ba2 | 1121 | ............................................................................ |
| Cry1Ba3 | 1121 | ............................................................................ |
| Cry1Ba4 | 1121 | ............................................................................ |
| Cry1Ba5 | 1121 | ............................................................................ |
| Cry1Ba6 | 1121 | ............................................................................ |

| Cry1Ba1 | 1201 | etdcvslslgetegxflvdevellises |
| Cry1Ba2 | 1201 | ............................ |
| Cry1Ba3 | 1201 | ............................ |
| Cry1Ba4 | 1201 | ............................ |
| Cry1Ba5 | 1201 | ............................ |
| Cry1Ba6 | 1201 | .................s.......... |

```
CrylBal      545  gpltqxyrigfryastvdfdfivarggttvnsfrfistmaagdelkygnfvrraittpftitqlqdlirtalgqlsgngs
CrylAb3      517  a..s,...vrt,.....talq.ht.ld.rpi.qgn.sa..s,.sn.gs.s.rtvg,.....n.sagssvfti.shvfnsgs.

CrylBal      625  vyidkielipvtatfsasydisraqeavnalfintnprniktdvtdyhidysnivaclsdefcldskreilekvkyskr
CrylAb3      597  .....r...fv.aev,.............k,...e....ss,.gig,..............e...........k..s.....h....

CrylBal      705  isdernilqdipnftalnkqpdfistneqsnftsthqpshgwsgsniticqspdvfksnyvtlpgtfnacyptylyqki
CrylAb3      677  ..............tg...r.l.-----------------------r.,

NUCLEIC ACID MOLECULES ENCODING INSECTICIDAL PROTEINS

CROSS-REFERENCE

This is a divisional of co-pending U.S. patent application Ser. No. 13/499,102, filed on Apr. 10, 2012, which is a national stage application of international application No. PCT/US2010/050369, filed on Sep. 27, 2010 and published as WO2011/041256 on Apr. 7, 2011, which is entitled to the benefit of U.S. Provisional Application No. 61/247,986, filed on Oct. 2, 2009, all of which are incorporated herein by reference in their entirety.

STATEMENT REGARDING ELECTRONIC SUBMISSION OF A SEQUENCE LISTING

A Sequence Listing in ASCII text format, submitted under 37 C.F.R. § 1.821, entitled "72633_US_REG_D_NAT_1_ST25", 170 KB in size, generated on Apr. 22, 2013 and filed via EFS-Web is provided in lieu of a paper copy. This Sequence Listing is hereby incorporated by reference into the specification for its disclosure.

FIELD OF THE INVENTION

The invention relates to the fields of protein engineering, plant molecular biology and pest control. More particularly, the invention relates to novel engineered Cry1Ba proteins and nucleic, acid sequences whose expression results in the engineered Cry1Ba proteins, and methods of making and methods of using the engineered Cry1Ba proteins and corresponding nucleic acid sequences to control insects.

BACKGROUND

*Bacillus thuringiensis* (Bt) Cry proteins also called δ-endotoxins or Cry toxins) are proteins that form a crystalline matrix in *Bacillus* that are known to possess insecticidal activity when ingested by certain insects. Over 180 holotype Cry proteins in 58 families have been identified and named. The various Cry proteins have been classified based upon their spectrum of activity and sequence homology. Prior to 1990, the major classes were defined by their spectrum of activity (Hate and Whitely, 1989, Microbiol. Rev. 53:242-255) but more recently a new nomenclature was developed which systematically classifies the Cry proteins based on amino acid sequence homology rather than insect target specificities (Crickmore et al. 1998. Microbiol. Molec. Biol. Rev. 62:807-813).

Most Cry proteins active against lepidopteran insects are formed in the crystalline matrix as 130-140 kDa protoxins. In lepidopteran insects, the alkaline pH of the gut solubilizes the crystal and then gut proteases process the protoxin to toxic proteins of approximately 60-70 kDa. Processing of the protoxin to toxin has been reported to proceed by removal of both N- and C-terminal amino acids with the exact location of processing being dependent on the specific Cry protein and the specific insect gut fluids involved (Ogiwara et al., 1992. J. Invert. Pathol. 60:121-126). The proteolytic activation of a Cry protoxin can play a significant role in determining its specificity.

The three dimensional structure for several Cry proteins has been elucidated. The Cry3A protein, which is active against coleopteran insects, has three structural domains: the N-terminal domain I, from residues 58-290, consists of 7 alpha-helices, domain II, from residues 291-500, contains three beta-sheets in a so-called Greek key-conformation, and the C-terminal domain III, from residues 501-644, is a beta-sandwich in a so-called jellyroll conformation. The three dimensional structure for the lepidopteran active Cry1Aa toxin has also been solved (Grochulski et al., 1995, J. Mol. Biol. 254:447-464). The Cry1Aa toxin also has three domains: the N-terminal domain I, from residues 33-253, domain II from residues 265-461, and domain III from residues 463-609 with an additional outer strand in one of the β-sheets formed by residues 254-264. If the Cry3A and Cry1Aa structures are projected on other Cry1 sequences, domain I runs from about amino acid residue 28 to 260, domain II from about 260 to 460 and domain III from about 460 to 600. See, Nakamura et al., Agric. Biol. Chem. 54(3): 715-724 (1990); Li et al., Nature 353: 815-821 (1991); Ge et al., J. Biol. Chem. 266(27): 17954-17958 (1991); and Honee et al., Mol. Microbiol. 5(11): 2799-2806 (1991); each of which are incorporated herein by reference. Thus, it is now known that based on amino acid sequence homology, all Bt Cry proteins have a similar three-dimensional structure comprising three domains.

Based on the structure, a hypothesis has been formulated regarding the structure/function relationship of the Cry proteins. It is generally thought that domain I, the most N-terminal domain, is primarily responsible for pore formation in the insect gut membrane (Gazit & Shai, 1993, Appl. Environ. Microbiol. 57:2816-2820), domain II is primarily responsible for interaction with a gut receptor thereby determining toxin specificity (Ge et al., 1991, J. Biol. Chem. 32:3429-3436) and domain III, the most C-terminal domain, is most likely involved with protein stability (Li et at. 1991, supra) as well as having a regulatory impact on ion channel activity (Chen et al., 1993, PNAS 90:9041-9045). Domain III has also been implicated in determining specificity (U.S. Pat. No. 6,204,246, herein incorporated by reference). Swapping domain III between lepidopteran-active toxins, such as by in vivo recombination between the coding regions, can result in changes in specific activity. Binding experiments using such hybrids have shown that domain III is involved in binding to putative receptors of target insects, suggesting that domain III may have some impact on specificity through a role in receptor recognition.

The toxin portions of Bt Cry proteins are also characterized by having five conserved blocks across their amino acid sequence (Hofte & Whiteley, supra). Conserved block 1 (CB1) comprises approximately 29 amino acids. Conserved block 2 (CB2) comprises approximately 67 amino acids. Conserved block 3 (CB3) comprises approximately 48 amino acids. Conserved block 4 (CB4) comprises approximately 10 amino acids. Conserved block 5 (CB5) comprises approximately 12 amino acids. The sequences before and after these five conserved blocks are highly variable and thus are designated the "variable regions," V1-V6. Domain I of a Bt Cry protein typically comprises a C-terminal portion of variable region 1, a complete conserved block 1, an entire variable region 2, and the N-terminal 52 amino acids of conserved block 2. Domain II typically comprises approximately the C-terminal 15 amino acids of conserved block 2, a variable region 3, and approximately the N-terminal 10 amino acids of conserved block 3. Domain III typically comprises approximately the C-terminal 38 amino acids of conserved block 3, variable region 4, conserved block 4, variable region 5, and conserved block 5. The Cry1 lepidopteran active toxins, among other Cry proteins, have a variable region 6 with approximately 1-3 amino acids lying within domain III.

Several Cry proteins, for example Cry1Ab, Cry1Ac, Cry1F and Cry2Ba have been expressed in transgenic crop plants and exploited commercially to control certain lepidopteran insect pests. For example, transgenic corn hybrids expressing a Cry1Ab protein have been available commercially for over 10 years. The Cry1Ab protein in these corn hybrids targets primarily European corn borer (*Ostrinia nubilalis*), the major lepidopteran pest in the US Corn Belt.

One concern raised regarding the deployment of transgenic crops expressing a Cry protein is whether insect pests will become resistant to the Cry protein. Insects have proven capable of developing resistance to Cry protein-containing products. Resistance in diamondback moth (*Plutella xylostella*) and other vegetable pests to commercial Bt microbial sprays, used extensively in organic farming, has developed in several parts of the world. One recent incidence of field resistance in a fall armyworm (*Spodoptera frugiperda*) population exposed to transgenic corn expressing Cry1F protein has been documented on the island of Puerto Rico (Storer et al. 2010. J. Econ. Entomol. 103:1031-1038). However, there have been no cases of any field failures in the United States associated with resistant field populations of corn or cotton pests exposed to transgenic crops since 1996 when transgenic crops expressing Cry proteins were first introduced.

The seed industry, university researchers and the US Environmental Protection Agency have worked together to develop management plans to help mitigate the onset of insect resistance. They are based primarily on a high dose and refuge strategy. A high dose strategy for European corn borer in corn, for example, is to use corn hybrids that express high enough levels of as Cry protein to kill even partially resistant European corn borers. The underlying hypothesis is that killing partially resistant ECB and preventing their mating greatly delays the development of resistance. The success of a high dose strategy depends in part on the specific activity of the Cry toxin to European corn borer and how much of that Cry toxin can be expressed in the transgenic corn plant. For example, the higher the specific activity of a Cry toxin to a pest, the less amount of Cry toxin is required to be expressed in a transgenic plant to achieve a high dose strategy. Because Cry1Ab is very toxic to European corn borer larvae (i.e. high specific activity) levels of expression of Cry1Ab that are achievable in transgenic plants easily places such corn hybrids in a high dose category.

Other possible ways to mitigate resistance development include pyramiding multiple Cry proteins in the same transgenic crop plant or replacing existing mature products with new products that produce different Cry proteins. For example, as the current Cry1Ab corn hybrid market matures, new products may be introduced that have Cry proteins other than Cry1Ab or other Cry proteins in addition to Cry1Ab. It would be beneficial for proteins that replace Cry1Ab to have the same or similar specific activity to European corn borer as Cry1Ab.

One candidate Cry toxin to replace Cry1Ab may be a Cry1Ba toxin. The holotype Cry1Ba toxin was first described by Brizzard et al. in 1988 (Nuc. Acids Res. 16:2723-2724). Subsequently, five other Cry1Ba toxins have been identified with each having about 99% identity to the holotype toxin. Cry1Ba toxins have been reported to have activity against certain lepidopteran pests, such as cabbage butterfly (*Pieris brassicae*), diamondback moth (*Plutella xylostella*), Egyptian cotton leafworm (*Spodoptera litioralis*), beet armyworm (*Spadoptera exigua*) and European corn borer (*Ostrinia nubilalis*). However, Cry1Ba has been reported to be greater than 2-fold less active against European corn borer than Cry1Ab (See for example, U.S. Pat. No. 5,628,995) and has been reported to have no activity against other major corn pests, for example corn earworm (*Helicoverpa zea*) (See for example, Karim et al. 2000. Pestic. Biochem. Physiol. 67: 198-216) and NAFTA populations of fall armyworm (*Spodoptera frugiperda*) (See for example, Monnerat et al. 2006. Appl. Environ. Microbiol. 72:7029-7035). One reason that Cry1Ba is not as active as Cry1Ab against at least European corn borer may be due to its lower solubility properties. Thus, there is a need to improve the specific activity of Cry1Ba against at least European corn borer and possibly expand its spectrum of activity to increase its potential as a replacement for Cry1Ab in transgenic corn.

The spectrum of insecticidal activity of an individual Cry toxin from Bt may be quite narrow, with a given Cry toxin being active against only a few species within an Order. For instance, the Cry3A protein is known to be very toxic to the Colorado potato beetle, *Leptinotarsa decemlineata*, but has very little or no toxicity to related beetles in the genus *Diabrotica* (Johnson et al., 1993, J. Econ. Entomol. 86:330-333). In addition, small variations in amino acid sequence within a Cry protein class can impact insecticidal activity. For example, von Tersch et al. (1991, Appl. Environ. Microbiol. 57:349-358) demonstrated that Cry1Ac proteins varying by seven amino acids showed significant differences in their spectrum of insecticidal activity. Although considered primarily lepidopteran-active toxins, Cry1Ba toxins have also been reported to be active against certain coleopteran insects pests including Colorado potato beetle (*Leptinotarsa decemlineata*), cottonwood leaf beetle (*Chrysomela scripta*) and coffee berry borer (*Hypothenemus hampei*).

Specificity of the Cry proteins is the result of the efficiency of the various steps involved in producing an active toxin protein and its subsequent interaction with the epithelial cells in the insect mid-gut. To be insecticidal, most known Cry proteins must first be ingested by the insect and proteolytically activated to form an active toxin. Activation of the insecticidal crystal proteins is a multi-step process. After ingestion, the crystals must first be solubilized in the insect gut. Once solubilized, the Cry proteins are activated by specific proteolytic cleavages. The proteases in the insect gut can play a role in specificity by determining where the Cry protein is processed. Once the Cry protein has been solubilized and processed it binds to specific receptors on the surface of the insects mid-gut epithelium and subsequently integrates into the lipid bilayer of the brush border membrane. Ion channels then form disrupting the normal function of the midgut eventually leading to the death of the insect. There are stark differences in the solubility properties of the toxin portions of Cry proteins.

Certain lepidopteran-active Cry proteins have been engineered in attempts to improve specific activity or to broaden the spectrum of insecticidal activity. For example, the silk moth (*Bombyx mori*) specificity domain from Cry1Aa was moved to Cry1Ac, thus imparting a new insecticidal activity to the resulting chimeric protein (Ge et al. 1989, PNAS 86: 4037-4041). Also, Bosch et al. 1998 (U.S. Pat. No. 5,736, 131), created a new lepidopteran-active toxin by substituting domain III of Cry1E with domain III of Cry1C thus producing a Cry1E-Cry1C hybrid toxin with a broader spectrum of lepidopteran activity.

There remains a need to design new and effective pest control agents that provide an economic benefit to farmers and that are environmentally acceptable. Needed are proteins with substantially altered properties, such as the engineered Cry1Ba proteins of the invention, that have greater specific activity than native Cry1Ba proteins against at least European corn borer, a major pest of corn in the United States, that may become resistant to existing insect control agents. Furthermore, engineered Cry1Ba proteins whose use minimizes the burden on the environment, as through transgenic plants, are desirable.

By increasing the specific activity of Cry1Ba to at least European corn borer, less Cry1Ba protein should be needed to be expressed in a maize plant therefore reducing the possible negative impacts of Cry1Ba on the plant. In addition, the increased specific-activity allows for use of the engineered Cry1Ba in a high dose strategy for ECB.

SUMMARY

In view of these needs, it is an object of the invention to provide novel engineered Cry1Ba (eCry1Ba) proteins having substantially altered properties that are improved over and distinct from native Cry1Ba proteins, particularly biochemical properties associated with the insecticidal activity to lepidopteran pests of corn, including but not limited to such pests as European corn borer (ECB; *Ostrinia nubilalis*), corn earworm (CEW; *Heltcoverpa zea*), southwestern corn borer (SWCB; *Diatraea grandiosella*), sugarcane borer (SCB; *Diatraea saccharalis*), soybean looper (SBL; *Pseudoplusia includens*), velvet bean caterpillar (VBC; *Anticarsia gemmatalis*), and the like. By substituting amino acids at key identified positions in a native Cry1Ba protein sequence or wild-type Cry1Ba protein as defined herein, in accordance with the present invention, an eCry1Ba protein having substantially altered solubility and/or insecticidal properties compared to native Cry1Ba is designed. The invention is further drawn to nucleic acid sequences encoding the eCry1Ba proteins, and to compositions and formulations containing the eCry1Ba proteins, which are capable of inhibiting the ability of insect pests to survive, grow and reproduce, or of limiting insect-related damage or loss to crop plants. The invention is further drawn to a method of making the eCry1Ba proteins and to methods of using the eCry1Ba proteins, for example in transgenic plants to confer protection from insect damage. The substantially altered properties of the eCry1Ba proteins of the invention allow for their use in a high dose strategy against at least ECB while requiring expression levels in corn plants that are readily achievable.

The novel eCry1Ba proteins described herein are highly active against insects. For example, the eCry1Ba proteins of the invention can be used to improve control of economically important insect pests such as ECB or CEW without negatively impacting activity against other important corn pests such as SWCB and SCB. The eCry1Ba proteins of the invention can be used singly or in combination with other insect control strategies to confer maximal pest control efficiency with minimal environmental impact. Transgenic plants expressing the eCry1Ba proteins of the invention provide a means by which growers can control major lepidopteran pests of crops, for example without limitation corn and sugar cane.

According to one aspect, the present invention includes an engineered Cry1Ba (eCry1Ba) protein comprising as mutation at one or more amino acid positions in domain I, whereby the engineered Cry1Ba protein has improved solubility and/or insecticidal activity against at least European corn borer (*Ostrinia nubilalis*) when compared to a native or wild-type Cry1Ba protein.

In another aspect, the mutation at one or more amino acid positions is located in alpha-helix 4 or alpha-helix 5 of domain I.

In a further aspect, the mutation is at an amino acid position corresponding to position 150, 178, 189 or 199 of SEQ ID NO: 2.

In yet another aspect, the mutation is at position 150, 178, 189 or 199 of SEQ ID NO: 5.

In another aspect, the mutation is at a position corresponding to amino acids 2 and 150; or amino acids 2, 150 and 178; or amino acids 2, 150 and 189; or amino acids 2, 150 and 199, of SEQ ID NO: 5.

In still another aspect, the mutation is at amino acids 2 and 150; or amino acids 2, 150 and 178; or amino acids 2, 150 and 189; or amino acids 2, 150 and 199, of SEQ ID NO: 5.

In one aspect, the invention includes an engineered Cry1Ba (eCry1Ba) protein comprising the amino acid sequence of SEQ ID NO: 6, wherein X at position 2 is an amino acid and a) X at position 150 is Pro, Phe, Trp or Lys, and X at position 189 is Leu and at position 199 is Ser; or b) X at position 189 is Ser when X at position 150 is Lys; or c) X at position 199 is Lys when X at position 150 is Lys.

In another aspect, the eCry1Ba protein of the invention comprises the amino acid sequence of SEQ ID NO: 7, SEQ ID NO: 8, SEQ ID NO: 9 or SEQ ID NO: 10.

In yet another aspect, an eCry1Ba protein of the invention has activity against lepidopteran or coleopteran insects, particularly lepidopteran insects. Examples of such lepidopteran insects include but are not limited to European corn borer, southwestern corn borer, sugarcane borer, corn earworm, soybean looper and velvet bean caterpillar.

The invention also includes other variant Cry1Ba proteins (vCry1Ba) wherein a tyrosine (Tyr) or histidine (His) at position 150 (Y150 or H150) is substituted with an amino acid other than Tyr or His. In one aspect, the amino acid that is substituted for Y150 or H150 is Lys, Phe, Trp, Pro, Thr, Len, Ala, Val, Ser, Arg, Gly or Asp.

In another aspect, the invention includes a vCry1Ba protein that comprises SEQ ID NO: 3.

In still another aspect, the invention includes a vCry1Ba protein wherein a Tyr or His at position 150 is substituted with an amino acid other than Tyr or His and also has a valine (Val) at position 81 (V81) substituted with an amino acid other than Val; or an alanine (Ala) at position 155 (A155) and a methionine (Met) at position 178 (M178) substituted with amino acids other than Ala or Met, respectively. In another aspect, the Val at position 81 (V81) is substituted with a tryptophan (Trp) (V81W). In yet another aspect, a variant Cry1Ba protein of the invention comprises SEQ ID NO: 11.

In one aspect, the invention includes a vCry1Ba protein with the Y150 substituted with any other amino acid and, wherein an Ala at position 155 (A155) is substituted with an aspartic acid (Asp) (A155D) and a Met at position 78 (Met178) is substituted with a serine (Ser) (M178S). In another aspect, a variant Cry1Ba protein of the invention comprises SEQ ID NO: 12.

The vCry1Ba proteins of the invention have insecticidal activity against lepidopteran or coleopteran insects, particularly lepidopteran insects. Such lepidopteran insects include without limitation European corn borer, southwestern corn borer, sugarcane borer, corn earworm, soybean looper and velvet bean caterpillar. However, such vCry1Ba proteins may not have increased activity compared to the wild-type Cry1Ba protein against such pests.

In another aspect, the present invention includes a nucleic acid that encodes an engineered Cry1Ba (eCry1Ba) protein of the invention or a variant Cry1Ba protein (vCry1Ba) of the invention.

The present invention also includes a chimeric gene comprising a heterologous promoter sequence operatively linked to a nucleic acid that encodes an eCry1Ba protein or a vCry1Ba protein. The present invention also includes a recombinant vector comprising such a chimeric gene. Further, the present invention includes a transgenic non-human host cell comprising such a chimeric gene. A transgenic host cell according to this aspect of the invention includes without limitation a bacterial cell or a plant cell. Such a transgenic plant cell may be a maize cell or a sugar cane cell.

The present invention further provides a transgenic plant comprising such a plant cell. The eCry1Ba proteins or vCry1Ba proteins are useful for expressing in any transgenic plant when susceptible insect pests are a problem. In another aspect of the invention, progeny plants comprising a nucleic acid of the invention from any generation of a transgenic plant and a propagule comprising a nucleic acid of the invention from any generation of a transgenic plant are included. In another aspect, the transgenic plant is a maize plant or a sugar cane plant. In yet another aspect, the propagule is a seed, a sette or a cutting.

The invention also includes an insecticidal composition comprising an effective insect-controlling amount of an eCry1Ba protein or a vCry1Ba protein according to the invention and additionally an acceptable agricultural carrier. Such agricultural carriers may be, for example, a sprayable formulation or a transgenic plant.

In another aspect, the present invention provides a method of producing a eCry1Ba protein or a vCry1Ba protein that is active against insects, comprising: (a) obtaining a host cell comprising a chimeric gene, which itself comprises a heterologous promoter sequence operatively linked to a nucleic acid of the invention; and (b) expressing the nucleic acid in the transgenic host cell, which results in at least one protein that is active against insects.

In a further aspect, the present invention provides a method of producing an insect-resistant transgenic plant, comprising introducing a nucleic acid of the invention into a plant thereby producing a transgenic plant, wherein the nucleic acid causes the expression of a eCry1Ba protein or a vCry1Ba protein in the transgenic plant in an effective amount to control insects. In yet another aspect, the insects are lepidopteran or coleopteran insects. Such lepidopteran insects include without limitation European corn borer, southwestern corn borer, sugarcane borer, corn earworm, soybean looper and velvet bean caterpillar.

In another aspect, the invention includes a method of making an engineered Cry1Ba (eCry1Ba) protein comprising a) identifying a Cry1Ba protein having a domain I; b) substituting at least one native amino acid at a location in domain I with at least one other amino acid; and c) obtaining the eCry1Ba protein so produced, wherein the eCry1Ba has improved solubility and/or insecticidal activity against at least European corn borer when compared to a native Cry1Ba protein or a wild-type Cry1Ba. In still another aspect, the native amino acid is located in alpha-helix 4 or alpha-helix 5 of domain I.

In still another aspect, the invention includes a method of controlling a lepidopteran insect comprising contacting the insect with an effective amount of an eCry1Ba protein or a vCry1Ba protein of the invention. According to another aspect, such lepidopteran insects include without limitation European corn borer, southwestern corn borer, sugarcane borer, corn earworm, soybean looper and velvet bean caterpillar.

Preferably, the eCry1Ba protein or vCry1Ba protein is delivered to the insects orally. In one aspect, the proteins are delivered orally through a transgenic plant comprising a nucleic acid sequence that expresses a eCry1Ba or vCry1Ba protein of the invention.

The present invention further provides a method of controlling insects wherein a transgenic plant comprising a nucleic acid encoding an eCry1Ba protein or vCry1Ba protein further comprises a second nucleic acid sequence or multiple nucleic acid sequences that encode at least one other pesticidal principle. In one aspect, the second nucleic acid sequence encodes a Cry protein different then the eCry1Ba or vCry1Ba proteins of the invention, those that encode a Vegetative Insecticidal Protein, such as those disclosed in U.S. Pat. Nos. 5,849,870 and 5,877,012, which are incorporated herein by reference, or those that encode a pathway for the production of a non-proteinaceous pesticidal principle. In another aspect of the invention, the second insecticidal principle is a Vip3 protein.

Yet another aspect of the invention is the provision of a method of providing a grower with an improved means of controlling European corn borer, southwestern corn borer, sugarcane borer, corn earworm, soybean looper and velvet bean caterpillar comprising supplying or selling to the grower transgenic propagules comprising a nucleic acid that encodes an eCry1Ba protein having a mutation at one or more amino acid positions in domain I, the eCry1Ba protein having improved solubility or insecticidal activity against at least European corn borer when compared to a native Cry1Ba protein in another aspect, the transgenic propagules are seeds, settes or cuttings.

Other aspects and advantages of the present invention will become apparent to those skilled in the art from a study of the following description of the invention and non-limiting examples.

BRIEF DESCRIPTION OF THE FIGURES

FIGS. 1A, 1B, 1C and 1D shows an alignment of the amino acid sequences of the known native Cry1Ba proteins (SEQ ID NOs:45-50). Amino acids at position 150 are in bold.

FIGS. 2A and 2B shows an alignment of the amino acid sequences of the native full-length Cry1Ab (SEQ ID NO:51) and Cry1Ba (SEQ ID NO:2). Domains I and II and alpha-helices 4 & 5 of Domain I are shown by arrows.

BRIEF DESCRIPTION OF THE SEQUENCES IN THE SEQUENCE LISTING

SEQ ID NO: 1 is a native full-length cry1Ba coding sequence.

SEQ ID NO: 2 is the amino acid sequence of a native full-length Cry1Ba protein.

SEQ ID NO: 3 is a mutated full-length Cry1Ba.

SEQ ID NO: 4 is the cry1Ba-T25 coding sequence.

SEQ ID NO: 5 is the Cry1Ba-T25 wild-type protein.

SEQ ID NO: 6 is the eCry1Ba-X150 protein.

SEQ ID NO: 7 is the eCry1Ba-T2AY150K protein.

SEQ ID NO: 8 is the eCry1Ba-T2AY150KM178S protein.

SEQ ID NO: 9 is the eCry1Ba-T2AY150KL189S protein.

SEQ ID NO: 10 is the eCry1Ba-T2AY150KS199K protein.

SEQ ID NO: 11 is variant Cry1Ba-TM21.
SEQ ID NO: 12 is variant Cry1Ba-TM90.
SEQ ID NO: 13 is a maize-optimized nucleic acid sequence flooding eCry1Ba-T2AY150KL189S protein.
SEQ ID NOs:14-41 are primers useful in the invention.
SEQ ID NO: 42 is a truncated native Cry1Ba.
SEQ ID NO: 43 is variant Cry1Ba-TM69.
SEQ ID NO: 44 is variant Cry1Ba-TM61.
SEQ ID NOs: 45-51 are Cry toxins shown in FIGS. 1 and 2.

Definitions

For clarity, certain terms used in the specification are defined and presented as follows:

"Activity" of an eCry1Ba protein of the invention is meant that the eCry1Ba proteins function as orally active insect control agents, have a toxic effect, or are able to disrupt or deter insect feeding, which may or may not cause death of the insect. When a eCry1Ba protein of the invention is delivered to the insect, the result is typically death of the insect, or the insect does not feed upon the source that makes the eCry1Ba protein available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulatory DNA sequence will affect the expression level of the coding or structural DNA sequence.

A "chimeric gene" or "chimeric construct" is a recombinant nucleic acid sequence in which a promoter or regulatory nucleic acid sequence is operatively linked to, or associated with, a nucleic acid sequence that codes for an mRNA or which is expressed as a protein, such that the regulatory nucleic acid sequence is able to regulate transcription or expression of the associated nucleic acid coding sequence. The regulatory nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

As used herein, the term "corn" means Zea mays or maize and includes all plant varieties that can be bred with corn, including wild maize species.

"Corresponding to" in the context of the present invention means that when the amino acid sequences of Cry1B proteins are aligned with each other, the amino acids that "correspond to" certain enumerated positions in the present invention are those that align with these positions in the native Cry1Ba toxin (SEQ ID NO: 2), but that are not necessarily in these exact numerical positions relative to the particular Cry1Ba amino acid sequence of the invention. For example, the methionine at position 1 of a truncated Cry1Ba protein (SEQ ID NO: 42) will align with the methionine at position 22 of the full-length Cry1Ba (SEQ ID NO: 2).

Therefore, according to the present invention, amino acid 129 of SEQ ID NO: 42 "corresponds to" amino acid number 150 of SEQ ID NO: 2.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Effective insect-controlling amount" means that concentration of toxin that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

An "engineered Cry1Ba" (eCry1Ba) protein of the invention, refers to a Cry1Ba-derived protein having at least one mutation in domain I which is not known to naturally occur in a Cry1Ba protein. An eCry1Ba protein is not naturally occurring and, by the hand of man, comprises an amino acid sequence that is not identical to a protein known to occur in *Bacillus thuringiensis*. Cry1Ba proteins that have been engineered according to the invention have substantially altered and improved properties compared to native Cry1Ba proteins. Particularly, eCry1Ba proteins of the invention have improved solubility and/or insecticidal activity against at least European corn borer compared to a native Cry1Ba, wild-type Cry1Ba or variant Cry1Ba proteins of the invention.

An "engineered cry1Ba gene" (ecry1Ba) according to this invention, refers to a nucleic acid comprising the coding sequence of an eCry1B protein. The engineered cry1Ba gene can be derived from a native cry1Ba gene or from a synthetic cry1Ba gene.

"Expression cassette" as used herein means a nucleic acid sequence capable of directing expression of a particular nucleic acid sequence in an appropriate host cell, comprising a promoter operably linked to the nucleic acid sequence of interest which is operably linked to termination signals. It also typically comprises sequences required for proper translation of the nucleic acid sequence. The expression cassette comprising the nucleic acid sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleic acid sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

As used herein, the term "grower" means a person or entity that is engaged in agriculture, raising living organisms, such as crop plants, for food or raw materials.

A "gut protease" is a protease naturally found in the digestive tract of an insect. This protease is usually involved in the digestion of ingested proteins.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

An "isolated" nucleic acid molecule or protein is a nucleic acid molecule or protein that, by the hand of man, exists apart from its native environment and is therefore not a product of nature. An isolated nucleic acid molecule or protein may exist in a purified form or may exist in a non-native environment such as, for example, a recombinant host cell. For example, a native Cry protein naturally occurring in *Bacillus thuringiensis* is not isolated, but that same Cry protein in a transgenic *Bacillus thuringiensis* strain or a transgenic plant is isolated.

A "native" Cry1Ba protein as used herein, refers to an approximately 140 kDa *Bacillus thuringiensis* (Bt) coleopteran- or lepidopteran-active protein, for example SEQ ID NO: 2, as well as any truncated lower molecular weight protein derivable from a native Cry1Ba protein that has an amino acid sequence found in nature. The lower molecular weight protein can be obtained by protease cleavage of naturally occurring protease recognition sites of the native Cry1Ba protein or by a second translational initiation codon in the same frame as the translational initiation codon coding for the native Cry1Ba protein, for example M22 of SEQ ID NO: 2. The amino acid sequence of a native Cry1Ba protein and the lower molecular weight proteins derived thereof may be found in a protein naturally occurring in Bt. For example, six native Cry1Ba proteins have been named and have the following Genbank accession numbers, Cry1Ba1=CAA29898 (SEQ ID NO:45); Cry1Ba2=CAA65003 (SEQ ID NO:46); Cry1Ba3=AAK63251 (SEQ ID NO:47); Cry1Ba4=AAK51084 (SEQ ID NO:48); Cry1Ba5=ABO20894 (SEQ ID NO:49); Cry1Ba6=ABL60921 (SEQ ID NO:50). A sequence alignment of six native Cry1Ba proteins is shown in FIG. 1. A native Cry1Ba protein can be encoded by a native Bt nucleotide sequence as in SEQ ID NO: 1 or by a synthetic codon optimized nucleotide sequence.

A "nucleic acid molecule" or "nucleic acid sequence" is a linear segment of single- or double-stranded DNA or RNA that can be isolated from any source. In the context of the present invention, the nucleic acid molecule or nucleic acid sequence is preferably a segment of DNA.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, settes, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase and initiates transcription of the DNA. The promoter region may also include other elements that act as regulators of gene expression.

A "propagule" is any plant material used for the purpose of plant propagation. For example, without limitation, seeds, and cuttings or settes are propagules of corn and sugar cane, respectively.

A "protoplast" is an isolated plant cell without a cell wall or with only parts of the cell wall.

"Regulatory elements" refer to sequences involved in controlling the expression of a nucleic acid sequence. Regulatory elements comprise a promoter operably linked to the nucleic acid sequence of interest and termination signals. They also typically encompass sequences required for proper translation of the nucleic acid sequence.

As used herein, "specific activity" refers to the amount of protein required to have an insecticidal effect. Therefore, when a first protein has a higher specific activity than a second protein means that it takes a lesser amount of the first protein compared the second protein to have an insecticidal effect on the same percentage of insects.

"Solubility" as used herein refers to the quantity of a native Cry1Ba toxin, wild-type Cry1Ba or eCry1Ba toxin or vCry1Ba toxin that can dissolve in a particular liquid, for example a buffer, water or insect gut fluid, under the same environmental conditions. Thus, as used herein, an eCry1Ba toxin has "improved solubility" or an "increase in solubility" compared to a native or wild-type Cry1Ba toxin means that a given volume of liquid can hold a great quantity of an eCry1Ba toxin than a native or wild-type Cry1Ba toxin under the same conditions. According to this invention, native Cry1Ba and wild-type Cry1Ba toxins have low solubility and certain eCry1Ba toxins have high solubility, relative to each other.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

A "variant Cry1Ba (vCry1Ba)" protein is a non-native mutant protein that has lower specific activity to at least European corn borer compared to a wild-type Cry1Ba protein of the invention.

A "wild-type Cry1Ba" protein is a non-native mutated protein that has similar insecticidal properties, such as specific activity, against such insects as southwestern corn borer, sugarcane borer or European corn borer, or biochemical properties, such as solubility, as a native Cry1Ba.

Nucleic acids are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Len; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

DETAILED DESCRIPTION

This invention relates to novel engineered Cry1Ba (eCry1Ba) proteins having substantially altered properties improved over and distinct from native Cry1Ba proteins, particularly biochemical properties associated with the insecticidal activity to lepidopteran pests of corn, including but not limited European corn borer (ECB; *Ostrinia nubilalis*), corn earworm (CEW; *Helicoverpa zea*), southwestern corn borer (SWCB; *Diatraea grandiosella*), sugarcane borer (SCB; *Diatraea saccharalis*), soybean looper (SBL; *Pseudoplusia includens*), velvet bean caterpillar (VBC; *Anticarsia gemmatalis*), and the like. By mutating amino acids at key identified positions in a native Cry1Ba protein sequence, in accordance with the present invention, an eCry1Ba protein having substantially altered solubility and/or insecticidal properties compared to a native Cry1Ba or a wild-type Cry1Ba as defined herein is designed. Nucleic acid sequences that encode the eCry1Ba proteins can be used, for example, in transgenic crop plants to cause the expression of the eCry1Ba proteins to control insect pests such as European corn borer (ECB; *Ostrinia nubilalis*), corn earworm (CEW; *Helicoverpa zea*), southwestern corn borer (SWCB; *Diatraea grandiosella*), sugarcane borer (SCB; *Diatraea saccharalis*), soybean looper (SBL; *Pseudoplusia includens*), velvet bean caterpillar (VBC; *Anticarsia gemmatalis*), and the like.

In one embodiment, the present invention encompasses an engineered Cry1Ba (eCry1Ba) protein comprising a mutation at one or more amino acid positions in domain I, whereby the eCry1Ba protein has improved solubility and/or insecticidal activity against at least European corn borer when compared to a native or wild-type Cry1Ba protein.

In another embodiment, the mutation at one or more amino acid positions is located in alpha-helix 4 or alpha-helix 5 of domain I. Studies of the structure-function relationship of certain Cry proteins, such as Cry1Aa, Cry1Ab, and Cry1Ac, have included mutagenesis of alpha-helices 4 and 5 of Domain I (Saraswathy et al. 2004, Electron. J. Biotech. 7: 178-188). Results of these experiments implicate alpha-helix 4 and 5 in ion channel formation and conductance. It is not clear whether any one mutation or a combination of mutations in Domain I of a Cry protein, particularly Cry1Ba would have an impact on solubility and specific activity. Therefore, Domain I of a Cry1Ba protein, particularly at locations in alpha-helix 4 or 5, was targeted for mutational analysis to determine if the solubility could be improved and/or the specific activity of a native Cry1Ba protein could be increased against a target insect, including European corn borer (ECB), southwestern corn borer (SWCB), sugarcane borer (SCB), corn earworm (CEW), soybean looper (SBL) and velvet bean caterpillar (VBC), as well as others. Based on sequence alignment, alpha-helix 4 of Cry1Ba comprises amino acids 143-163 of SEQ ID NO: 2Alpha-helix 5 makes up a majority of Conserved Block 1 and comprises amino acids 176-199 of SEQ ID NO: 2. The six known native Cry1Ba proteins vary by only one amino acid in alpha-helix 4 at position 150. Four of the six have a tyrosine (Tyr; Y) at position 150 and the other two have a histidine (His; H) at position 150. The instant disclosure now demonstrates that the amino acid at position 150 plays a critical role in the toxicity of a Cry1Ba protein and that mutations in alpha-helix 4 and alpha-helix 5 can have a significant impact on protein solubility, specific activity against a particular pest and increase in spectrum of activity of Cry1Ba.

In another embodiment, the invention encompasses mutations at an amino acid position corresponding to position 150, 178, 189 or 199 of SEQ ID NO: 2. In yet another embodiment, the mutation is at position 150, 178, 189 or 199 of SEQ ID NO: 5.

In still another embodiment, the invention encompasses mutations in Cry1Ba at a position corresponding to amino acids 2 and 150; or amino acids 2, 150 and 178; or amino acids 2, 150 and 189; or amino acids 2, 150 and 199, of SEQ ID NO: 5. In another embodiment, the mutation is at amino acids 2 and 150; or amino acids 2, 150 and 178; or amino acids 2, 150 and 189; or amino acids 2, 150 and 199, of SEQ ID NO: 5.

In one embodiment, the invention encompasses an engineered Cry1Ba (eCry1Ba) protein comprising the amino acid sequence of SEQ ID NO: 6, wherein Xaa at position 2 is any amino acid and a) Xaa at position 150 is Pro, Phe, Trp or Lys, and Xaa at position 189 is Leu and at position 199 is Ser; or b) Xaa at position 189 is Ser when Xaa at position 150 is Lys; or c) Xaa at position 199 is Lys when Xaa at position 150 is Lys.

In another embodiment, the invention encompasses an eCry1Ba protein that comprises the amino acid sequence of SEQ ID NO: 7, SEQ ID NO: 8, SEQ ID NO: 9 or SEQ ID NO: 10.

In yet another embodiment, an eCry1Ba protein of the invention has activity against lepidopteran or coleopteran insects, particularly against lepidopteran insects. Examples of such lepidopteran insects include but are not limited to European corn borer, southwestern corn borer, sugarcane borer, corn earworm, soybean looper and velvet bean caterpillar. Engineered Cry1Ba proteins of the invention also have activity against corn earworm, an insect pest for which native Cry1Ba is not active.

In still another embodiment, the invention encompasses an eCry1Ba protein that has at least a 3× higher specific activity than a native Cry1Ba protein against at least European corn borer.

In another embodiment, the invention also encompasses variant Cry1Ba (vCry1Ba) proteins wherein a tyrosine (Tyr) or histidine (His) at position 150 (Y150 or H150) is substituted with an amino acid other than Tyr or His. In one aspect, the amino acid that is substituted for Y150 or H150 is Lys, Phe, Trp, Pro, Thr, Leu, Ala, Val, Ser, Arg, Gly or Asp.

In another embodiment, the invention encompasses a mutated Cry1Ba protein that comprises SEQ ID NO: 3.

In still another embodiment, the invention encompasses a vCry1Ba protein wherein a Tyr or His at position 150 (Y150 or H150) is substituted with an amino acid other than Tyr or His and also has a valine (Val) at position 81 (V81) substituted with an amino acid other than Val; or an alanine (Ala) at position 155 (A155) and a methionine (Met) at position 178 (M178) substituted with amino acids other than Ala or Met, respectively. In another embodiment, the Val at position 81 (V81) is substituted with a tryptophan (Trp) (V81W). In yet another embodiment, the invention encompasses a variant Cry1Ba protein that comprises SEQ ID NO: 11.

In one embodiment, the invention encompasses a vCry1Ba protein with the Tyr at 150 (Y150) substituted with any other amino acid and, wherein an Ala at position 155 (A155) is substituted with an aspartic acid (Asp) (A155D) and a Met at position 178 (M178) is substituted with a serine (Ser) (M178S). In another embodiment, the invention encompasses a vCry1Ba protein comprising SEQ ID NO: 12.

The vCry1Ba proteins encompassed by the invention have insecticidal activity against a lepidopteran or coleopteran insect. Such a lepidopteran insect includes without limitation European corn borer, southwestern corn borer, sugarcane borer, corn earworm, soybean looper and velvet bean caterpillar. The activity of vCry1Ba proteins is typically less than a wild-type Cry1Ba protein of the invention. One advantage of such variant Cry1Ba proteins is their usefulness in situations where high specific activity is not required. The skilled person will recognize other uses and advantages of such variant Cry1Ba proteins.

The insect controlling properties of the eCry1Ba proteins and vCry1Ba proteins of the invention are further illustrated in Examples 2, 4, 5, 6 and 9.

In one embodiment, the present invention encompasses a nucleic acid that encodes an eCry1Ba protein of the invention or encodes a vCry1Ba protein of the invention. In another embodiment, the nucleic acid comprises SEQ ID NO: 13.

The invention also encompasses a chimeric gene comprising a heterologous promoter sequence operatively linked to a nucleic acid that encodes an eCry1Ba protein or vCry1Ba protein. In one embodiment, the heterologous promoter is selected from the group consisting of maize ubiquitin, cestrum virus (cmp), corn TrpA, rice actin, bacteriophage T3 gene 9 5' UTR, maize metallothionein (mtl), corn sucrose synthetase 1, corn alcohol dehydrogenase 1, corn light harvesting complex, corn heat shock protein, pea small subunit RuBP carboxylase, Ti plasmid opine synthase, Ti plaid nopaline synthase, petunia chalcone isomerase, bean glycine rich protein 1, Potato patatin, lectin, CaMV 35S, and the S-E9 small subunit RuBP carboxylase promoter The present invention also encompasses recombinant vectors comprising the nucleic acid sequences of this invention. Such vectors include, without limitation, a plasmid, cosmid, phagemid, artificial chromosome, phage or viral vector. In such vectors, the nucleic acid sequences are preferably comprised in expression cassettes comprising regulatory elements for expression of the nucleic acid sequences in a host cell capable of expressing the nucleic acid sequences. Such regulatory elements usually comprise promoter and termination signals and preferably also comprise elements allowing efficient translation of polypeptides encoded by the nucleic acid sequences of the invention. Vectors comprising the nucleic acid sequences are usually capable of replication in particular host cells, preferably as extrachromosomal molecules, and are therefore used to amplify the nucleic acid sequences of the invention in the host cells. In one embodiment, host cells for such vectors are microorganisms, such as bacteria, including without limitation *E. coli, Bacillus thuringiensis, Bacillus subtilis, Bacillus megaterium, Bacillus cereus, Agrobacterium* or *Pseudomonas*. In another embodiment, host cells for such recombinant vectors are endophytes or epiphytes. In another embodiment, the host cell for such vectors is a eukaryotic cell, such as a plant cell. Examples of such plant cells encompassed by the invention include, without limitation, sorghum, wheat, sunflower, tomato, potato, cole crop, cotton, rice, soybean, sugar beet, sugarcane, tobacco, barley, oilseed rape or a corn cells.

In another embodiment, such vectors are viral vectors and are used for replication of the nucleic acid sequences in particular host cells, e.g., insect cells or plant cells. Recombinant vectors are also used for transformation of the nucleic acid sequences of the invention into host cells, whereby the nucleic acid sequences are stably integrated into the DNA of such host cells, in one embodiment, such host cells are prokaryotic cells. In another embodiment, such host cells are eukaryotic cells, such as plant cells. In another embodiment, the plant cells are corn cells.

In one embodiment, the invention encompasses transgenic plants comprising a nucleic acid of the invention that encodes an eCry1Ba protein or vCry1Ba protein according to the invention. The eCry1Ba proteins or vCry1Ba proteins are useful for expressing in any transgenic plant where susceptible insect pests are a problem. Such transgenic plants include, without limitation, monocotyledonous plants and dicotyledous plants. In one embodiment, the monocotyledonous plants include corn, wheat, oat, rice, barley, sugar cane, sorghum, turf grass, and pasture grass plants. In another embodiment, the dicotyledonous plants include soybean and other legumes, cotton, sunflower, cole crops and other vegetables, sugar beet, tobacco and oilseed rape.

In another embodiment, the invention encompasses a progeny plant from any generation of a transgenic plant, wherein the progeny comprises a nucleic acid of the invention.

In yet another embodiment, the invention encompasses a propagule from any generation of a transgenic plant, wherein the propagule comprises a nucleic acid of the invention. In still another embodiment, the propagule of the invention is selected from the group consisting of a seed, a sette and a cutting.

In another embodiment, the invention encompasses a biological sample from a transgenic plant of the invention, wherein the biological sample comprises an eCry1Ba protein of the invention and the eCry1Ba protein is capable of controlling insect pests. Examples of such biological samples include without limitation any bi-product of corn that comprises protein such as corn meal or corn flour comprising the eCry1Ba protein, where the eCry1Ba protein continues to perform the insecticidal function it had in the transgenic corn plant from which the biological sample was derived.

The invention also encompasses an insecticidal composition comprising an eCry1B protein or vCry1Ba according to the invention and an acceptable agricultural carrier. In one embodiment, the agricultural carrier may be a liquid, a powder, or a transgenic plant, for example without limitation a corn plant or a sugar cane plant.

In another embodiment, the invention encompasses a method of producing an eCry1B protein or a vCry1Ba protein that is active against insects, comprising: (a) obtaining a host cell comprising a chimeric gene, which itself comprises a heterologous promoter sequence operatively linked, to a nucleic acid of the invention; and (b) expressing the nucleic acid in the transgenic host cell, which results in at least one protein of the invention that is active against insects. In another embodiment, the insects are lepidopteran insects or coleopteran insects. In yet another embodiment, the lepidopteran insects are selected from the group consisting of European corn borer, southwestern corn borer, sugarcane borer, corn earworm, soybean looper and velvet bean caterpillar.

In a further embodiment, the invention encompasses a method of producing an insect-resistant transgenic plant, comprising introducing an expression cassette comprising a nucleic acid of the invention into a plant thereby producing a transgenic plant, wherein the expression cassette causes the expression of a protein of the invention in an amount that makes the plant resistant to insects. In another embodiment, the insects are lepidopteran or coleopteran insects. Such lepidopteran insects encompassed by the invention include without limitation European corn borer, southwestern corn borer, sugarcane borer, corn earworm, soybean looper and velvet bean caterpillar.

In another embodiment, the invention encompasses a method of making an eCry1Ba protein comprising a) identifying a Cry1Ba protein having a domain I; b) substituting at least one native amino acid at a location in domain I with at least one other amino acid; and c) obtaining the eCry1Ba protein so produced, wherein the eCry1Ba has improved solubility and/or insecticidal activity against at least European corn borer when compared to a native Cry1Ba protein. In another embodiment, the Cry1Ba protein is Cry1Ba1 having GenBank accession number CA A29898, Cry1Ba2 (CAA65003), Cry1Ba3 (AAK63251), Cry1Ba4 (AAK51084), Cry1Ba5 (ABO20894) or Cry1Ba6 (ABL60921). In still another embodiment, the native amino acid in Cry1Ba is located in alpha-helix 4 or alpha-helix 5 of domain I. In still another embodiment the amino acid is at a position corresponding to position 150, 178, 189 or 199 of SEQ ID NO: 2. In yet another embodiment, the amino acid is at position 150, 178, 189 or 199 of SEQ ID NO: 5. In still another embodiment, the amino acid in Cry1Ba is at a position corresponding to amino acids 2 and 150; or amino acids 2, 150 and 178; or amino acids 2, 150 and 189; or amino acids 2, 150 and 199, of SEQ ID NO: 5. In another embodiment, the amino acid is at positions 2 and 150; or positions 2, 150 and 178; or at positions 2, 150 and 189; or at positions 2, 150 and 199, of SEQ ID NO: 5.

In yet another embodiment, the invention encompasses a method of controlling insects, comprising delivering to the insects or contacting the insects with an effective amount of an eCry1Ba protein or vCry1Ba protein of the invention. According to this embodiment, the insects are lepidopteran insects or coleopteran insects. Such lepidopteran insects include without limitation European corn borer, southwestern corn borer, sugarcane borer, corn earworm, soybean looper and velvet bean caterpillar. Preferably, the eCry1Ba protein or vCry1Ba protein is delivered to the insects orally. In another embodiment, the protein is delivered orally through a transgenic plant comprising a nucleic acid sequence that expresses an eCry1B protein or vCry1Ba protein of the invention.

The present invention further encompasses a method of controlling insects wherein a transgenic plant of the invention further comprises a second nucleic acid sequence or groups of nucleic acid sequences that encode a second pesticidal principle. In one embodiment, the second nucleic acid sequences are those that encode a Cry protein different than an eCry1Ba protein or vCry1Ba protein of the invention, those that encode a Vegetative Insecticidal Protein toxin, disclosed in U.S. Pat. Nos. 5,849,870 and 5,877,012, incorporated herein by reference, or those that encode a pathway for the production of a non-proteinaceous principle, in another embodiment, the second nucleic acid sequence encodes a Vip3 protein. The skilled person will recognize that many different insecticidal principles may used in combination with an eCry1Ba or vCry1Ba protein of the invention.

In another embodiment, the invention encompasses a method of providing a grower with an improved means of controlling at least European corn borer comprising supplying or selling to the grower transgenic propagules comprising a nucleic acid that encodes an eCry1Ba protein having a mutation at one or more amino acid positions in domain I, the eCry1Ba protein having improved solubility and/or insecticidal activity against at least European corn borer when compared to a native Cry1Ba protein. In another embodiment, the transgenic propagule is selected from the group consisting of a seed, a sette and a cutting.

In further embodiments, the nucleic acid sequences of the invention can be further modified by incorporation of random mutations in a technique known as in vitro recombination or DNA shuffling. This technique is described in Stemmer et al., Nature 370:389-391 (1994) and U.S. Pat. No. 5,605,793, which are incorporated herein by reference. Millions of mutant copies of a nucleic acid sequence are produced based on an original nucleic acid sequence of this invention and variants with improved properties, such as increased insecticidal activity, enhanced stability, or different specificity or ranges of target-insect pests are recovered. The method encompasses forming a mutagenized double-stranded polynucleic acid from a template double-stranded polynucleic acid comprising a nucleic acid sequence of this invention, wherein the template double-stranded polynucleic acid has been cleaved into double-stranded-random fragments of a desired size, and comprises the steps of adding to the resultant population of double-stranded random fragments one or more single or double-stranded oligonucleic acids, wherein said oligonucleic acids comprise an area of identity and an area of heterology to the double-stranded template polynucleic acid; denaturing the resultant mixture of double-stranded random fragments and oligonucleic acids into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleic acid; and repeating the second and third steps for at least two further cycles, wherein the resultant mixture in the second step of a further cycle includes the mutagenized double-stranded polynucleic acid from the third step of the previous cycle, and the further cycle forms a further mutagenized double-stranded polynucleic acid. In a preferred embodiment, the concentration of a single species of double-stranded random fragment in the population of double-stranded random fragments is less than 1% by weight of the total DNA. In a further embodiment, the template double-stranded polynucleic acid comprises at least about 100 species of polynucleic acids. In another preferred embodiment, the size of the double-stranded random fragments is from about 5 bp to 5 kb. In yet a further embodiment, the fourth step of the method comprises repeating the second and the third steps for at least 10 cycles.

Expression of the Nucleic Acid Sequences in Heterologous Microbial Hosts

As biological insect control agents, the insecticidal eCry1Ba proteins are produced by expression of the nucleic, acid sequences in heterologous host cells capable of expressing the nucleic acid sequences. In a first embodiment, *B. thuringiensis* cells comprising modifications of a nucleic acid sequence of this invention are made. Such modifications encompass mutations or deletions of existing regulatory elements, thus leading to altered expression of the nucleic acid sequence, or the incorporation of new regulatory elements controlling the expression of the nucleic acid sequence. In another embodiment, additional copies of one or more of the nucleic acid sequences are added to *Bacillus thuringiensis* cells either by insertion into the chromosome or by introduction of extrachromosomally replicating molecules containing the nucleic acid sequences.

In another embodiment, at least one of the nucleic acid sequences of the invention is inserted into an appropriate expression cassette, comprising a promoter and termination signal. Expression of the nucleic acid sequence is constitutive, or an inducible promoter responding to various types of stimuli to initiate transcription is used. In a preferred embodiment, the cell in which the protein is expressed is a microorganism, such as a virus, bacteria, or a fungus. In one embodiment, a virus, such as a baculovirus, contains a nucleic acid sequence of the invention in its genome and expresses large amounts of the corresponding insecticidal eCry1Ba protein or vCry1Ba protein after infection of appropriate eukaryotic cells that are suitable for virus replication and expression of the nucleic acid sequence. The insecticidal protein thus produced is used as an insecticidal agent. Alternatively, baculoviruses engineered to include the nucleic acid sequence are used to infect insects in vivo and kill them either by expression of the insecticidal protein or by a combination of viral infection and expression of the insecticidal protein.

Bacterial cells are also hosts for the expression of the nucleic acid sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and *Xanthomonas*. Symbiotic fungi, such as *Trichoderma* and *Gliocladium* are also possible hosts for expression of the inventive nucleic acid sequences for the same purpose.

Techniques for these genetic manipulations are specific for the different available hosts and are known in the art. For example, the expression vectors pKK223-3 and pKK223-2 can be used to express heterologous genes in *E. coli*, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as *Bacillus* are also known in the art and can be used in the context of this invention (Quax et al. In: Industrial Microorganisms: Basic and Applied Molecular Genetics, Eds. Baltz et al., American Society for Microbiology, Washington (1993)). Alternate systems for overexpression rely for example, on yeast vectors and include the use of *Pichia, Saccharomyces* and *Kluyveromyces* (Sreektishna, In: Industrial microorganisms: basic and applied molecular genetics, Baltz, Hegeman, and Skatrud eds., American Society for Microbiology, Washington (1993); Dequin & Barre, Biotechnology L2:173-177 (1994); van den Berg et al., Biotechnology 8:135-139 (1990)).

Plant Transformation

In one embodiment, at least one of the insecticidal eCry1B proteins or vCry1Ba proteins of the invention is expressed in a higher organism, e.g., a plant. In this case, transgenic plants expressing effective amounts of the eCry1Ba or vCry1Ba proteins protect themselves from insect pests. When the insect starts feeding on such a transgenic plant, it also ingests the expressed eCry1Ba or vCry1Ba protein. This will deter the insect from further biting into the plant tissue or may even harm or kill the insect. A nucleic acid sequence of the present invention is inserted into an expression cassette, which is then preferably stably integrated in the genome of said plant. In another embodiment, the nucleic acid sequence is included in a non-pathogenic self-replicating virus. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired nucleic acid sequence has been transformed into a particular plant species, it may be propagated in that species or moved into other varieties of the same species, particularly including commercial varieties, using traditional breeding techniques.

A nucleic acid sequence of this invention may be expressed in transgenic plants, thus causing the biosynthesis of the corresponding eCry1Ba or vCry1Ba protein in the transgenic plants. In this way, transgenic plants with enhanced resistance to insects are generated. For their expression in transgenic plants, the nucleic acid sequences of the invention may require other modifications and optimization. Although in many cases genes from microbial organisms can be expressed in plants at high levels without modification, low expression in transgenic plants may result from microbial nucleic acid sequences having codons that are not preferred in plants. It is known in the art that all organisms have specific preferences for codon usage, and the codons of the nucleic acid sequences described in this invention can be changed to conform with plant preferences, while maintaining the amino acids encoded thereby. Furthermore, high expression in plants is best achieved from coding sequences that have at least about 35% GC content, preferably more than about 45%, more preferably more than about 50%, and most preferably more than about 60%. Microbial nucleic acid sequences that have low GC contents may express poorly in plants due to the existence of ATTTA motifs that may destabilize messages, and AATAAA motifs that may cause inappropriate polyadenylation. Although preferred gene sequences may be adequately expressed in both monocotyledonous and dicotyledonous plant species, sequences can be modified to account far the specific codon preferences and GC content preferences of monocotyledons or dicotyledons as these preferences have been shown to differ (Murray et al. Nucl. Acids Res. 17:477-498 (1989)). In addition, the nucleic acid sequences are screened for the existence of illegitimate splice sites that may cause message truncation. All changes required to be made within the nucleic acid sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

In one embodiment of the invention an eCry1Ba coding sequence is made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid might be derived, for example, from known gene sequences from maize. Maize codon usage for 28 genes from maize plants is found in Murray et al., Nucleic Acids Research 17:477-498 (1989), the disclosure of which is incorporated herein by reference. A synthetic sequence made with maize optimized codons is set forth in SEQ ID NO 13.

In this manner, the nucleic acid sequences can be optimized for expression in any plant. It is recognized that all or any part of the gene sequence may be optimized or synthetic. That is, synthetic or partially optimized sequences may also be used.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleic acid sequences of this invention. The sequences are incorporated into constructions comprising the nucleic acid sequences, up to and including the ATG (whilst leaving the second amino acid unmodified), or alternatively up to and including the GTC subsequent to the ATG (with the possibility of modifying the second amino acid of the transgene).

Expression of the nucleic acid sequences in transgenic plants is driven by promoters that function in plants. The choice of promoter will vary depending on the temporal and spatial requirements for expression, and also depending on the target species. Thus, expression of the nucleic acid sequences of this invention in leaves, in stalks or stems, in ears, in inflorescences (e.g. spikes, panicles, cobs, etc.), in roots, and/or seedlings is preferred. In many cases, however, protection against, more than one type of insect pest is sought, and thus expression in multiple tissues is desirable.

Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleic acid sequences in the desired cell.

Promoters that are expressed constitutively include promoters from genes encoding actin or ubiquitin and the CaMV 35S and 19S promoters. The nucleic acid sequences of this invention can also be expressed under the regulation of promoters that are chemically regulated. This enables the insecticidal eCry1Ba or variant Cry1Ba proteins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

Another category of promoters is that which is wound inducible. Numerous promoters have been described which are expressed at wound sites and also at the sites of phytopathogen infection. Ideally, such a promoter should only be active locally at the sites of infection, and in this way the insecticidal eCry1B or variant Cry1Ba proteins only accumulate in cells that need to synthesize the insecticidal eCry1Ba or variant Cry1Ba proteins to kill the invading insect pest. Promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Tissue-specific or tissue-preferential promoters useful for the expression of the eCry1Ba or variant Cry1Ba protein genes in plants, particularly corn, are those which direct expression in root, pith, leaf or pollen, particularly root. Such promoters, e.g. those isolated from PEPC or trpA, are disclosed in U.S. Pat. No. 5,625,136, or MTL, disclosed in U.S. Pat. No. 5,466,785. Both U.S. patents are herein incorporated by reference in their entirety.

Further preferred embodiments are transgenic plants expressing the nucleic acid sequences in a wound-inducible or pathogen infection-inducible manner.

In addition to promoters, a variety of transcriptional terminators are also available for use in chimeric gene construction using the eCry1Ba or variant Cry1Ba protein genes of the present invention. Transcriptional terminators are responsible for the termination of transcription beyond the transgene and its correct polyadenylation. Appropriate transcriptional terminators and those that are known to function in plants include the CaMV 35S terminator, the tm1 terminator, the nopaline synthase terminator, the pea rbcS E9 terminator and others known in the art. These can be used in both monocotyledons and dicotyledons. Any available terminator known to function in plants can be used in the context of this invention.

Numerous other sequences can be incorporated into expression cassettes described in this invention. These include sequences that have been shown to enhance expression such as intron sequences (e.g. from Adh1 and bronze1) and viral leader sequences (e.g. from TMV, MCMV and AMV).

It may be preferable to target expression of the nucleic acid sequences of the invention to different cellular localizations in the plant. In some cases, localization in the cytosol may be desirable, whereas in other cases, localization in some subcellular organelle may be preferred. Subcellular localization of transgene-encoded enzymes is undertaken using techniques well known in the art. Typically, the DNA encoding the target peptide from a known organelle-targeted gene product is manipulated and fused upstream of the nucleic acid sequence. Many such target sequences are known for the chloroplast and their functioning in heterologous constructions has been shown. The expression of the nucleic acid sequences of the invention is also targeted to the endoplasmic reticulum or to the vacuoles of the host cells. Techniques to achieve this are well known in the art.

Vectors suitable for plant transformation are described elsewhere in this specification. For *Agrobacterium*-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4:1093-1096 (1986)). For both direct gene transfer and *Agrobacterium*-mediated transfer, transformation is usually (but not necessarily) undertaken with a selectable marker that may provide resistance to an antibiotic (kanamycin, hygromycin or methotrexate) or a herbicide (basta). Plant transformation vectors comprising the eCry1Ba or variant Cry1Ba protein genes of the present invention may also comprise genes, for example, phosphomannose isomerase (pmi), which provides for positive selection of the transgenic plants as disclosed in U.S. Pat. Nos. 5,767,378 and 5,994,629, herein incorporated by reference, or phosphinotricin acetyltransferase (pat), which provides tolerance to the herbicide phosphinotricin (glufosinate). The choice of selectable marker is not, however, critical to the invention.

In another embodiment, a nucleic acid sequence encoding an eCry1Ba or vCry1Ba protein of the invention is directly transformed into the plastid genome. A major advantage of plastid transformation is that plastids are generally capable of expressing bacterial genes without substantial codon optimization, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P. and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Combinations of Insect Control Principles

The eCry1Ba or vCry1Ba proteins of the invention can be used in combination with other Bt Cry proteins or other pesticidal principles to increase pest target range. Furthermore, the use of the eCry1Ba or vCry1Ba proteins of the invention in combination with other Bt Cry proteins or other pesticidal principles of a distinct nature has particular utility for the prevention and/or management of insect resistance. Other insecticidal principles include, for example, lectins, α-amylase, peroxidase and cholesterol oxidase. Vegetative Insecticidal Protein genes, such as vip1A(a) and vip2A(a) or vip3, are also useful in the present invention. In one embodiment, an eCry1Ba protein designated eCry1Ba-T2AY150KL189S (SEQ ID NO: 9) is combined with a Vip3A protein in a transgenic plant. The transgenic plant exhibits the combined spectrum of insecticidal activity associated with both the eCry1Ba and Vip3. In yet another embodiment, the transgenic plant is a corn plant or a sugar cane plant.

This co-expression of more than one insecticidal principle in the same transgenic plant can be achieved by genetically engineering a plant to contain and express all the genes necessary in a so called molecular stack. Alternatively, a plant, Parent 1, can be genetically engineered for the expression of genes of the present invention. A second plant, Parent 2, can be genetically engineered for the expression of a supplemental insect control principle. By crossing Parent 1 with Parent 2, progeny plants are obtained which express all the genes introduced into Parents 1 and 2. For example without limitation, Parent 1 may contain an eCry1Ba coding sequence and Parent 2 may contain a Vip3A coding sequence. Some progeny of a Parent 1×Parent 2 cross will contain both the eCry1Ba coding sequence and the Vip3A coding sequence.

Transgenic seed of the present invention can also be treated with an insecticidal seed coating as described in U.S. Pat. Nos. 5,849,320 and 5,876,739, herein incorporated by reference. Where both the insecticidal seed coating and the transgenic seed of the invention are active against the same target insect, the combination is useful (i) in a method for enhancing activity of an eCry1Ba protein of the invention against the target insect and (ii) in a method for preventing development of resistance to an eCry1Ba protein of the invention by providing a second mechanism of action against the target insect. Thus, the invention provides a method of enhancing activity against or preventing development of resistance in a target insect, for example corn rootworm, comprising applying an insecticidal seed coating to a transgenic seed comprising one or more eCry1Ba proteins of the invention. Such chemical treatments may include insecticides, fungicides or nematicides. Examples of such insecticides include, without limitation, dinotefuran, such as thiamethoxam, imidacloprid, acetamiprid, nitenpyram, nidinotefuran, chlorfenapyr, tebufenpyrad, tebufenozide, methoxyfenozide, halofenozide, triazamate, avermectin, spinosad, fiprinol, acephate, fenamiphos, diazinon, chlorpyrifos, chloropyrifon-methyl, malathion, carbaryl, aldicarb, carbofuran, thiodicarb, and oxamyl. Even where the insecticidal seed coating is active against a different insect, the insecticidal seed coating is useful to expand the range of insect control, for example by adding an insecticidal seed coating that has activity against lepidopteran insects to the transgenic seed of the invention, which has activity against coleopteran insects, the coated transgenic seed produced controls both lepidopteran and coleopteran insect pests.

EXAMPLES

The invention will be further described by reference to the following detailed examples. These examples are provided for the purposes of illustration only and are not intended to be limiting unless otherwise specified. Standard recombinant DNA and molecular cloning techniques used here are well known in the art and are described by J. Sambrook, et al., Molecular Cloning: *A Laboratory Manual*, 3d Ed. Cold Spring Harbor, N.Y.: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1. Use of PCR to Mutate Cry1Ba Coding Sequences

Polymerase Chain Reaction (PCR) is a repetitive, enzymatic, primed synthesis of a nucleic acid sequence. This procedure is well known and commonly used by those skilled in this art (See Mullis, U.S. Pat. Nos. 4,683,195, 4,683,202, and 4,800,159; Saiki, Randall K., Stephen Scharf, Fred Faloona, Kary B. Mullis, Glenn T. Horn, Henry A. Erlich, Norman Arnheim [1985] "Enzymatic Amplification of β-Globin Genomic Sequences and Restriction Site Analysis for Diagnosis of Sickle Cell Anemia," Science 230:1350-1354.). PCR is based on the enzymatic amplification of a DNA fragment of interest that is flanked by two oligonucleic acid primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA fragment produced in the previous cycle. This results in the exponential accumulation of the specific target fragment, up to several million-fold in a few hours. By using a thermostable DNA polymerase such as Taq polymerase, which is isolated from the thermophilic bacterium *Thermus aquaticus*, the amplification process can be completely automated.

The mutant Cry1Ba coding sequences described, in the following examples were constructed using a QuickChange Site-Directed Mutagenesis Kit (Stratagene, La Jolla, Calif.) according to the manufacturer's instructions and various combinations of the exemplified primers shown in Table 1. The skilled person will recognize based on the present application that other primer pairs can be used to mutate any Cry1Ba coding sequence.

TABLE 1

Primers used to make mutated coding sequence encoding eCry1Ba proteins.

| Primer Name | Primer Sequence | SEQ ID NO: |
|---|---|---|
| YG152 | 5'-agaagtgttcttnnsacccaatatatagctttagaacttg-3' | SEQ ID NO: 14 |
| YG153 | 5'-tatatattgggtsnnaagaacacttctcgttcttgcatc-3' | SEQ ID NO: 15 |
| YG154 | 5'-agaagtgttcttaagacccaatatatagctttagaacttg-3' | SEQ ID NO: 16 |
| YG155 | 5'-tatatattgggtcttaagaacacttctcgttcttgcatc-3' | SEQ ID NO: 17 |
| YG156 | 5'-agaagtgttctttggacccaatatatagctttagaacttg-3' | SEQ ID NO: 18 |
| YG157 | 5'-tatatattgggtccaaagaacacttctcgttcttgcatc-3' | SEQ ID NO: 19 |
| YG160 | 5'-atatgtttaaacatgacttcaaataggaaaaatgagaatgaa-3' | SEQ ID NO: 20 |
| YG161 | 5'-atatgtttaaacatggatctattaccagatgctcgtattg-3' | SEQ ID NO: 21 |
| YG162 | 5'-atatggcgcgcctatctttctaaattatattctgcttcgaagg-3' | SEQ ID NO: 22 |
| YG163 | 5'-aattccatggcgtcaaataggaaaaatgagaatgaaattataaatgc-3' | SEQ ID NO: 23 |
| YG164 | 5'-aattccatggatctattaccagatgctcgtattg-3' | SEQ ID NO: 24 |

TABLE 1-continued

Primers used to make mutated coding sequence encoding eCry1Ba proteins.

| Primer Name | Primer Sequence | SEQ ID NO: |
|---|---|---|
| YG165 | 5'-aattccatggaggatagcttgtgtatagccgagg-3' | SEQ ID NO: 25 |
| YG166 | 5'-aattgagctcttatctttctaaatcatattctgcttcgaagg-3' | SEQ ID NO: 26 |
| YG171 | 5'-agttttctttggggtgaattatggccccgc-3' | SEQ ID NO: 27 |
| YG172 | 5'-taattcaccccaaagaaaactataaaaactagc-3' | SEQ ID NO: 28 |
| YG175 | 5'-caatatatagatttagaacttgattttcttaatg-3' | SEQ ID NO: 29 |
| YG176 | 5'-aagttctaaatctatatattgggtataaagaac-3' | SEQ ID NO: 30 |
| YG179 | 5'-ttacacctatccttattgagagatgcctctc-3' | SEQ ID NO: 31 |
| YG180 | 5'-tctcaataaggataggtgtaaatttgcagcttg-3' | SEQ ID NO: 32 |
| YG183 | 5'-agaacgagaagtgaacttaagacccaatatatagc-3' | SEQ ID NO: 33 |
| YG184 | 5'-acccaatatatagatttagaacttgattttcttaatgcg-3' | SEQ ID NO: 34 |
| YG186 | 5'-gaagttccattattgccggtatatgctcaagctgc-3' | SEQ ID NO: 35 |
| YG188 | 5'-tttcttaataagatgccgcttttcgcaattagaaacc-3' | SEQ ID NO: 36 |
| YG189 | 5'-aagcggcatcttattaagaaaatcaagttctaaagctatatattggg-3' | SEQ ID NO: 37 |
| YG190 | 5'-cttttggtaaggaatttgggcttacatcgcagg-3' | SEQ ID NO: 38 |
| YG191 | 5'-cccaaattccttaccaaaaagagaggcatctctcaat-3' | SEQ ID NO: 39 |
| YG192 | 5'-ccattattgagcgtatatgctcaagctgcaaatttacacc-3' | SEQ ID NO: 40 |
| YG193 | 5'-agcatatacgctcaataatggaacttcttggtttctaattgcg-3' | SEQ ID NO: 41 |

Example 2. Determining Toxicity of Cry1Ba Mutants

Activity of mutant Cry1Ba proteins (described below) against insect pests, including European corn borer (*Ostrinia nubilalis*), sugarcane borer (*Diatraea saccharalis*), southwestern corn borer (*Diatraea grandiosella*), corn earworm (*Helicoverpa zea*), soy bean looper (*Pseudoplusia includens*), velvet bean caterpillar (*Anticarsia gemmatalis*), and Colorado potato beetle (*Leptinotarsa decemlineata*) is determined by a surface contamination method. Briefly, artificial diet for a particular species is poured into 24 well tissue culture plates or small petri dishes. Each well has a surface area of approximately 2 cm². Liquids comprising the mutant Cry1Ba proteins are applied to the surface of the diet in each well. After the liquid is absorbed and dried, test larvae are placed in each well and the then the plate is sealed. Activity of art engineered Cry1Ba protein is compared to a native or wild-type Cry1Ba and recorded as percent mortality or relative activity.

Example 3. Mutations at Position 150 in Full-Length Cry1Ba

Since the six native Cry1Ba proteins vary by only one amino acid in alpha-helix 4, e.g. 4/6 have a tyrosine (Y150) and 2/6 have a histidine (H150) (See FIG. 1), the initial mutagenesis analysis investigated the impact of amino acid position 150 in alpha-helix 4 on the insecticidal activity of full-length Cry1Ba.

A native full-length cry1Ba coding sequence (SEQ ID NO: 1) was cloned into a Bt/*E. coli* pUC18-derived shuttled vector under the control of a Cry1Ac promoter. Using this full-length coding sequence as a template, mutant Cry1Ba proteins were generated by randomly substituting the tyrosine (Tyr) at position 150 with different amino acids using the QuickChange Site-Directed Mutagenesis Kit (Stratagene, La Jolla, Calif.) according to the manufacturer's instructions and primers YG152-YG157 of Table 1. All mutant Cry1Ba proteins were tested against ECB using the method described in Example 2.

The data shown in Table 2 demonstrate that position 150 in the full-length Cry1Ba protein plays an important role in modulating at least ECB toxicity. Several of the mutations reduced the ECB specific activity compared to the native Cry1Ba. Cry1Ab, a protein with high specific activity against ECB, has an arginine (Arg) at the position corresponding to Y150 of the Cry1Ba sequence (position 131 of the Cry1Ab sequence; See FIG. 2A). Interestingly, the Y150R Cry1Ba mutant had only half the activity of the native Cry1Ba protein used in the experiment. Mutations that maintained or slightly increased the activity over native Cry1Ba included Y150K, Y150F, Y150W and Y150P. The mutant Cry1Ba proteins that had lower activity compared to native Cry1Ba were designated as variant Cry1Ba proteins.

TABLE 2

Results of the Cry1Ba-Y150X mutant ECB bioassay.

| Mutant Designation | Amino Acid at Position 150 | Relative ECB Mortality |
|---|---|---|
| M4 | K | ++++ |
| M18 | F | +++ |

TABLE 2-continued

Results of the Cry1Ba-Y150X mutant ECB bioassay.

| Mutant Designation | Amino Acid at Position 150 | Relative ECB Mortality |
|---|---|---|
| M7 | W | +++ |
| M26 | P | +++ |
| M12 | T | ++ |
| M14 | L | ++ |
| M15 | A | ++ |
| M23 | V | ++ |
| M28 | S | ++ |
| M38 | R | + |
| M9 | G | + |
| M24 | D | +/− |
| Native Cry1Ba | Y | +++ |
| Empty Vector (Control) | — | − |

Example 4. Toxicity of Truncated Cry1Ba Compared to Full-Length Cry1Ba

Based on what is known in the art, it is not clear what exact proteolytic sites in Cry1Ba are targeted by insect gut proteases. Therefore, the sequence of the active toxin is unclear. For this example, cleavage sites for Cry1Ba protoxin were predicted based on a sequence alignment with Cry1Ab (See FIG. 2), whose cleavage sites have been reported. Using this information, vectors that express truncated versions of Cry1Ba were constructed.

A truncated cry1Ba fragment was PCR cloned into vector pCIB5634 or pET28a using the full-length native cry1Ba coding sequence (SEQ ID NO: 1) as the template and primers YG160 and YG162 or YG163 and YG166, respectively. The resulting PCR fragment encodes a truncated protein comprising amino acids 1-647 of SEQ ID NO: 2. However, during the initial cloning of the truncated cry1Ba coding sequence into the vectors, a mutation was introduced whereby the threonine at position 2 (T2) was replaced with an alanine (Ala; A) (T2A mutation). This T2A mutation was determined to have no negative impact on insecticidal activity compared to the native Cry1Ba and therefore was used in all subsequent mutation experiments. This T2A mutant was designated the T25 wild-type Cry1Ba.

Another truncated cry1Ba fragment was PCR cloned into vector pCIB5634 or pET28a using the T25 coding sequence as a template and primers YG161 and YG162 or YG164 and YG166, respectively. The resulting PCR fragment encodes an N-terminal and C-terminal truncated protein (SEQ ID NO: 42) comprising amino acids 22-647 of SEQ ID NO: 2 and was designated T7.

Western blot results demonstrate that the T25 truncated Cry1Ba (comprising amino acids 1-647) in both the pCIB5634 and pET28a vectors was more stable than the T7 truncated Cry1Ba toxin in either vector. Results of the bioassay (Table 3) showed that the T25 wild-type toxin was 15× more active than the T7 construct and 3× more active than the full-length Cry1Ba protein. Therefore, further Cry1Ba mutants were constructed using the wild-type T25 truncated Cry1Ba.

TABLE 3

Activity of truncated vs. full-length Cry1Ba against ECB.

| Clone | Amino acids | Activity Relative to Full-Length Cry1Ba |
|---|---|---|
| T25 | 1-647 | 3.0 |
| T7 | 22-647 | 0.2 |
| FL-Cry1Ba | 1-1228 | 1.0 |
| Vector Control | — | 0.0 |

Example 5. Effects of Mutating Y150 in Truncated Cry1Ba

The imitations at amino acid position 150 that did not decrease insecticidal activity, including Y150K, Y150F, Y150W and Y150P, of the full-length Cry1Ba protein were tested in the T25 truncated Cry1Ba toxin. The Y150K, Y150F, Y150W and Y150P mutations were made as described above using the YG152-YG157 primers.

Making these mutations in the truncated T25 protein lead to different results than in the full-length Cry1Ba protein. For example, the Y150P mutation in the T25 truncated toxin completely knocked out ECB activity. However, the same mutation in the full-length Cry1Ba had no negative impact on ECB activity (See Example 3). Surprisingly, all the mutations except the Y150K mutation reduced the T25 ECB activity to some degree (Table 4). All known native Cry1Ba proteins have either a histidine (H) or a tyrosine (Y) at position 150. The Y150K mutation substantially altered the biological properties of the eCry1Ba-Y150K mutant compared to both the "H150-type" native Cry1Ba and the "Y150-type" native Cry1Ba. The Y150K mutant was 3 times more active than a Cry1Ba protein with a histidine (His) at position 150.

TABLE 4

Activity of truncated Y150X mutants.

| Mutant Designation | Amino Acid at Position 150 | ECB Activity Relative to T25 |
|---|---|---|
| TM9 | P | 0.00 |
| TM5 | F | 0.25 |
| TM15 | H | 0.58 |
| TM27 | W | 0.75 |
| TM2 | K | 1.60 |
| T25 (wt) | Y | 1.00 |
| Empty Vector (Control) | — | 0.00 |

Each of the mutant T25 Cry1Ba proteins was tested for its solubility properties. Solubility of the proteins correlated with insecticidal activity. For example, the eCry1Ba-Y150K protein was more soluble than wild-type T25-Cry1Ba and any of the other mutant proteins. Therefore, these data demonstrate that changing the amino acid at position 150 has a dramatic impact on the solubility and insecticidal activity of a truncated Cry1Ba protein. For example, mutating the tyrosine (Tyr) at position 150 to lysine (Lys) substantially increases the solubility and specific activity of the truncated Cry1Ba toxin against ECB compared to the wild-type truncated Cry1Ba toxin (T25). The eCry1Ba-Y150K protein (TM2) was used for further mutational analysis experiments.

Example 6. Construction and Testing of Additional eCry1Ba Mutants

Cry1Ab has a high specific activity against ECB. Therefore, a sequence alignment was done between a Cry1Ab and the T25-Cry1Ba protein to help identify key amino acid positions in alpha-helix 4 or 5 that may be important to Cry1Ba activity or solubility. The sequence alignment between Cry1Ab and Cry1Ba is shown in FIG. 2. A comparison of the structural features of Cry1Ab and Cry1Ba is shown in Table 8 in Example 10 below. Further mutational analysis was carried out on the identified key amino acid positions to determine whether mutations in addition to the Y150K mutation would limber increase the specific activity of this eCry1Ba protein. The TM2 coding sequence (SEQ ID NO: 4) was used as a template for further site-directed mutagenesis. The mutations were made as described above using the YG171-YG193 primers listed in Table 1.

Eleven mutants were tested for activity against European corn borer. Table 5 shows the results of the bioassays. Of the 11 mutants tested, two mutations, L189S and S199K, increased the specific activity of the TM2-Y150K mutant against ECB, which was at least a 3× increase in specific activity over the wild-type Cry1Ba (T25). These were designated as engineered Cry1Ba (eCry1Ba) proteins. Two mutations, V81W and M178S/A155S, had the same activity as TM2, and two mutants, M178P and R170S, had less activity than TM2. These mutants were categorized as variant Cry1Ba proteins (vCry1Ba). Four mutations, V148E/A155D, A155K, A163K and A163K/L188P knocked out activity completely, indicating that these positions are critical for at least ECB activity.

TABLE 5

Activity of TM2-Cry1Ba mutants compared to wild-type Cry1Ba.

| Clone | Mutations | Relative Activity | SEQ ID NO: |
|---|---|---|---|
| T25 | T2A (wt) | 1.0 | SEQ ID NO: 5 |
| TM2 | Y150K | 2.0 | SEQ ID NO: 7 |
| TM21 | Y150K/V81W | 1.0 | SEQ ID NO: 11 |
| TM60 | Y150K/V148E/A155D | 0.0 | — |
| TM33 | Y150K/L189S | 3.0 | SEQ ID NO: 9 |
| TM88 | Y150K/M178S | 2.0 | SEQ ID NO: 8 |
| TM90 | Y150K/M178S/A155S | 1.0 | SEQ ID NO: 12 |
| TM69 | Y150K/M178P | 0.5 | SEQ ID NO: 43 |
| TM61 | Y150K/R170S | 0.5 | SEQ ID NO: 44 |
| TM70 | Y150K/A155K | 0.0 | — |
| TM78 | Y150K/A163K | 0.0 | — |
| TM82 | Y150K/A163K/L188P | 0.0 | — |
| TM83 | Y150K/S199K | 3.0 | SEQ ID NO: 10 |

Spectrum of eCry1Ba Protein

The TM33 mutant (eCry1Ba-T2AY150KL189S) was tested against several other lepidopteran insects, including sugarcane borer (SCB; *Diatraea saccharalis*), southwestern corn borer (SWCB; *Diatraea grandiosella*), corn earworm (CEW, *Helicoverpa zea*), velvet bean caterpillar (VBC; *Anticarsia gemmatalis*), and soybean looper (SBL, *Pseudoplisia includens*, now named *Chrysodeixis includens*), using a surface treated artificial diet bioassays. Larval mortality was assessed after approximately 4-6 days depending on the insect species tested.

Native Cry1Ba has been reported to be active against sugarcane borer, southwest corn borer and soybean looper and to have no activity against corn earworm. In addition, some reports have suggested that Bt strains comprising a Cry1B-type protein have activity against velvet bean caterpillar (Bobrowski et al. 2001. Brazil. J. Microbiol. 32:105-109), but it is not clear from this report whether this activity is due to a Cry1Ba protein or to some other protein expressed in the Bt strain tested. Other reports (For example, Monnerat et al. 2007. Biological Control 41:291-295) demonstrate that Cry1B present in Bt strains contributes little to toxicity of such strains to VBC larvae.

Results of the bioassay of the eCry1Ba-T2AY150KL189S mutant showed that this protein, like the native Cry1Ba protein, is active against sugarcane borer, southwestern corn borer and soybean looper. Unlike the native Cry1Ba protein, the eCry1Ba protein was very active against velvet bean caterpillar. Surprisingly, the eCry1Ba protein also had some activity against corn earworm, an insect for which native Cry1Ba has no activity. The activity of eCry1Ba protein against velvet bean caterpillar and corn earworm is another indication that eCry1Ba is substantially different from native Cry1Ba protein.

Since native Cry1Ba is known to be active against both lepidopteran and coleopteran insects, the TM33 eCry1Ba protein was tested against the coleopteran insect, Colorado potato beetle (CPB; *Leptinotarsa decemlineata*). Bioassays were carried out using neonate CPB larvae and a standard artificial diet assay as described in Example 2 above. As was already known in the art, the native Cry1Ba protein was active against CPB. The wild-type Cry1Ba mutant, T25, was also active. Surprisingly, the T33 eCry1Ba protein was not active against CPB. Therefore, although the mutations in T33 increase the specific activity against at least European corn borer, these mutations knocked out the activity against the coleopteran insect, Colorado potato beetle, which is yet another indication that the properties of eCry1Ba proteins are substantially different than native Cry1Ba and wild-type Cry1Ba proteins. Using this approach the skilled person will recognize that mutation of amino acids in domain I, particularly alpha-helix 4 and alpha-helix 5, of a Cry1Ba provides a method to change the spectrum of activity of Cry1Ba.

The mutants described above were tested for differences in solubility properties using standard methods known in the art. Briefly, cell pellets from induced *E. coli* cultures expressing Cry1Ba mutants and wild type Cry1Ba were treated in BugBuster™ protein extraction reagent (Novagen, Inc) with protease inhibitors and lysonase according to the manufacturer's instructions. Cell lysates and soluble fractions after centrifugation of cell lysates were analyzed on SDS-PAGE and western blot using rabbit-anti-Cry1Ba antibody, and Cry1Ba protein on western blot were quantified by AlphaImager (Cell Biosciences). Although the mutant Cry1Ba and the wild-type T25 showed similar level of protein expression in cell lysates, the amount of protein present in soluble fractions was surprisingly quite different between mutants and wild type. To compare solubility, Cry1Ba mutant proteins present in soluble fractions were normalized over wild type Cry1Ba. Results in Table 6 demonstrate that eCry1Ba mutants had in the range of 1.5 to 2.1 times more soluble eCry1Ba protein than the wild-type T25 Cry1Ba protein in the same amount of liquid under the same environmental conditions. "SP" in Table 6 means soluble protein; and "TP" means total protein.

TABLE 6

Solubility comparison of eCry1Ba proteins and wild-type T25 Cry1Ba protein.

| Clone | Mutations | Percent SP/TP | Fold Increase over Wild-type (T25) |
|---|---|---|---|
| T25 (Wild-type) | T2A | 52 | 1.0 |
| TM33 | T2A, Y150K, L189S | 76 | 1.5 |
| TM2 | T2A, Y150K | 86 | 1.7 |
| TM83 | T2A, Y150K, S199K | 107 | 2.1 |

Example 7. Maize-Optimized ecry1B Gene Construction

A maize optimized nucleotide sequence (mocry1Ba-TM33) that encodes the TM33 Cry1Ba mutant (eCry1Ba-T2A:Y150K:L189S) protein was generated as described in U.S. Pat. No. 6,051,760, herein incorporated by reference. The mocry1Ba-TM33 coding sequence is set forth in SEQ ID NO: 13. The eCry1Ba-T2A:Y150K:L189S amino acid sequence is set forth in SEQ ID NO 9.

Example 8. Transgenic Maize and Sugarcane Expressing eCry1Ba Protein

Two plant transformation vectors are constructed for introduction of the mocry1Ba-TM33 coding sequence into maize: (a) a first vector (18320) comprising two expression cassettes, a first expression cassette comprising a maize ubiquitin promoter (ZmUbiInt) (Christensen et al. 1992 PMB 18: 675) operably linked to the TM33 coding sequence further operably linked to a nopaline synthase 3' end transcription termination and polyadenylation sequence, designated as ZmUbi:mocry1Ba-TM33:NOS, and a second expression cassette comprising a 35S:pat:NOS, and (h) a second vector (18319) comprising two expression cassettes, a first expression cassette comprising a MTL promoter sequence (U.S. Pat. No. 6,018,099) operably linked to the TM33 coding sequence further operably linked to a nopaline synthase 3' end transcription termination and polyadenylation sequence, designated as MTL:mocry1Ba-TM33:NOS, and a second expression cassette comprising 35S:pat:NOS. All vectors in this example comprise the pat gene encoding a phosphinotricin acetyltransferase (PAT), which confers tolerance to the herbicide phosphinotricin for selection of transgenic events.

Both vectors are individually transformed into maize. *Agrobacterium* transformation of immature maize embryos is performed essentially as described in Negrotto et al., 2000, Plant Cell Reports 19: 798-803. For this example, all media constituents are essentially as described in Negrotto et al., supra. However, various media constituents known in the art may be substituted.

Briefly, *Agrobacterium* strain LBA4404 (pSB1) containing a plant transformation plasmid is grown on YEP (yeast extract (5 g/L), peptone (10 g/L), NaCl (5 g/L), 15 g/l agar, pH 6.8) solid medium for 2-4 days at 28° C. Approximately $0.8\times10^9$ *Agrobacterium* are suspended in LS-inf media supplemented with 100 μM As (Negrotto et al., supra). Bacteria are pre-induced in this medium for 30-60 minutes.

Immature embryos from a suitable genotype are excised from 8-12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) and cultured in the dark for 28° C. for 10 days.

Immature embryos, producing embryogenic callus are transferred to LSD1M0.5S medium. The cultures are selected on this medium for about 6 weeks with as subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the pat gene and the mocry1Ba-TM33 coding sequence. Positive plants from the PCR assay are transferred to the greenhouse and tested for resistance to at least European corn borer.

Sugarcane Transformation

A plant transformation vector (72581) comprising two expression cassettes was constructed for introduction, of the mocry1Ba-TM33 coding sequence into sugarcane. The first expression cassette comprises a maize Ubi361 promoter (PCT/US10/37683) operably linked to the TM33 coding sequence further operably linked to a maize Ubi361 3' end transcription termination and polyadenylation sequence (PCT/US10/37683), designated as prZmUbi361-3:mocry1Ba-TM33:tZmUbi361. The second expression cassette comprises a maize ubiquitin promoter (ZmUbiInt) (Christensen et al. 1992 PMB 18: 675) operably linked to a pmi coding sequence further operably linked to a nopaline synthase (nos) 3' end transcription termination and polyadenylation sequence. The pmi coding sequence encodes phosphomannose isomerase (PMI), which enables transgenic sugarcane to utilize mannose and functions as a selectable marker for transformation. The 72581 vector was transformed into sugarcane using *Agrobacterium* transformation. Transgenic sugarcane plants were tested against neonate sugarcane borer as described above.

Example 9. Insecticidal Activity of Transgenic Maize and Sugarcane Plants

Plants were sampled as they are being transplanted from Magenta GA-7 boxes into soil. Sampling consisted of cutting two small pieces of leaf (ca. 2-4 cm long) and placing each in a small petri dish or multi-well plates. Negative controls were either transgenic plants that were PCR negative for the mocry1Ba-TM33 gene from the same experiment, or from non-transgenic plants (of a similar size to test plants) that are being grown in a greenhouse or phytotron.

Leaf samples from each plant were inoculated with a suitable target insect pest by placing approximately 10 first instar larvae onto each leaf piece. Petri dishes or multi-well plates were then tightly sealed.

At about 3-4 days post inoculation, data was collected. The percent mortality of the larvae was calculated along with a visual damage rating of the leaf. Feeding damage is rated as high, moderate, low, or absent and given a numerical value of 3, 2, 1 or 0, respectively. A "+" in the tables below indicate that mortality was >80% and that leaf damage was 0-1.

Results shown in Table 7 indicate that transgenic maize plants comprising the moTM33 gene and expressing the eCry1Ba-T2A:Y150K:L189S mutant protein, are insecticidal to at least European corn borer. Although both constructs produced transgenic events that were very active against at least ECB, generally transgenic plants with the zmUbi promoter driving expression of the TM33 coding sequence produced higher levels of eCry1Ba protein than transgenic plants comprising the MTL promoter. The eCry1Ba protein concentration ranged from 460-681 μg/mg soluble protein for the 18319 construct and 509-2984 μg/mg soluble protein for the 18320 construct.

TABLE 7

| Activity of transgenic maize expressing eCry1Ba proteins | | | |
|---|---|---|---|
| Construct | Maize Event | ECB Activity | eCry1Ba Concentration (μg/mg soluble protein) |
| 18319 | 9A | + | 648 |
| | 23A | + | 676 |
| | 38A | + | 624 |
| | 40A | + | 460 |
| | 52A | + | 681 |
| | 57A | + | 618 |
| 18320 | 28A | + | 1839 |
| | 29B | + | 2818 |
| | 34C | + | 2984 |
| | 42A | + | 1625 |
| | 46A | + | 1010 |
| | 48B | + | 509 |

Results shown in Table 8 indicate that transgenic sugarcane plants expressing the eCry1Ba-T2A:Y150K:L189S mutant protein are insecticidal to sugarcane borer.

TABLE 8

| Activity of transgenic sugarcane expressing eCry1Ba and Vip3 | |
|---|---|
| Event | SCB |
| 72581-1A | + |
| 72581-2A | + |
| 72581-3A | + |
| 72581-4A | + |
| 72581-5A | − |
| Control | − |

Example 10. Structure of Cry1Ba Protein

Table 9 shows the relationship between the three domains of Cry1Ab (SEQ ID NO:51) and Cry1Ba (SEQ ID NO:2) with their respective variable regions and conserved blocks. The amino acids comprised in each domain, conserved block and variable region is shown for both proteins.

TABLE 9

| Comparison of structure of Cry1Ab and Cry1Ba. | | | |
|---|---|---|---|
| DOMAIN | REGION | Cry1Ab (SEQ ID NO: 51) | Cry1Ba (SEQ ID NO: 2) |
| | V1 | 1-32 | 1-47 |
| I | V1 | 33-152 | 48-171 |
| | CB1 | 153-182 | 172-201 |
| | V2 | 183-202 | 202-221 |
| | CB2 | 203-254 | 222-270 |
| II | | 255-269 | 271-288 |
| | V3 | 270-452 | 289-480 |
| | CB3 | 453-462 | 481-490 |
| III | | 463-500 | 491-528 |
| | V4 | 501-520 | 529-548 |
| | CB4 | 521-531 | 549-559 |
| | V5 | 532-596 | 560-624 |
| | CB5 | 597-606 | 625-634 |
| | V6 | 607-610 | 635-638 |
| | Protoxin | 611-1155 | 639-1228 |

It should be understood that the examples and embodiments described herein are for illustrative purposes only and that various modifications or changes in light thereof will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

SEQUENCE LISTING

```
<160> NUMBER OF SEQ ID NOS: 51

<210> SEQ ID NO 1
<211> LENGTH: 3687
<212> TYPE: DNA
<213> ORGANISM: Bacillus thuringiensis
<220> FEATURE:
<221> NAME/KEY: misc_feature
<222> LOCATION: (1)..(3687)
<223> OTHER INFORMATION: Native full-length cry1Ba coding sequence

<400> SEQUENCE: 1
ttgacttcaa ataggaaaaa tgagaatgaa attataaatg ctgtatcgaa tcattccgca     60
caaatggatc tattaccaga tgctcgtatt gaggatagct tgtgtatagc cgaggggaac    120
aatatcgatc catttgttag cgcatcaaca gtccaaacgg gtattaacat agctggtaga    180
atactaggcg tattgggcgt accgtttgct ggacaactag ctagttttta tagttttctt    240
gttggtgaat tatggccccg cggcagagat cagtgggaaa ttttcctaga acatgtcgaa    300
caacttataa atcaacaaat aacagaaaat gctaggaata cggctcttgc tcgattacaa    360
ggtttaggag attccttcag agcctatcaa cagtcacttg aagattggct agaaaaccgt    420
gatgatgcaa gaacgagaag tgttctttat acccaatata tagctttaga acttgatttt    480
cttaatgcga tgccgctttt cgcaattaga aaccaagaag ttccattatt gatggtatat    540
```

```
gctcaagctg caaatttaca cctattatta ttgagagatg cctctctttt tggtagtgaa      600
tttgggctta catcgcagga aattcaacgc tattatgagc gccaagtgga acgaacgaga      660
gattattccg actattgcgt agaatggtat aatacaggtc taaatagctt gagagggaca      720
aatgccgcaa gttgggtacg gtataatcaa ttccgtagag atctaacgtt aggagtatta      780
gatctagtgg cactattccc aagctatgac actcgcactt atccaataaa tacgagtgct      840
cagttaacaa gagaagttta tacagacgca attggagcaa cagggtaaa tatgcaagt       900 atgaattggt ataataataa tgcaccttcg ttctctgcca tagaggctgc ggctatccga      960
agcccgcatc tacttgattt tctagaacaa cttacaattt ttagcgcttc atcacgatgg     1020
agtaatacta ggcatatgac ttattggcgg gggcacacga ttcaatctcg gccaatagga     1080
ggcggattaa atacctcaac gcatggggct accaatactt ctattaatcc tgtaacatta     1140
cggttcgcat ctcgagacgt ttataggact gaatcatatg caggagtgct tctatgggga     1200
atttaccttg aacctattca tggtgtccct actgttaggt ttaattttac gaaccctcag     1260
aatatttctg atagaggtac cgctaactat agtcaacctt atgagtcacc tgggcttcaa     1320
ttaaaagatt cagaaactga attaccacca gaaacaacag aacgaccaaa ttatgaatct     1380
tacagtcaca ggttatctca tataggtata attttacaat ccagggtgaa tgtaccggta     1440
tattcttgga cgcatcgtag tgcagatcgt acgaatacga ttggaccaaa tagaatcacc     1500
caaatcccaa tggtaaaagc atccgaactt cctcaaggta ccactgttgt tagaggacca     1560
ggatttactg gtggggatat tcttcgaaga acgaatactg gtggatttgg accgataaga     1620
gtaactgtta acgaccatt aacacaaaga tatcgtatag gattccgcta tgcttcaact     1680
gtagattttg atttctttgt atcacgtgga ggtactactg taaataattt tagattccta     1740
cgtacaatga acagtggaga cgaactaaaa tacggaaatt ttgtgagacg tgcttttact     1800 acaccttta cttttacaca aattcaagat ataattcgaa cgtctattca aggccttagt     1860
ggaaatgggg aagtgtatat agataaaatt gaaattattc cagttactgc aaccttcgaa     1920
gcagaatatg atttagaaag agcgcaagag gcggtgaatg ctctgtttac taatacgaat     1980
ccaagaagat tgaaaacaga tgtgacagat tatcatattg atcaagtatc caatttagtg     2040
gcgtgtttat cggatgaatt ctgcttggat gaaagagag aattacttga gaaagtgaaa     2100
tatgcgaaac gactcagtga tgaaagaaac ttactccaag atccaaactt cacatccatc     2160
aataagcaac cagacttcat atctactaat gagcaatcga atttcacatc tatccatgaa     2220
caatctgaac atggatggtg gggaagtgag aacattacca tccaggaagg aaatgacgta     2280
tttaaagaga attacgtcac actaccgggt acttttaatg agtgttatcc gacgtattta     2340
tatcaaaaaa tagggggagtc ggaattaaaa gcttatactc gctaccaatt aagaggttat     2400
attgaagata gtcaagattt agagatatat ttgattcgtt ataatgcgaa acatgaaaca     2460
ttggatgttc caggtaccga gtccctatgg ccgctttcag ttgaaagccc aatcggaagg     2520
tgcggagaac cgaatcgatg cgcaccacat tttgaatgga atcctgatct agattgttcc     2580
tgcagagatg gagaaaaatg tgcgcatcat tcccatcatt tctctttgga tattgatgtt     2640
ggatgcacag acttgcatga gaatctaggc gtgtgggtgg tattcaagat taagacgcag     2700
gaaggtcatg caagactagg gaatctggaa tttattgaag agaaaccatt attaggagaa     2760
gcactgtctc gtgtgaagag ggcagagaaa aaatggagag acaaacgtga aaaactacaa     2820
ttggaaacaa aacgagtata tacagaggca aaagaagctg tggatgcttt attcgtagat     2880
tctcaatatg atagattaca agcggataca aacatcggca tgattcatgc ggcagataaa     2940
```

```
cttgttcatc gaattcgaga ggcgtatctt tcagaattac ctgttatccc aggtgtaaat    3000
gcggaaattt tgaagaatt agaaggtcac attatcactg caatctcctt atacgatgcg    3060
agaaatgtcg ttaaaaatgg tgattttaat aatggattaa catgttggaa tgtaaaaggg    3120
catgtagatg tacaacagag ccatcatcgt tctgaccttg ttatcccaga atgggaagca    3180
gaagtgtcac aagcagttcg cgtctgtccg ggtgtggct atatccttcg tgtcacagcg    3240
tacaaagagg gatatggaga gggctgcgta acgatccatg aaatcgagaa caatacagac    3300
gaactaaaat ttaaaaaccg tgaagaagag gaagtgtatc caacggatac aggaacgtgt    3360
aatgattata ctgcacacca aggtacagct ggatgcgcag atgcatgtaa ttcccgtaat    3420
gctggatatg aggatgcata tgaagttgat actacagcat ctgttaatta caaaccgact    3480
tatgaagaag aaacgtatac agatgtaaga agagataatc attgtgaata tgacagaggg    3540
tatgtcaatt atccaccagt accagctggt tatgtgacaa agaattaga atacttccca    3600 gaaacagata cagtatggat tgagattgga gaaacggaag gaaagtttat tgtagatagc    3660
gtggaattac tcctcatgga agaatag                                        3687
```

<210> SEQ ID NO 2
<211> LENGTH: 1228
<212> TYPE: PRT
<213> ORGANISM: Bacillus thuringiensis

<400> SEQUENCE: 2

```
Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240
```

```
Asn Ala Ala Ser Trp Val Arg Tyr Asn Gln Phe Arg Arg Asp Leu Thr
            245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
            275                 280                 285

Asp Ala Ile Gly Ala Thr Gly Val Asn Met Ala Ser Met Asn Trp Tyr
            290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                    325                 330                 335

Ser Ser Arg Trp Ser Asn Thr Arg His Met Thr Tyr Trp Arg Gly His
                340                 345                 350

Thr Ile Gln Ser Arg Pro Ile Gly Gly Leu Asn Thr Ser Thr His
                355                 360                 365

Gly Ala Thr Asn Thr Ser Ile Asn Pro Val Thr Leu Arg Phe Ala Ser
            370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                    405                 410                 415

Thr Asn Pro Gln Asn Ile Ser Asp Arg Gly Thr Ala Asn Tyr Ser Gln
                420                 425                 430

Pro Tyr Glu Ser Pro Gly Leu Gln Leu Lys Asp Ser Glu Thr Glu Leu
                435                 440                 445

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                    485                 490                 495

Asn Arg Ile Thr Gln Ile Pro Met Val Lys Ala Ser Glu Leu Pro Gln
                500                 505                 510

Gly Thr Thr Val Val Arg Gly Pro Gly Phe Thr Gly Gly Asp Ile Leu
                515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                    565                 570                 575

Phe Arg Phe Leu Arg Thr Met Asn Ser Gly Asp Glu Leu Lys Tyr Gly
                580                 585                 590

Asn Phe Val Arg Arg Ala Phe Thr Thr Pro Phe Thr Phe Thr Gln Ile
                595                 600                 605

Gln Asp Ile Ile Arg Thr Ser Ile Gln Gly Leu Ser Gly Asn Gly Glu
610                 615                 620

Val Tyr Ile Asp Lys Ile Glu Ile Pro Val Thr Ala Thr Phe Glu
625                 630                 635                 640

Ala Glu Tyr Asp Leu Glu Arg Ala Gln Glu Ala Val Asn Ala Leu Phe
                    645                 650                 655
```

```
Thr Asn Thr Asn Pro Arg Arg Leu Lys Thr Asp Val Thr Asp Tyr His
            660                 665                 670

Ile Asp Gln Val Ser Asn Leu Val Ala Cys Leu Ser Asp Glu Phe Cys
        675                 680                 685

Leu Asp Glu Lys Arg Glu Leu Leu Glu Lys Val Lys Tyr Ala Lys Arg
    690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
        740                 745                 750

Thr Ile Gln Glu Gly Asn Asp Val Phe Lys Glu Asn Tyr Val Thr Leu
    755                 760                 765

Pro Gly Thr Phe Asn Glu Cys Tyr Pro Thr Tyr Leu Tyr Gln Lys Ile
    770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
        820                 825                 830

Ser Val Glu Ser Pro Ile Gly Arg Cys Gly Glu Pro Asn Arg Cys Ala
    835                 840                 845

Pro His Phe Glu Trp Asn Pro Asp Leu Asp Cys Ser Cys Arg Asp Gly
    850                 855                 860

Glu Lys Cys Ala His His Ser His His Phe Ser Leu Asp Ile Asp Val
865                 870                 875                 880

Gly Cys Thr Asp Leu His Glu Asn Leu Gly Val Trp Val Phe Lys
                885                 890                 895

Ile Lys Thr Gln Glu Gly His Ala Arg Leu Gly Asn Leu Glu Phe Ile
        900                 905                 910

Glu Glu Lys Pro Leu Leu Gly Glu Ala Leu Ser Arg Val Lys Arg Ala
    915                 920                 925

Glu Lys Lys Trp Arg Asp Lys Arg Glu Lys Leu Gln Leu Glu Thr Lys
    930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
                965                 970                 975

Ala Ala Asp Lys Leu Val His Arg Ile Arg Glu Ala Tyr Leu Ser Glu
        980                 985                 990

Leu Pro Val Ile Pro Gly Val Asn Ala Glu Ile Phe Glu Glu Leu Glu
        995                 1000                1005

Gly His Ile Ile Thr Ala Ile Ser Leu Tyr Asp Ala Arg Asn Val
        1010                1015                1020

Val Lys Asn Gly Asp Phe Asn Asn Gly Leu Thr Cys Trp Asn Val
        1025                1030                1035

Lys Gly His Val Asp Val Gln Gln Ser His His Arg Ser Asp Leu
        1040                1045                1050

Val Ile Pro Glu Trp Glu Ala Glu Val Ser Gln Ala Val Arg Val
        1055                1060                1065

Cys Pro Gly Cys Gly Tyr Ile Leu Arg Val Thr Ala Tyr Lys Glu
```

-continued

```
                    1070                1075                1080

Gly Tyr Gly Glu Gly Cys Val Thr Ile His Glu Ile Glu Asn Asn
            1085                1090                1095

Thr Asp Glu Leu Lys Phe Lys Asn Arg Glu Glu Glu Val Tyr
        1100                1105                1110

Pro Thr Asp Thr Gly Thr Cys Asn Asp Tyr Thr Ala His Gln Gly
        1115                1120                1125

Thr Ala Gly Cys Ala Asp Ala Cys Asn Ser Arg Asn Ala Gly Tyr
        1130                1135                1140

Glu Asp Ala Tyr Glu Val Asp Thr Thr Ala Ser Val Asn Tyr Lys
        1145                1150                1155

Pro Thr Tyr Glu Glu Glu Thr Tyr Thr Asp Val Arg Arg Asp Asn
        1160                1165                1170

His Cys Glu Tyr Asp Arg Gly Tyr Val Asn Tyr Pro Pro Val Pro
        1175                1180                1185

Ala Gly Tyr Val Thr Lys Glu Leu Glu Tyr Phe Pro Glu Thr Asp
        1190                1195                1200

Thr Val Trp Ile Glu Ile Gly Glu Thr Glu Gly Lys Phe Ile Val
        1205                1210                1215

Asp Ser Val Glu Leu Leu Leu Met Glu Glu
        1220                1225

<210> SEQ ID NO 3
<211> LENGTH: 1228
<212> TYPE: PRT
<213> ORGANISM: Artificial Sequence
<220> FEATURE:
<223> OTHER INFORMATION: Mutated Full-Length Cry1Ba
<220> FEATURE:
<221> NAME/KEY: MISC_FEATURE
<222> LOCATION: (150)..(150)
<223> OTHER INFORMATION: X=K, F, W, P, T, L

```
Leu Met Val Tyr Ala Gln Ala Ala Asn Leu His Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Leu Asn Thr Ser Thr His
        355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
```

```
                    595                 600                 605
      Gln Asp Ile Ile Arg Thr Ser Ile Gln Gly Leu Ser Gly Asn Gly Glu
          610                 615                 620

Val Tyr Ile Asp Lys Ile Glu Ile Pro Val Thr Ala Thr Phe Glu
      625                 630                 635                 640

Ala Glu Tyr Asp Leu Glu Arg Ala Gln Glu Ala Val Asn Ala Leu Phe
                      645                 650                 655

Thr Asn Thr Asn Pro Arg Arg Leu Lys Thr Asp Val Thr Asp Tyr His
                      660                 665                 670

Ile Asp Gln Val Ser Asn Leu Val Ala Cys Leu Ser Asp Glu Phe Cys
                      675                 680                 685

Leu Asp Glu Lys Arg Glu Leu Leu Glu Lys Val Lys Tyr Ala Lys Arg
          690                 695                 700

Leu Ser Asp Glu Arg Asn Leu Leu Gln Asp Pro Asn Phe Thr Ser Ile
      705                 710                 715                 720

Asn Lys Gln Pro Asp Phe Ile Ser Thr Asn Glu Gln Ser Asn Phe Thr
                      725                 730                 735

Ser Ile His Glu Gln Ser Glu His Gly Trp Trp Gly Ser Glu Asn Ile
                      740                 745                 750

Thr Ile Gln Glu Gly Asn Asp Val Phe Lys Glu Asn Tyr Val Thr Leu
                      755                 760                 765

Pro Gly Thr Phe Asn Glu Cys Tyr Pro Thr Tyr Leu Tyr Gln Lys Ile
      770                 775                 780

Gly Glu Ser Glu Leu Lys Ala Tyr Thr Arg Tyr Gln Leu Arg Gly Tyr
      785                 790                 795                 800

Ile Glu Asp Ser Gln Asp Leu Glu Ile Tyr Leu Ile Arg Tyr Asn Ala
                      805                 810                 815

Lys His Glu Thr Leu Asp Val Pro Gly Thr Glu Ser Leu Trp Pro Leu
                      820                 825                 830

Ser Val Glu Ser Pro Ile Gly Arg Cys Gly Glu Pro Asn Arg Cys Ala
                      835                 840                 845

Pro His Phe Glu Trp Asn Pro Asp Leu Asp Cys Ser Cys Arg Asp Gly
                      850                 855                 860

Glu Lys Cys Ala His His Ser His His Phe Ser Leu Asp Ile Asp Val
      865                 870                 875                 880

Gly Cys Thr Asp Leu His Glu Asn Leu Gly Val Trp Val Val Phe Lys
                      885                 890                 895

Ile Lys Thr Gln Glu Gly His Ala Arg Leu Gly Asn Leu Glu Phe Ile
                      900                 905                 910

Glu Glu Lys Pro Leu Leu Gly Glu Ala Leu Ser Arg Val Lys Arg Ala
                      915                 920                 925

Glu Lys Lys Trp Arg Asp Lys Arg Glu Lys Leu Gln Leu Glu Thr Lys
                      930                 935                 940

Arg Val Tyr Thr Glu Ala Lys Glu Ala Val Asp Ala Leu Phe Val Asp
      945                 950                 955                 960

Ser Gln Tyr Asp Arg Leu Gln Ala Asp Thr Asn Ile Gly Met Ile His
                      965                 970                 975

Ala Ala Asp Lys Leu Val His Arg Ile Arg Glu Ala Tyr Leu Ser Glu
                      980                 985                 990

Leu Pro Val Ile Pro Gly Val Asn Ala Glu Ile Phe Glu Glu Leu Glu
              995                 1000                1005

Gly His Ile Ile Thr Ala Ile Ser Leu Tyr Asp Ala Arg Asn Val
              1010                1015                1020
```

| | | | | | | | | | | |
|---|---|---|---|---|---|---|---|---|---|---|
|Val|Lys|Asn|Gly|Asp|Phe|Asn|Asn|Gly|Leu|Thr|Cys|Trp|Asn|Val|
| |1025| | | |1030| | | |1035| |

Val Lys Asn Gly Asp Phe Asn Asn Gly Leu Thr Cys Trp Asn Val
    1025                1030                1035

Lys Gly His Val Asp Val Gln Gln Ser His His Arg Ser Asp Leu
    1040                1045                1050

Val Ile Pro Glu Trp Glu Ala Glu Val Ser Gln Ala Val Arg Val
    1055                1060                1065

Cys Pro Gly Cys Gly Tyr Ile Leu Arg Val Thr Ala Tyr Lys Glu
    1070                1075                1080

Gly Tyr Gly Glu Gly Cys Val Thr Ile His Glu Ile Glu Asn Asn
    1085                1090                1095

Thr Asp Glu Leu Lys Phe Lys Asn Arg Glu Glu Glu Val Tyr
    1100                1105                1110

Pro Thr Asp Thr Gly Thr Cys Asn Asp Tyr Thr Ala His Gln Gly
    1115                1120                1125

Thr Ala Gly Cys Ala Asp Ala Cys Asn Ser Arg Asn Ala Gly Tyr
    1130                1135                1140

Glu Asp Ala Tyr Glu Val Asp Thr Thr Ala Ser Val Asn Tyr Lys
    1145                1150                1155

Pro Thr Tyr Glu Glu Glu Thr Tyr Thr Asp Val Arg Arg Asp Asn
    1160                1165                1170

His Cys Glu Tyr Asp Arg Gly Tyr Val Asn Tyr Pro Pro Val Pro
    1175                1180                1185

Ala Gly Tyr Val Thr Lys Glu Leu Glu Tyr Phe Pro Glu Thr Asp
    1190                1195                1200

Thr Val Trp Ile Glu Ile Gly Glu Thr Glu Gly Lys Phe Ile Val
    1205                1210                1215

Asp Ser Val Glu Leu Leu Leu Met Glu Glu
    1220                1225

<210> SEQ ID NO 4
<211> LENGTH: 1944
<212> TYPE: DNA
<213> ORGANISM: Artificial Sequence
<220> FEATURE:
<223> OTHER INFORMATION: T25-cry1Ba coding sequence

<400> SEQUENCE: 4

```
atggcgtcaa ataggaaaaa tgagaatgaa attataaatg ctgtatcgaa tcattccgca      60
caaatggatc tattaccaga tgctcgtatt gaggatagct tgtgtatagc cgaggggaac     120
aatatcgatc catttgttag cgcatcaaca gtccaaacgg gtattaacat agctggtaga     180
atactaggcg tattgggcgt accgtttgct ggacaactag ctagttttta tagttttctt     240
gttggtgaat tatggcccg cggcagagat cagtgggaaa ttttcctaga acatgtcgaa     300
caacttataa atcaacaaat aacagaaaat gctaggaata cggctcttgc tcgattacaa     360
ggtttaggag attccttcag agcctatcaa cagtcacttg aagattggct agaaaaccgt     420
gatgatgcaa gaacgagaag tgttctttat acccaatata tagctttaga acttgatttt     480
cttaatgcga tgccgctttt cgcaattaga accaagaag ttccattatt gatggtatat     540
gctcaagctg caaatttaca cctattatta ttgagagatg cctctctttt tggtagtgaa     600
tttgggctta catcgcagga aattcaacgc tattatgagc gccaagtgga acgaacgaga     660
gattattccg actattgcgt agaatggtat aatacaggtc taaatagctt gagagggaca     720
aatgccgcaa gttgggtacg gtataatcaa ttccgtagag atctaacgtt aggagtatta     780
```

```
gatctagtgg cactattccc aagctatgac actcgcactt atccaataaa tacgagtgct    840
cagttaacaa gagaagttta tacagacgca attggagcaa cagggtaaa tatggcaagt    900 atgaattggt ataataataa tgcaccttcg ttctctgcca tagaggctgc ggctatccga    960
agcccgcatc tacttgattt tctagaacaa cttacaattt ttagcgcttc atcacgatgg   1020
agtaatacta ggcatatgac ttattggcgg gggcacacga ttcaatctcg gccaatagga   1080
ggcggattaa atacctcaac gcatggggct accaatactt ctattaatcc tgtaacatta   1140
cggttcgcat ctcgagacgt ttataggact gaatcatatg caggagtgct tctatgggga   1200
atttaccttg aacctattca tggtgtccct actgttaggt ttaattttac gaaccctcag   1260
aatatttctg atagaggtac cgctaactat agtcaacctt atgagtcacc tgggcttcaa   1320
ttaaaagatt cagaaactga attaccacca gaaacaacag aacgaccaaa ttatgaatct   1380
tacagtcaca ggttatctca tataggtata attttacaat ccagggtgaa tgtaccggta   1440
tattcttgga cgcatcgtag tgcagatcgt acgaatacga ttggaccaaa tagaatcacc   1500
caaatcccaa tggtaaaagc atccgaactt cctcaaggta ccactgttgt tagaggacca   1560
ggatttactg gtggggatat tcttcgaaga acgaatactg gtggatttgg accgataaga   1620
gtaactgtta acgaccatt aacacaaaga tatcgtatag gattccgcta tgcttcaact   1680
gtagattttg atttctttgt atcacgtgga ggtactactg taaataattt tagattccta   1740
cgtacaatga acagtggaga cgaactaaaa tacgaaaatt ttgtgagacg tgcttttact   1800 acaccttta cttttacaca aattcaagat ataattcgaa cgtctattca aggccttagt   1860
ggaaatgggg aagtgtatat agataaaatt gaaattattc cagttactgc aaccttcgaa   1920
gcagaatatg atttagaaag ataa                                          1944

<210> SEQ ID NO 5
<211> LENGTH: 647
<212> TYPE: PRT
<213> ORGANISM: Artificial Sequence
<220> FEATURE:
<223> OTHER INFORMATION: T25-Cry1Ba toxin

<400> SEQUENCE: 5

Met Ala Ser Asn Arg Lys Asn Glu Asn Glu Ile Ile Asn Ala Val Ser
1               5                  10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160
```

-continued

```
Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Leu Asn Thr Ser Thr His
        355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575
```

-continued

```
Phe Arg Phe Leu Arg Thr Met Asn Ser Gly Asp Glu Leu Lys Tyr Gly
                580                 585                 590

Asn Phe Val Arg Arg Ala Phe Thr Thr Pro Phe Thr Phe Thr Gln Ile
            595                 600                 605

Gln Asp Ile Ile Arg Thr Ser Ile Gln Gly Leu Ser Gly Asn Gly Glu
        610                 615                 620

Val Tyr Ile Asp Lys Ile Glu Ile Ile Pro Val Thr Ala Thr Phe Glu
625                 630                 635                 640

Ala Glu Tyr Asp Leu Glu Arg
                645

<210> SEQ ID NO 6
<211> LENGTH: 647
<212> TYPE: PRT
<213> ORGANISM: Artificial Sequence
<220> FEATURE:
<223> OTHER INFORMATION: T25-eCry1Ba Y150 mutants
<220> FEATURE:
<221> NAME/KEY: MISC_FEATURE
<222> LOCATION: (2

```
Gln Arg Tyr Tyr Glu Arg Gln Val Glu Arg Thr Arg Asp Tyr Ser Asp
        210                 215                 220
Tyr Cys Val Glu Trp Tyr Asn Thr Gly Leu Asn Ser Leu Arg Gly Thr
225                 230                 235                 240
Asn Ala Ala Ser Trp Val Arg Tyr Asn Gln Phe Arg Arg Asp Leu Thr
                245                 250                 255
Leu Gly Val Leu Asp Leu Val Ala Leu Phe Pro Ser Tyr Asp Thr Arg
            260                 265                 270
Thr Tyr Pro Ile Asn Thr Ser Ala Gln Leu Thr Arg Glu Val Tyr Thr
        275                 280                 285
Asp Ala Ile Gly Ala Thr Gly Val Asn Met Ala Ser Met Asn Trp Tyr
290                 295                 300
Asn Asn Asn Ala Pro Ser Phe Ser Ala Ile Glu Ala Ala Ile Arg
305                 310                 315                 320
Ser Pro His Leu Leu Asp Phe Leu Glu Gln Leu Thr Ile Phe Ser Ala
                325                 330                 335
Ser Ser Arg Trp Ser Asn Thr Arg His Met Thr Tyr Trp Arg Gly His
            340                 345                 350
Thr Ile Gln Ser Arg Pro Ile Gly Gly Gly Leu Asn Thr Ser Thr His
        355                 360                 365
Gly Ala Thr Asn Thr Ser Ile Asn Pro Val Thr Leu Arg Phe Ala Ser
370                 375                 380
Arg Asp Val Tyr Arg Thr Glu Ser Tyr Ala Gly Val Leu Leu Trp Gly
385                 390                 395                 400
Ile Tyr Leu Glu Pro Ile His Gly Val Pro Thr Val Arg Phe Asn Phe
                405                 410                 415
Thr Asn Pro Gln Asn Ile Ser Asp Arg Gly Thr Ala Asn Tyr Ser Gln
            420                 425                 430
Pro Tyr Glu Ser Pro Gly Leu Gln Leu Lys Asp Ser Glu Thr Glu Leu
        435                 440                 445
Pro Pro Glu Thr Thr Glu Arg Pro Asn Tyr Glu Ser Tyr Ser His Arg
450                 455                 460
Leu Ser His Ile Gly Ile Ile Leu Gln Ser Arg Val Asn Val Pro Val
465                 470                 475                 480
Tyr Ser Trp Thr His Arg Ser Ala Asp Arg Thr Asn Thr Ile Gly Pro
                485                 490                 495
Asn Arg Ile Thr Gln Ile Pro Met Val Lys Ala Ser Glu Leu Pro Gln
            500                 505                 510
Gly Thr Thr Val Val Arg Gly Pro Gly Phe Thr Gly Gly Asp Ile Leu
        515                 520                 525
Arg Arg Thr Asn Thr Gly Gly Phe Gly Pro Ile Arg Val Thr Val Asn
530                 535                 540
Gly Pro Leu Thr Gln Arg Tyr Arg Ile Gly Phe Arg Tyr Ala Ser Thr
545                 550                 555                 560
Val Asp Phe Asp Phe Phe Val Ser Arg Gly Gly Thr Thr Val Asn Asn
                565                 570                 575
Phe Arg Phe Leu Arg Thr Met Asn Ser Gly Asp Glu Leu Lys Tyr Gly
            580                 585                 590
Asn Phe Val Arg Arg Ala Phe Thr Thr Pro Phe Thr Phe Thr Gln Ile
        595                 600                 605
Gln Asp Ile Ile Arg Thr Ser Ile Gln Gly Leu Ser Gly Asn Gly Glu
        610                 615                 620
```

```
Val Tyr Ile Asp Lys Ile Glu Ile Ile Pro Val Thr Ala Thr Phe Glu
625                 630                 635                 640

Ala Glu Tyr Asp Leu Glu Arg
                645
```

<210> SEQ ID NO 7
<211> LENGTH: 647
<212> TYPE: PRT
<213> ORGANISM: Artificial Sequence
<220> FEATURE:
<223> OTHER INFORMATION: eCry1Ba-T2AY150K

<400> SEQUENCE: 7

```
Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
                20                  25                  30

Ser Leu Cys Ile Ala Glu Gly Asn Asn Ile Asp Pro Phe Val Ser Ala
            35                  40                  45

Ser Thr Val Gln Thr Gly Ile Asn Ile Ala Gly Arg Ile Leu Gly Val
        50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
                100                 105                 110

Asn Thr Ala Leu Ala Arg Leu Gln Gly Leu Gly Asp Ser Phe Arg Ala
            115                 120                 125

Tyr Gln Gln Ser Leu Glu Asp Trp Leu Glu Asn Arg Asp Asp Ala Arg
        130                 135                 140

Thr Arg Ser Val Leu Lys Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
                180                 185                 190

Asp Ala Ser Leu Phe Gly Ser Glu Phe Gly Leu Thr Ser Gln Glu Ile
            195                 200                 205

Gln Arg Tyr Tyr Glu Arg Gln Val Glu Arg Thr Arg Asp Tyr Ser Asp
        210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
                260                 265                 270

Thr Tyr Pro Ile Asn Thr Ser Ala Gln Leu Thr Arg Glu Val Tyr Thr
            275                 280                 285

Asp Ala Ile Gly Ala Thr Gly Val Asn Met Ala Ser Met Asn Trp Tyr
        290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335
```

```
Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
            355                 360                 365

Gly Ala Thr Asn Thr Ser Ile Asn Pro Val Thr Leu Arg Phe Ala Ser
        370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
        595                 600                 605

Gln Asp Ile Ile Arg Thr Ser Ile Gln Gly Leu Ser Gly Asn Gly Glu
610                 615                 620

Val Tyr Ile Asp Lys Ile Glu Ile Pro Val Thr Ala Thr Phe Glu
625                 630                 635                 640

Ala Glu Tyr Asp Leu Glu Arg
            645
```

<210> SEQ ID NO 8
<211> LENGTH: 647
<212> TYPE: PRT
<213> ORGANISM: Artificial Sequence
<220> FEATURE:
<223> OTHER INFORMATION: eCry1Ba-T2AY150KM178S

<400> SEQUENCE: 8

```
Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45
```

```
Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
                115                 120                 125

Tyr Gln Gln Ser Leu Glu Asp Trp Leu Glu Asn Arg Asp Asp Ala Arg
    130                 135                 140

Thr Arg Ser Val Leu Lys Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Ser Val Tyr Ala Gln Ala Ala Asn Leu His Leu Leu Leu Leu Arg
                180                 185                 190

Asp Ala Ser Leu Phe Gly Ser Glu Phe Gly Leu Thr Ser Gln Glu Ile
            195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
                260                 265                 270

Thr Tyr Pro Ile Asn Thr Ser Ala Gln Leu Thr Arg Glu Val Tyr Thr
            275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
                340                 345                 350

Thr Ile Gln Ser Arg Pro Ile Gly Gly Gly Leu Asn Thr Ser Thr His
            355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
                420                 425                 430

Pro Tyr Glu Ser Pro Gly Leu Gln Leu Lys Asp Ser Glu Thr Glu Leu
            435                 440                 445

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
```

```
            465                 470                 475                 480
        Tyr Ser Trp Thr His Arg Ser Ala Asp Arg Thr Asn Thr Ile Gly Pro
                        485                 490                 495

Asn Arg Ile Thr Gln Ile Pro Met Val Lys Ala Ser Glu Leu Pro Gln
                        500                 505                 510

Gly Thr Thr Val Val Arg Gly Pro Gly Phe Thr Gly Asp Ile Leu
                        515                 520                 525

Arg Arg Thr Asn Thr Gly Gly Phe Gly Pro Ile Arg Val Thr Val Asn
        530                 535                 540

Gly Pro Leu Thr Gln Arg Tyr Arg Ile Gly Phe Arg Tyr Ala Ser Thr
        545                 550                 555                 560

Val Asp Phe Asp Phe Phe Val Ser Arg Gly Thr Thr Val Asn Asn
                        565                 570                 575

Phe Arg Phe Leu Arg Thr Met Asn Ser Gly Asp Glu Leu Lys Tyr Gly
                        580                 585                 590

Asn Phe Val Arg Arg Ala Phe Thr Thr Pro Phe Thr Phe Thr Gln Ile
                        595                 600                 605

Gln Asp Ile Ile Arg Thr Ser Ile Gln Gly Leu Ser Gly Asn Gly Glu
                        610                 615                 620

Val Tyr Ile Asp Lys Ile Glu Ile Ile Pro Val Thr Ala Thr Phe Glu
        625                 630                 635                 640

Ala Glu Tyr Asp Leu Glu Arg
                        645

<210> SEQ ID NO 9
<211> LENGTH: 647
<212> TYPE: PRT
<213> ORGANISM: Artificial Sequence
<220> FEATURE:
<223> OTHER INFORMATION: eCry1Ba-T2AY150KL189S

<400> SEQUENCE: 9

Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
                20                  25                  30

Ser Leu Cys Ile Ala Glu Gly Asn Asn Ile Asp Pro Phe Val Ser Ala
            35                  40                  45

Ser Thr Val Gln Thr Gly Ile Asn Ile Ala Gly Ar

-continued

```
                180                 185                 190
Asp Ala Ser Leu Phe Gly Ser Glu Phe Gly Leu Thr Ser Gln Glu Ile
            195                 200                 205

Gln Arg Tyr Tyr Glu Arg Gln Val Glu Arg Thr Arg Asp Tyr Ser Asp
210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
        355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
        595                 600                 605
```

-continued

Gln Asp Ile Ile Arg Thr Ser Ile Gln Gly Leu Ser Gly Asn Gly Glu
610                 615                 620

Val Tyr Ile Asp Lys Ile Glu Ile Pro Val Thr Ala Thr Phe Glu
625                 630                 635                 640

Ala Glu Tyr Asp Leu Glu Arg
                645

<210> SEQ ID NO 10
<211> LENGTH: 647
<212> TYPE: PRT
<213> ORGANISM: Artificial Sequence
<220> FEATURE:
<223> OTHER INFORMATION: eCry1Ba-T2AY150KS199K

<400> SEQUENCE: 10

Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
                20                  25                  30

Ser Leu Cys Ile Ala Glu Gly Asn Asn Ile Asp Pro Phe Val Ser Ala
            35                  40 45

Ser Thr Val Gln Thr Gly Ile Asn Ile Ala Gly Arg Ile Leu Gly Val
50 55 60

Leu Gly Val Pro Phe Ala Gly Gln Leu Ala Ser Phe Tyr Ser Phe Leu
65 70 75 80

Val Gly Glu Leu Trp Pro Arg Gly Arg Asp Gln Trp Glu Ile Phe Leu
85 90 95

Glu His Val Glu Gln Leu Ile Asn Gln Gln Ile Thr Glu Asn Ala Arg
100 105 110

Asn Thr Ala Leu Ala Arg Leu Gln Gly Leu Gly Asp Ser Phe Arg Ala
115 120 125

Tyr Gln Gln Ser Leu Glu Asp Trp Leu Glu Asn Arg Asp Asp Ala Arg
130 135 140

Thr Arg Ser Val Leu Lys Thr Gln Tyr Ile Ala Leu Glu Leu Asp Phe
145 150 155 160

Leu Asn Ala Met Pro Leu Phe Ala Ile Arg Asn Gln Glu Val Pro Leu
165 170 175

Leu Met Val Tyr Ala Gln Ala Ala Asn Leu His Leu Leu Leu Leu Arg
180 185 190

Asp Ala Ser Leu Phe Gly Lys Glu Phe Gly Leu Thr Ser Gln Glu Ile
195 200 205

Gln Arg Tyr Tyr Glu Arg Gln Val Glu Arg Thr Arg Asp Tyr Ser Asp
210 215 220

Tyr Cys Val Glu Trp Tyr Asn Thr Gly Leu Asn Ser Leu Arg Gly Thr
225 230 235 240

Asn Ala Ala Ser Trp Val Arg Tyr Asn Gln Phe Arg Arg Asp Leu Thr
245 250 255

Leu Gly Val Leu Asp Leu Val Ala Leu Phe Pro Ser Tyr Asp Thr Arg
260 265 270

Thr Tyr Pro Ile Asn Thr Ser Ala Gln Leu Thr Arg Glu Val Tyr Thr
275 280 285

Asp Ala Ile Gly Ala Thr Gly Val Asn Met Ala Ser Met Asn Trp Tyr
290 295 300

Asn Asn Asn Ala Pro Ser Phe Ser Ala Ile Glu Ala Ala Ala Ile Arg
305 310 315 320

-continued

Ser Pro His Leu Leu Asp Phe Leu Glu Gln Leu Thr Ile Phe Ser Ala
            325                 330                 335

Ser Ser Arg Trp Ser Asn Thr Arg His Met Thr Tyr Trp Arg Gly His
        340                 345                 350

Thr Ile Gln Ser Arg Pro Ile Gly Gly Gly Leu Asn Thr Ser Thr His
    355                 360                 365

Gly Ala Thr Asn Thr Ser Ile Asn Pro Val Thr Leu Arg Phe Ala Ser
370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
        595                 600                 605

Gln Asp Ile Ile Arg Thr Ser Ile Gln Gly Leu Ser Gly Asn Gly Glu
    610                 615                 620

Val Tyr Ile Asp Lys Ile Glu Ile Ile Pro Val Thr Ala Thr Phe Glu
625                 630                 635                 640

Ala Glu Tyr Asp Leu Glu Arg
                645

<210> SEQ ID NO 11
<211> LENGTH: 647
<212> TYPE: PRT
<213> ORGANISM: Artificial Sequence
<220> FEATURE:
<223> OTHER INFORMATION: Cry1Ba-TM21

<400> SEQUENCE: 11

Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

```
Ser Leu Cys Ile Ala Glu Gly Asn Asn Ile Asp Pro Phe Val Ser Ala
         35                  40                  45

Ser Thr Val Gln Thr Gly Ile Asn Ile Ala Gly Arg Ile Leu Gly Val
 50                  55                  60

Leu Gly Val Pro Phe Ala Gly Gln Leu Ala Ser Phe Tyr Ser Phe Leu
 65                  70                  75                  80

Trp Gly Glu Leu Trp Pro Arg Gly Arg Asp Gln Trp Glu Ile Phe Leu
                 85                  90                  95

Glu His Val Glu Gln Leu Ile Asn Gln Gln Ile Thr Glu Asn Ala Arg
                100                 105                 110

Asn Thr Ala Leu Ala Arg Leu Gln Gly Leu Gly Asp Ser Phe Arg Ala
                115                 120                 125

Tyr Gln Gln Ser Leu Glu Asp Trp Leu Glu Asn Arg Asp Asp Ala Arg
        130                 135                 140

Thr Arg Ser Val Leu Lys Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
                180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
        210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
                260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
        290                 295                 300

Asn Asn Asn Ala Pro Ser Phe Ser Ala Ile Glu Ala Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
        355                 360                 365

Gly Ala Thr Asn Thr Ser Ile Asn Pro Val Thr Leu Arg Phe Ala Ser
        370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
                420                 425                 430

Pro Tyr Glu Ser Pro Gly Leu Gln Leu Lys Asp Ser Glu Thr Glu Leu
        435                 440                 445
```

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
            485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Asp Ile Leu
            515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Val Ser Arg Gly Thr Thr Val Asn Asn
            565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
            595                 600                 605

Gln Asp Ile Ile Arg Thr Ser Ile Gln Gly Leu Ser Gly Asn Gly Glu
610                 615                 620

Val Tyr Ile Asp Lys Ile Glu Ile Ile Pro Val Thr Ala Thr Phe Glu
625                 630                 635                 640

Ala Glu Tyr Asp Leu Glu Arg
            645

<210> SEQ ID NO 12
<211> LENGTH: 647
<212> TYPE: PRT
<213> ORGANISM: Artificial Sequence
<220> FEATURE:
<223> OTHER INFORMATION: Cry1Ba-TM90

<400> SEQUENCE: 12

Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Leu Asn Ala Met Pro Leu Phe Ala Ile Arg Asn Gln Glu Val Pro Leu
                165                 170                 175

Leu Ser Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
        355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly

```
                580               585              590
Asn Phe Val Arg Arg Ala Phe Thr Thr Pro Phe Thr Phe Thr Gln Ile
                    595                 600                 605

Gln Asp Ile Ile Arg Thr Ser Ile Gln Gly Leu Ser Gly Asn Gly Glu
        610                 615                 620

Val Tyr Ile Asp Lys Ile Glu Ile Ile Pro Val Thr Ala Thr Phe Glu
625                 630                 635                 640

Ala Glu Tyr Asp Leu Glu Arg
                645

<210> SEQ ID NO 13
<211> LENGTH: 1944
<212> TYPE: DNA
<213> ORGANISM: Artificial Sequence
<220> FEATURE:
<223> OTHER INFORMATION: Maize-optimized sequence encoding eCry1Ba-T2A,
      Y150K,L189S mutant

<400> SEQUENCE: 13
```

| | | |
|---|---|---|
| atggcctcca accgcaagaa cgagaacgag atcatcaacg ccgtgagcaa ccacagcgcc | 60 |
| cagatggacc tgctgccgga cgccaggatc gaggactctc tgtgcatcgc cgagggcaac | 120 |
| aacatcgacc cgttcgtgag cgccagcacc gtgcagaccg gcatcaacat cgctggccgc | 180 |
| atcctgggcg tgctcggcgt gccattcgct gggcaactgg cctccttcta ctccttcctg | 240 |
| gtgggcgaac tgtggccaag gggcagggac cagtgggaga tcttcctcga gcacgtggag | 300 |
| cagctgatca ccagcagat caccgagaac gcccgcaaca ccgccctggc taggctgcag | 360 |
| gggctgggcg acagcttccg cgcctaccag cagagcctcg aggactggct cgagaacaga | 420 |
| gatgacgcca ggacccgcag cgtgctcaag acccagtaca tcgccctcga gctggacttc | 480 |
| ctgaacgcca tgccgctgtt cgccatccgc aaccaggaag tgccgctgct gatggtgtac | 540 |
| gcccaggccg ccaacctgca cctcagcctg ctgagggacg ccagcctgtt cggcagcgag | 600 |
| ttcggcctga ccagccagga atccagcgc tactacgagc ccaggtgga gaggaccccgc | 660 |
| gactacagcg actactgcgt ggagtggtac aataccggcc tgaacagcct gaggggcacc | 720 |
| aacgccgcca gctgggtgcg ctacaaccag ttcgccgcg acctgacgct cggcgtcctg | 780 |
| gacctggtgg ccctgttccc gagctacgac acccgcacct accgatcaa caccagcgct | 840 |
| cagctgaccc gcgaggtgta caccgacgcc atcggcgcca ccggcgtgaa catggccagc | 900 |
| atgaactggt acaacaacaa cgccccgagc ttcagcgcca tcgaggccgc tgccatcagg | 960 |
| tccccgcatc tgctcgattt tctcgagcag ctgaccatct tcagcgccag cagccgctgg | 1020 |
| tccaacaccc gccacatgac ctactggagg ggccacacca tccagagcag gccaatcggc | 1080 |
| ggcggcctga caccagcac ccacggcgcc accaacacca gcatcaaccc ggtgacgctg | 1140 |
| aggttcgcca gccgcgacgt gtaccgcacc gagagctacg ctggcgtgct gctgtgggc | 1200 |
| atctacctcg agccgatcca cggcgtgccg accgtgcgct tcaacttcac caacccgcag | 1260 |
| aacatcagcg accgcggcac cgccaactac agccagccgt acgagagccc aggcctgcag | 1320 |
| ctgaaggaca gcgagactga gctgccgccc gagactaccg agcgcccgaa ctacgagagc | 1380 |
| tacagccacc gcctgagcca catcggcatc atcctgcaga gccgcgtgaa cgtgccggtg | 1440 |
| tacagctgga cccacaggtc cgccgaccgg accaacacca tcggcccgaa ccgcatcacc | 1500 |
| cagatcccga tggtcaaggc cagcgagctg ccacagggta cgaccgtggt gaggggccca | 1560 |
| ggcttcactg gcggcgacat cctgcgccgc acgaacaccg gcggcttcgg cccaatccgc | 1620 |

| | | |
|---|---|---|
| gtgaccgtga acggcccgct gacccagagg tacaggatcg gcttccgcta cgcctccacc | | 1680 |
| gtggacttcg atttctttgt gagcaggggc ggcaccaccg tcaacaactt ccgcttcctg | | 1740 |
| cgcaccatga acagcggcga cgagctgaag tacggcaact tcgtgcgcag ggccttcacc | | 1800 |
| accccgttca ccttcacgca gatccaggac atcatccgca ccagcatcca gggcctgagc | | 1860 |
| ggcaacggcg aggtctacat cgacaagatc gagatcatcc cggtgaccgc caccttcgag | | 1920 |
| gccgagtacg acctcgagcg ctga | | 1944 |

```
<210> SEQ ID NO 14
<211> LENGTH: 40
<212> TYPE: DNA
<213> ORGANISM: Artificial Sequence
<220> FEATURE:
<223> OTHER INFORMATION: YG152 Forward primer
<220> FEATURE:
<221> NAME/KEY: misc_feature
<222> LOCATION: (13)..(13)
<223> OTHER INFORMATION: n=a, t, g or c
<220> FEATURE:
<221> NAME/KEY: misc_feature
<222> LOCATION: (14)..(14)
<223> OTHER INFORMATION: n=a, t, g or c
<220> FEATURE:
<221> NAME/KEY: misc_feature
<222> LOCATION: (15)..(15)
<223> OTHER INFORMATION: s=g or c

<400> SEQUENCE: 14
```

| | |
|---|---|
| agaagtgttc ttnnsaccca atatatagct ttagaacttg | 40 |

```
<210> SEQ ID NO 15
<211> LENGTH: 39
<212> TYPE: DNA
<213> ORGANISM: Artificial Sequence
<220> FEATURE:
<223> OTHER INFORMATION: YG153 reverse primer
<220> FEATURE:
<221> NAME/KEY: misc_feature
<222> LOCATION: (13)..(13)
<223> OTHER INFORMATION: s= g or c
<220> FEATURE:
<221> NAME/KEY: misc_feature
<222> LOCATION: (14)..(14)
<223> OTHER INFORMATION: x= a, t, g or c
<220> FEATURE:
<221> NAME/KEY: misc_feature
<222> LOCATION: (15)..(15)
<223> OTHER INFORMATION: x= a, t, g or c

<400> SEQUENCE: 15
```

| | |
|---|---|
| tatatattgg gtsnnaagaa cacttctcgt tcttgcatc | 39 |

```
<210> SEQ ID NO 16
<211> LENGTH: 40
<212> TYPE: DNA
<213> ORGANISM: Artificial Sequence
<220> FEATURE:
<223> OTHER INFORMATION: YG154 forward primer

<400> SEQUENCE: 16
```

| | |
|---|---|
| agaagtgttc ttaagaccca atatatagct ttagaacttg | 40 |

```
<210> SEQ ID NO 17
<211> LENGTH: 39
<212> TYPE: DNA
<213> ORGANISM: Artificial Sequence
<220> FEATURE:
<223> OTHER INFORMATION: YG155 reverse primer
```

```
<400> SEQUENCE: 17
tatatattgg gtcttaagaa cacttctcgt tcttgcatc                              39

<210> SEQ ID NO 18
<211> LENGTH: 40
<212> TYPE: DNA
<213> ORGANISM: Artificial Sequence
<220> FEATURE:
<223> OTHER INFORMATION: YG156 forward primer

<400> SEQUENCE: 18
agaagtgttc tttggaccca atatatagct ttagaacttg                             40

<210> SEQ ID NO 19
<211> LENGTH: 39
<212> TYPE: DNA
<213> ORGANISM: Artificial Sequence
<220> FEATURE:
<223> OTHER INFORMATION: YG157 reverse primer

<400> SEQUENCE: 19
tatatattgg gtccaaagaa cacttctcgt tcttgcatc                              39

<210> SEQ ID NO 20
<211> LENGTH: 42
<212> TYPE: DNA
<213> ORGANISM: Artificial Sequence
<220> FEATURE:
<223> OTHER INFORMATION: YG160 forward primer

<400> SEQUENCE: 20
atatgtttaa acatgacttc aaataggaaa aatgagaatg aa                          42

<210> SEQ ID NO 21
<211> LENGTH: 40
<212> TYPE: DNA
<213> ORGANISM: Artificial Sequence
<220> FEATURE:
<223> OTHER INFORMATION: YG161 forward primer

<400> SEQUENCE: 21
atatgtttaa acatggatct attaccagat gctcgtattg                             40

<210> SEQ ID NO 22
<211> LENGTH: 43
<212> TYPE: DNA
<213> ORGANISM: Artificial Sequence
<220> FEATURE:
<223> OTHER INFORMATION: YG162 reverse primer

<400> SEQUENCE: 22
atatggcgcg cctatctttc taaatcatat tctgcttcga agg                         43

<210> SEQ ID NO 23
<211> LENGTH: 47
<212> TYPE: DNA
<213> ORGANISM: Artificial Sequence
<220> FEATURE:
<223> OTHER INFORMATION: YG163 forward primer

<400> SEQUENCE: 23
aattccatgg cgtcaaatag gaaaaatgag aatgaaatta taaatgc                     47

<210> SEQ ID NO 24
```

<211> LENGTH: 34
<212> TYPE: DNA
<213> ORGANISM: Artificial Sequence
<220> FEATURE:
<223> OTHER INFORMATION: YG164 forward primer

<400> SEQUENCE: 24
aattccatgg atctattacc agatgctcgt attg                       34

<210> SEQ ID NO 25
<211> LENGTH: 34
<212> TYPE: DNA
<213> ORGANISM: Artificial Sequence
<220> FEATURE:
<223> OTHER INFORMATION: YG165 primer

<400> SEQUENCE: 25
aattccatgg aggatagctt gtgtatagcc gagg                       34

<210> SEQ ID NO 26
<211> LENGTH: 42
<212> TYPE: DNA
<213> ORGANISM: Artificial Sequence
<220> FEATURE:
<223> OTHER INFORMATION: YG166 primer

<400> SEQUENCE: 26
aattgagctc ttatctttct aaatcatatt ctgcttcgaa gg              42

<210> SEQ ID NO 27
<211> LENGTH: 30
<212> TYPE: DNA
<213> ORGANISM: Artificial Sequence
<220> FEATURE:
<223> OTHER INFORMATION: YG171 primer

<400> SEQUENCE: 27
agttttcttt ggggtgaatt atggccccgc                            30

<210> SEQ ID NO 28
<211> LENGTH: 33
<212> TYPE: DNA
<213> ORGANISM: Artificial Sequence
<220> FEATURE:
<223> OTHER INFORMATION: YG172 primer

<400> SEQUENCE: 28
taattcaccc caaagaaaac tataaaaact agc                        33

<210> SEQ ID NO 29
<211> LENGTH: 34
<212> TYPE: DNA
<213> ORGANISM: Artificial Sequence
<220> FEATURE:
<223> OTHER INFORMATION: YG175 primer

<400> SEQUENCE: 29
caatatatag atttagaact tgattttctt aatg                       34

<210> SEQ ID NO 30
<211> LENGTH: 33
<212> TYPE: DNA
<213> ORGANISM: Artificial Sequence
<220> FEATURE:
<223> OTHER INFORMATION: YG176 primer

<400> SEQUENCE: 30
aagttctaaa tctatatatt gggtataaag aac                                33

<210> SEQ ID NO 31
<211> LENGTH: 31
<212> TYPE: DNA
<213> ORGANISM: Artificial Sequence
<220> FEATURE:
<223> OTHER INFORMATION: YG179 primer

<400> SEQUENCE: 31
ttacacctat ccttattgag agatgcctct c                                  31

<210> SEQ ID NO 32
<211> LENGTH: 33
<212> TYPE: DNA
<213> ORGANISM: Artificial Sequence
<220> FEATURE:
<223> OTHER INFORMATION: YG180 primer

<400> SEQUENCE: 32
tctcaataag gataggtgta aatttgcagc ttg                                33

<210> SEQ ID NO 33
<211> LENGTH: 35
<212> TYPE: DNA
<213> ORGANISM: Artificial Sequence
<220> FEATURE:
<223> OTHER INFORMATION: YG183 forward primer

<400> SEQUENCE: 33
agaacgagaa gtgaacttaa gacccaatat atagc                              35

<210> SEQ ID NO 34
<211> LENGTH: 39
<212> TYPE: DNA
<213> ORGANISM: Artificial Sequence
<220> FEATURE:
<223> OTHER INFORMATION: YG184 primer

<400> SEQUENCE: 34
acccaatata tagatttaga acttgattt cttaatgcg                          39

<210> SEQ ID NO 35
<211> LENGTH: 35
<212> TYPE: DNA
<213> ORGANISM: Artificial Sequence
<220> FEATURE:
<223> OTHER INFORMATION: YG186 primer

<400> SEQUENCE: 35
gaagttccat tattgccggt atatgctcaa gctgc                              35

<210> SEQ ID NO 36
<211> LENGTH: 37
<212> TYPE: DNA
<213> ORGANISM: Artificial Sequence
<220> FEATURE:
<223> OTHER INFORMATION: YG188 forward primer

<400> SEQUENCE: 36
tttcttaata agatgccgct tttcgcaatt agaaacc                            37

<210> SEQ ID NO 37
<211> LENGTH: 47
<212> TYPE: DNA

<213> ORGANISM: Artificial Sequence
<220> FEATURE:
<223> OTHER INFORMATION: YG189 primer

<400> SEQUENCE: 37
aagcggcatc ttattaagaa aatcaagttc taaagctata tattggg        47

<210> SEQ ID NO 38
<211> LENGTH: 34
<212> TYPE: DNA
<213> ORGANISM: Artificial Sequence
<220> FEATURE:
<223> OTHER INFORMATION: YG189 primer

<400> SEQUENCE: 38 cttttggta aggaatttgg gcttacatcg cagg        34

<210> SEQ ID NO 39
<211> LENGTH: 37
<212> TYPE: DNA
<213> ORGANISM: Artificial Sequence
<220> FEATURE:
<223> OTHER INFORMATION: YG191 primer

<400> SEQUENCE: 39
cccaaattcc ttaccaaaaa gagaggcatc tctcaat        37

<210> SEQ ID NO 40
<211> LENGTH: 40
<212> TYPE: DNA
<213> ORGANISM: Artificial Sequence
<220> FEATURE:
<223> OTHER INFORMATION: YG192 primer

<400> SEQUENCE: 40
ccattattga gcgtatatgc tcaagctgca aatttacacc        40

<210> SEQ ID NO 41
<211> LENGTH: 43
<212> TYPE: DNA
<213> ORGANISM: Artificial Sequence
<220> FEATURE:
<223> OTHER INFORMATION: YG193 reverse primer

<400> SEQUENCE: 41
agcatatacg ctcaataatg gaacttcttg gtttctaatt gcg        43

<210> SEQ ID NO 42
<211> LENGTH: 626
<212> TYPE: PRT
<213> ORGANISM: Bacillus thuringiensis
<220> FEATURE:
<221> NAME/KEY: MISC_FEATURE
<222> LOCATION: (1)..(626)
<223> OTHER INFORMATION: Truncated Cry1Ba-T7

<400> SEQUENCE: 42

Met Asp Leu Leu Pro Asp Ala Arg Ile Glu Asp Ser Leu Cys Ile Ala
1               5                   10                  15

Glu Gly Asn Asn Ile Asp Pro Phe Val Ser Ala Ser Thr Val Gln Thr
            20                  25                  30

Gly Ile Asn Ile Ala Gly Arg Ile Leu Gly Val Leu Gly Val Pro Phe
        35                  40                  45

Ala Gly Gln Leu Ala Ser Phe Tyr Ser Phe Leu Val Gly Glu Leu Trp
    50                  55                  60

```
Pro Arg Gly Arg Asp Gln Trp Glu Ile Phe Leu Glu His Val Glu Gln
 65                  70                  75                  80

Leu Ile Asn Gln Gln Ile Thr Glu Asn Ala Arg Asn Thr Ala Leu Ala
                 85                  90                  95

Arg Leu Gln Gly Leu Gly Asp Ser Phe Arg Ala Tyr Gln Gln Ser Leu
            100                 105                 110

Glu Asp Trp Leu Glu Asn Arg Asp Asp Ala Arg Thr Arg Ser Val Leu
            115                 120                 125

Tyr Thr Gln Tyr Ile Ala Leu Glu Leu Asp Phe Leu Asn Ala Met Pro
            130                 135                 140

Leu Phe Ala Ile Arg Asn Gln Glu Val Pro Leu Leu Met Val Tyr Ala
145                 150                 155                 160

Gln Ala Ala Asn Leu His Leu Leu Leu Arg Asp Ala Ser Leu Phe
                165                 170                 175

Gly Ser Glu Phe Gly Leu Thr Ser Gln Glu Ile Gln Arg Tyr Tyr Glu
            180                 185                 190

Arg Gln Val Glu Arg Thr Arg Asp Tyr Ser Asp Tyr Cys Val Glu Trp
            195                 200                 205

Tyr Asn Thr Gly Leu Asn Ser Leu Arg Gly Thr Asn Ala Ala Ser Trp
            210                 215                 220

Val Arg Tyr Asn Gln Phe Arg Arg Asp Leu Thr Leu Gly Val Leu Asp
225                 230                 235                 240

Leu Val Ala Leu Phe Pro Ser Tyr Asp Thr Arg Thr Tyr Pro Ile Asn
                245                 250                 255

Thr Ser Ala Gln Leu Thr Arg Glu Val Tyr Thr Asp Ala Ile Gly Ala
            260                 265                 270

Thr Gly Val Asn Met Ala Ser Met Asn Trp Tyr Asn Asn Asn Ala Pro
            275                 280                 285

Ser Phe Ser Ala Ile Glu Ala Ala Ile Arg Ser Pro His Leu Leu
            290                 295                 300

Asp Phe Leu Glu Gln Leu Thr Ile Phe Ser Ala Ser Ser Arg Trp Ser
305                 310                 315                 320

Asn Thr Arg His Met Thr Tyr Trp Arg Gly His Thr Ile Gln Ser Arg
                325                 330                 335

Pro Ile Gly Gly Gly Leu Asn Thr Ser Thr His Gly Ala Thr Asn Thr
            340                 345                 350

Ser Ile Asn Pro Val Thr Leu Arg Phe Ala Ser Arg Asp Val Tyr Arg
            355                 360                 365

Thr Glu Ser Tyr Ala Gly Val Leu Leu Trp Gly Ile Tyr Leu Glu Pro
            370                 375                 380

Ile His Gly Val Pro Thr Val Arg Phe Asn Phe Thr Asn Pro Gln Asn
385                 390                 395                 400

Ile Ser Asp Arg Gly Thr Ala Asn Tyr Ser Gln Pro Tyr Glu Ser Pro
                405                 410                 415

Gly Leu Gln Leu Lys Asp Ser Glu Thr Glu Leu Pro Pro Glu Thr Thr
            420                 425                 430

Glu Arg Pro Asn Tyr Glu Ser Tyr Ser His Arg Leu Ser His Ile Gly
            435                 440                 445

Ile Ile Leu Gln Ser Arg Val Asn Val Pro Val Tyr Ser Trp Thr His
            450                 455                 460

Arg Ser Ala Asp Arg Thr Asn Thr Ile Gly Pro Asn Arg Ile Thr Gln
465                 470                 475                 480
```

Ile Pro Met Val Lys Ala Ser Glu Leu Pro Gln Gly Thr Thr Val Val
            485                 490                 495

Arg Gly Pro Gly Phe Thr Gly Gly Asp Ile Leu Arg Arg Thr Asn Thr
            500                 505                 510

Gly Gly Phe Gly Pro Ile Arg Val Thr Val Asn Gly Pro Leu Thr Gln
            515                 520                 525

Arg Tyr Arg Ile Gly Phe Arg Tyr Ala Ser Thr Val Asp Phe Asp Phe
            530                 535                 540

Phe Val Ser Arg Gly Thr Thr Val Asn Asn Phe Arg Phe Leu Arg
545                 550                 555                 560

Thr Met Asn Ser Gly Asp Glu Leu Lys Tyr Gly Asn Phe Val Arg Arg
            565                 570                 575

Ala Phe Thr Thr Pro Phe Thr Phe Thr Gln Ile Gln Asp Ile Ile Arg
            580                 585                 590

Thr Ser Ile Gln Gly Leu Ser Gly Asn Gly Glu Val Tyr Ile Asp Lys
            595                 600                 605

Ile Glu Ile Ile Pro Val Thr Ala Thr Phe Glu Ala Glu Tyr Asp Leu
            610                 615                 620

Glu Arg
625

<210> SEQ ID NO 43
<211> LENGTH: 647
<212> TYPE: PRT
<213> ORGANISM: Artificial Sequence
<220> FEATURE:
<223> OTHER INFORMATION: Variant Cry1Ba-TM69

<400> SEQUENCE: 43

Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Lys Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Pro Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

-continued

Gln Arg Tyr Tyr Glu Arg Gln Val Glu Arg Thr Arg Asp Tyr Ser Asp
     210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
             245                 250                 255

Leu Gly Val Leu Asp Leu Val Ala Leu Phe Pro Ser Tyr Asp Thr Arg
         260                 265                 270

Thr Tyr Pro Ile Asn Thr Ser Ala Gln Leu Thr Arg Glu Val Tyr Thr
     275                 280                 285

Asp Ala Ile Gly Ala Thr Gly Val Asn Met Ala Ser Met Asn Trp Tyr
290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
             325                 330                 335

Ser Ser Arg Trp Ser Asn Thr Arg His Met Thr Tyr Trp Arg Gly His
         340                 345                 350

Thr Ile Gln Ser Arg Pro Ile Gly Gly Gly Leu Asn Thr Ser Thr His
     355                 360                 365

Gly Ala Thr Asn Thr Ser Ile Asn Pro Val Thr Leu Arg Phe Ala Ser
370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
             405                 410                 415

Thr Asn Pro Gln Asn Ile Ser Asp Arg Gly Thr Ala Asn Tyr Ser Gln
         420                 425                 430

Pro Tyr Glu Ser Pro Gly Leu Gln Leu Lys Asp Ser Glu Thr Glu Leu
     435                 440                 445

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
             485                 490                 495

Asn Arg Ile Thr Gln Ile Pro Met Val Lys Ala Ser Glu Leu Pro Gln
         500                 505                 510

Gly Thr Thr Val Val Arg Gly Pro Gly Phe Thr Gly Gly Asp Ile Leu
     515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
             565                 570                 575

Phe Arg Phe Leu Arg Thr Met Asn Ser Gly Asp Glu Leu Lys Tyr Gly
         580                 585                 590

Asn Phe Val Arg Arg Ala Phe Thr Thr Pro Phe Thr Phe Thr Gln Ile
     595                 600                 605

Gln Asp Ile Ile Arg Thr Ser Ile Gln Gly Leu Ser Gly Asn Gly Glu
610                 615                 620

Val Tyr Ile Asp Lys Ile Glu Ile Ile Pro Val Thr Ala Thr Phe Glu

Ala Glu Tyr Asp Leu Glu Arg
                645

<210> SEQ ID NO 44
<211> LENGTH: 647
<212> TYPE: PRT
<213> ORGANISM: Artificial Sequence
<220> FEATURE:
<223> OTHER INFORMATION: Variant Cry1Ba-TM61

<400> SEQUENCE: 44

Met Ala Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Lys Thr Gln Tyr Ile Ala Leu Glu Leu Asp Phe
145                 150                 155                 160

Leu Asn Ala Met Pro Leu Phe Ala Ile Ser Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His

```
                    340                 345                 350
Thr Ile Gln Ser Arg Pro Ile Gly Gly Gly Leu Asn Thr Ser Thr His
                355                 360                 365
Gly Ala Thr Asn Thr Ser Ile Asn Pro Val Thr Leu Arg Phe Ala Ser
            370                 375                 380
Arg Asp Val Tyr Arg Thr Glu Ser Tyr Ala Gly Val Leu Leu Trp Gly
385                 390                 395                 400
Ile Tyr Leu Glu Pro Ile His Gly Val Pro Thr Val Arg Phe Asn Phe
                405                 410                 415
Thr Asn Pro Gln Asn Ile Ser Asp Arg Gly Thr Ala Asn Tyr Ser Gln
            420                 425                 430
Pro Tyr Glu Ser Pro Gly Leu Gln Leu Lys Asp Ser Glu Thr Glu Leu
        435                 440                 445
Pro Pro Glu Thr Thr Glu Arg Pro Asn Tyr Glu Ser Tyr Ser His Arg
    450                 455                 460
Leu Ser His Ile Gly Ile Ile Leu Gln Ser Arg Val Asn Val Pro Val
465                 470                 475                 480
Tyr Ser Trp Thr His Arg Ser Ala Asp Arg Thr Asn Thr Ile Gly Pro
                485                 490                 495
Asn Arg Ile Thr Gln Ile Pro Met Val Lys Ala Ser Glu Leu Pro Gln
            500                 505                 510
Gly Thr Thr Val Val Arg Gly Pro Gly Phe Thr Gly Gly Asp Ile Leu
        515                 520                 525
Arg Arg Thr Asn Thr Gly Gly Phe Gly Pro Ile Arg Val Thr Val Asn
    530                 535                 540
Gly Pro Leu Thr Gln Arg Tyr Arg Ile Gly Phe Arg Tyr Ala Ser Thr
545                 550                 555                 560
Val Asp Phe Asp Phe Phe Val Ser Arg Gly Gly Thr Thr Val Asn Asn
                565                 570                 575
Phe Arg Phe Leu Arg Thr Met Asn Ser Gly Asp Glu Leu Lys Tyr Gly
            580                 585                 590
Asn Phe Val Arg Arg Ala Phe Thr Thr Pro Phe Thr Phe Thr Gln Ile
        595                 600                 605
Gln Asp Ile Ile Arg Thr Ser Ile Gln Gly Leu Ser Gly Asn Gly Glu
    610                 615                 620
Val Tyr Ile Asp Lys Ile Glu Ile Ile Pro Val Thr Ala Thr Phe Glu
625                 630                 635                 640
Ala Glu Tyr Asp Leu Glu Arg
                645

<210> SEQ ID NO 45
<211> LENGTH: 1228
<212> TYPE: PRT
<213> ORGANISM: Bacillus thuringiensis

<400> SEQUENCE: 45

Met Thr Ser Asn Arg Lys Asn Glu Asn Glu Ile Ile Asn Ala Val Ser
1               5                   10                  15
Asn His Ser Ala Gln Met Asp Leu Leu Pro Asp Ala Arg Ile Glu Asp
            20                  25                  30
Ser Leu Cys Ile Ala Glu Gly Asn Asn Ile Asp Pro Phe Val Ser Ala
        35                  40                  45
Ser Thr Val Gln Thr Gly Ile Asn Ile Ala Gly Arg Ile Leu Gly Val
    50                  55                  60
```

-continued

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
            115                 120                 125

Tyr Gln Gln Ser Leu Glu Asp Trp Leu Glu Asn Arg Asp Ala Arg
        130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Arg
            180                 185                 190

Asp Ala Ser Leu Phe Gly Ser Glu Phe Gly Leu Thr Ser Gln Glu Ile
            195                 200                 205

Gln Arg Tyr Tyr Glu Arg Gln Val Glu Arg Thr Arg Asp Tyr Ser Asp
        210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
            275                 280                 285

Asp Ala Ile Gly Ala Thr Gly Val Asn Met Ala Ser Met Asn Trp Tyr
        290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Leu Asn Thr Ser Thr His
        355                 360                 365

Gly Ala Thr Asn Thr Ser Ile Asn Pro Val Thr Leu Arg Phe Ala Ser
370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro

```
                485                 490                 495
Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
            515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Val Ser Arg Gly Thr Thr Val Asn Asn
            565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
            595                 600                 605

Gln Asp Ile Ile Arg Thr Ser Ile Gln Gly Leu Ser Gly Asn Gly Glu
            610                 615                 620

Val Tyr Ile Asp Lys Ile Glu Ile Ile Pro Val Thr Ala Thr Phe Glu
625                 630                 635                 640

Ala Glu Tyr Asp Leu Glu Arg Ala Gln Glu Ala Val Asn Ala Leu Phe
                645                 650                 655

Thr Asn Thr Asn Pro Arg Arg Leu Lys Thr Asp Val Thr Asp Tyr His
                660                 665                 670

Ile Asp Gln Val Ser Asn Leu Val Ala Cys Leu Ser Asp Glu Phe Cys
            675                 680                 685

Leu Asp Glu Lys Arg Glu Leu Leu Glu Lys Val Lys Tyr Ala Lys Arg
690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
                740                 745                 750

Thr Ile Gln Glu Gly Asn Asp Val Phe Lys Glu Asn Tyr Val Thr Leu
            755                 760                 765

Pro Gly Thr Phe Asn Glu Cys Tyr Pro Thr Tyr Leu Tyr Gln Lys Ile
            770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
            820                 825                 830

Ser Val Glu Ser Pro Ile Gly Arg Cys Gly Glu Pro Asn Arg Cys Ala
            835                 840                 845

Pro His Phe Glu Trp Asn Pro Asp Leu Asp Cys Ser Cys Arg Asp Gly
            850                 855                 860

Glu Lys Cys Ala His His Ser His His Phe Ser Leu Asp Ile Asp Val
865                 870                 875                 880

Gly Cys Thr Asp Leu His Glu Asn Leu Gly Val Trp Val Val Phe Lys
                885                 890                 895

Ile Lys Thr Gln Glu Gly His Ala Arg Leu Gly Asn Leu Glu Phe Ile
            900                 905                 910
```

```
Glu Glu Lys Pro Leu Gly Glu Ala Leu Ser Arg Val Lys Arg Ala
            915                 920                 925

Glu Lys Lys Trp Arg Asp Lys Arg Glu Lys Leu Gln Leu Glu Thr Lys
    930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
            965                 970                 975

Ala Ala Asp Lys Leu Val His Arg Ile Arg Glu Ala Tyr Leu Ser Glu
        980                 985                 990

Leu Pro Val Ile Pro Gly Val Asn  Ala Glu Ile Phe Glu  Glu Leu Glu
            995                 1000                1005

Gly His  Ile Ile Thr Ala Ile  Ser Leu Tyr Asp Ala  Arg Asn Val
    1010                1015                1020

Val Lys  Asn Gly Asp Phe Asn  Asn Gly Leu Thr Cys  Trp Asn Val
    1025                1030                1035

Lys Gly His Val Asp Val Gln  Gln Ser His His Arg  Ser Asp Leu
    1040                1045                1050

Val Ile  Pro Glu Trp Glu Ala  Glu Val Ser Gln Ala  Val Arg Val
    1055                1060                1065

Cys Pro  Gly Cys Gly Tyr Ile  Leu Arg Val Thr Ala  Tyr Lys Glu
    1070                1075                1080

Gly Tyr  Gly Glu Gly Cys Val  Thr Ile His Glu Ile  Glu Asn Asn
    1085                1090                1095

Thr Asp  Glu Leu Lys Phe Lys  Asn Arg Glu Glu Glu  Glu Val Tyr
    1100                1105                1110

Pro Thr  Asp Thr Gly Thr Cys  Asn Asp Tyr Thr Ala  His Gln Gly
    1115                1120                1125

Thr Ala  Gly Cys Ala Asp Ala  Cys Asn Ser Arg Asn  Ala Gly Tyr
    1130                1135                1140

Glu Asp  Ala Tyr Glu Val Asp  Thr Thr Ala Ser Val  Asn Tyr Lys
    1145                1150                1155

Pro Thr  Tyr Glu Glu Glu Thr  Tyr Thr Asp Val Arg  Arg Asp Asn
    1160                1165                1170

His Cys  Glu Tyr Asp Arg Gly  Tyr Val Asn Tyr Pro  Pro Val Pro
    1175                1180                1185

Ala Gly  Tyr Val Thr Lys Glu  Leu Glu Tyr Phe Pro  Glu Thr Asp
    1190                1195                1200

Thr Val  Trp Ile Glu Ile Gly  Glu Thr Glu Gly Lys  Phe Ile Val
    1205                1210                1215

Asp Ser  Val Glu Leu Leu Leu  Met Glu Glu
    1220                1225

<210> SEQ ID NO 46
<211> LENGTH: 1228
<212> TYPE: PRT
<213> ORGANISM: Bacillus thuringiensis

<400> SEQUENCE: 46

Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
```

```
               35                  40                  45
Ser Thr Val Gln Thr Gly Ile Asn Ile Ala Gly Arg Ile Leu Gly Val
 50                  55                  60

Leu Gly Val Pro Phe Ala Gly Gln Leu Ala Ser Phe Tyr Ser Phe Leu
 65                  70                  75                  80

Val Gly Glu Leu Trp Pro Arg Gly Arg Asp Gln Trp Glu Ile Phe Leu
                 85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
            115                 120                 125

Tyr Gln Gln Ser Leu Glu Asp Trp Leu Glu Asn Arg Asp Asp Ala Arg
130                 135                 140

Thr Arg Ser Val Leu His Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
            195                 200                 205

Gln Arg Tyr Tyr Glu Arg Gln Val Glu Arg Thr Arg Asp Tyr Ser Asp
210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
            275                 280                 285

Asp Ala Ile Gly Ala Thr Gly Val Asn Met Ala Ser Met Asn Trp Tyr
290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
            355                 360                 365

Gly Ala Thr Asn Thr Ser Ile Asn Pro Val Thr Leu Arg Phe Ala Ser
370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
            435                 440                 445

Pro Pro Glu Thr Thr Glu Arg Pro Asn Tyr Glu Ser Tyr Ser His Arg
450                 455                 460
```

-continued

```
Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                    485                 490                 495

Asn Arg Ile Thr Gln Ile Pro Met Val Lys Ala Ser Glu Leu Pro Gln
                500                 505                 510

Gly Thr Thr Val Val Arg Gly Pro Gly Phe Thr Gly Gly Asp Ile Leu
                515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
                580                 585                 590

Asn Phe Val Arg Arg Ala Phe Thr Thr Pro Phe Thr Phe Thr Gln Ile
                595                 600                 605

Gln Asp Ile Ile Arg Thr Ser Ile Gln Gly Leu Ser Gly Asn Gly Glu
                610                 615                 620

Val Tyr Ile Asp Lys Ile Glu Ile Ile Pro Val Thr Ala Thr Phe Glu
625                 630                 635                 640

Ala Glu Tyr Asp Leu Glu Arg Ala Gln Glu Ala Val Asn Ala Leu Phe
                    645                 650                 655

Thr Asn Thr Asn Pro Arg Arg Leu Lys Thr Asp Val Thr Asp Tyr His
                660                 665                 670

Ile Asp Gln Val Ser Asn Leu Val Ala Cys Leu Ser Asp Glu Phe Cys
                675                 680                 685

Leu Asp Glu Lys Arg Glu Leu Leu Glu Lys Val Lys Tyr Ala Lys Arg
690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
                740                 745                 750

Thr Ile Gln Glu Gly Asn Asp Val Phe Lys Glu Asn Tyr Val Thr Leu
                755                 760                 765

Pro Gly Thr Phe Asn Glu Cys Tyr Pro Thr Tyr Leu Tyr Gln Lys Ile
                770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
                820                 825                 830

Ser Val Glu Ser Pro Ile Gly Arg Cys Gly Glu Pro Asn Arg Cys Ala
                835                 840                 845

Pro His Phe Glu Trp Asn Pro Asp Leu Asp Cys Ser Cys Arg Asp Gly
                850                 855                 860

Glu Lys Cys Ala His His Ser His His Phe Ser Leu Asp Ile Asp Val
865                 870                 875                 880
```

Gly Cys Thr Asp Leu His Glu Asn Leu Gly Val Trp Val Val Phe Lys
            885                 890                 895

Ile Lys Thr Gln Glu Gly His Ala Arg Leu Gly Asn Leu Glu Phe Ile
        900                 905                 910

Glu Glu Lys Pro Leu Leu Gly Glu Ala Leu Ser Arg Val Lys Arg Ala
    915                 920                 925

Glu Lys Lys Trp Arg Asp Lys Arg Glu Lys Leu Gln Leu Glu Thr Lys
930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
            965                 970                 975

Ala Ala Asp Lys Leu Val His Arg Ile Arg Glu Ala Tyr Leu Ser Glu
        980                 985                 990

Leu Pro Val Ile Pro Gly Val Asn Ala Glu Ile Phe Glu Glu Leu Glu
    995                 1000                1005

Gly His Ile Ile Thr Ala Ile Ser Leu Tyr Asp Ala Arg Asn Val
    1010                1015                1020

Val Lys Asn Gly Asp Phe Asn Asn Gly Leu Thr Cys Trp Asn Val
    1025                1030                1035

Lys Gly His Val Asp Val Gln Gln Ser His His Arg Ser Asp Leu
    1040                1045                1050

Val Ile Pro Glu Trp Glu Ala Glu Val Ser Gln Ala Val Arg Val
    1055                1060                1065

Cys Pro Gly Cys Gly Tyr Ile Leu Arg Val Thr Ala Tyr Lys Glu
    1070                1075                1080

Gly Tyr Gly Glu Gly Cys Val Thr Ile His Glu Ile Glu Asn Asn
    1085                1090                1095

Thr Asp Glu Leu Lys Phe Lys Asn Arg Glu Glu Glu Val Tyr
    1100                1105                1110

Pro Thr Asp Thr Gly Thr Cys Asn Asp Tyr Thr Ala His Gln Gly
    1115                1120                1125

Thr Ala Gly Cys Ala Asp Ala Cys Asn Ser Arg Asn Ala Gly Tyr
    1130                1135                1140

Glu Asp Ala Tyr Glu Val Asp Thr Thr Ala Ser Val Asn Tyr Lys
    1145                1150                1155

Pro Thr Tyr Glu Glu Glu Thr Tyr Thr Asp Val Arg Arg Asp Asn
    1160                1165                1170

His Cys Glu Tyr Asp Arg Gly Tyr Val Asn Tyr Pro Pro Val Pro
    1175                1180                1185

Ala Gly Tyr Val Thr Lys Glu Leu Glu Tyr Phe Pro Glu Thr Asp
    1190                1195                1200

Thr Val Trp Ile Glu Ile Gly Glu Thr Glu Gly Lys Phe Ile Val
    1205                1210                1215

Asp Ser Val Glu Leu Leu Leu Met Glu Glu
    1220                1225

<210> SEQ ID NO 47
<211> LENGTH: 1228
<212> TYPE: PRT
<213> ORGANISM: Bacillus thuringiensis

<400> SEQUENCE: 47

Met Thr Ser Asn Arg Lys Asn Glu Asn Glu Ile Ile Asn Ala Val Ser
1               5                   10                  15

```
Asn His Ser Ala Gln Met Asp Leu Leu Pro Asp Ala Arg Ile Glu Asp
             20                  25                  30

Ser Leu Cys Ile Ala Glu Gly Asn Ile Asp Pro Phe Val Ser Ala
         35                  40                  45

Ser Thr Val Gln Thr Gly Ile Asn Ile Ala Gly Arg Ile Leu Gly Val
     50                  55                  60

Leu Gly Val Pro Phe Ala Gly Gln Leu Ala Ser Phe Tyr Ser Phe Leu
 65                  70                  75                  80

Val Gly Glu Leu Trp Pro Arg Gly Arg Asp Gln Trp Glu Ile Phe Leu
                 85                  90                  95

Glu His Val Glu Gln Leu Ile Asn Gln Gln Ile Thr Glu Asn Ala Arg
                100                 105                 110

Asn Thr Ala Leu Ala Arg Leu Gln Gly Leu Gly Asp Ser Phe Arg Ala
            115                 120                 125

Tyr Gln Gln Ser Leu Glu Asp Trp Leu Glu Asn Arg Asp Asp Ala Arg
130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Arg
                180                 185                 190

Asp Ala Ser Leu Phe Gly Ser Glu Phe Gly Leu Thr Ser Gln Glu Ile
            195                 200                 205

Gln Arg Tyr Tyr Glu Arg Gln Val Glu Arg Thr Arg Asp Tyr Ser Asp
210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
            275                 280                 285

Asp Ala Ile Gly Ala Thr Gly Val Asn Met Ala Ser Met Asn Trp Tyr
290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
            325                 330                 335

Ser Ser Arg Trp Ser Asn Thr Arg His Met Thr Tyr Trp Arg Gly Arg
            340                 345                 350

Thr Ile Gln Ser Arg Pro Ile Gly Gly Gly Leu Asn Thr Ser Thr His
            355                 360                 365

Gly Ala Thr Asn Thr Ser Ile Asn Pro Val Thr Leu Arg Phe Ala Ser
            370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430
```

```
Pro Tyr Glu Ser Pro Gly Leu Gln Leu Lys Asp Ser Glu Thr Glu Leu
            435                 440                 445

Pro Pro Glu Thr Thr Glu Arg Pro Asn Tyr Glu Ser Tyr Ser His Arg
450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
            485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
            515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
            565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
            595                 600                 605

Gln Asp Ile Ile Arg Thr Ser Ile Gln Gly Leu Ser Gly Asn Gly Glu
            610                 615                 620

Val Tyr Ile Asp Lys Ile Glu Ile Ile Pro Val Thr Ala Thr Phe Glu
625                 630                 635                 640

Ala Glu Tyr Asp Leu Glu Arg Ala Gln Glu Ala Val Asn Ala Leu Phe
            645                 650                 655

Thr Asn Thr Asn Pro Arg Arg Leu Lys Thr Asp Val Thr Asp Tyr His
            660                 665                 670

Ile Asp Gln Val Ser Asn Leu Val Ala Cys Leu Ser Asp Glu Phe Cys
            675                 680                 685

Leu Asp Glu Lys Arg Glu Leu Leu Glu Lys Val Lys Tyr Ala Lys Arg
690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
            725                 730                 735

Ser Ile His Glu Gln Ser Glu His Gly Trp Trp Gly Ser Glu Asn Ile
            740                 745                 750

Thr Ile Gln Glu Gly Asn Asp Val Phe Lys Glu Asn Tyr Val Thr Leu
            755                 760                 765

Pro Gly Thr Phe Asn Glu Cys Tyr Pro Thr Tyr Leu Tyr Gln Lys Ile
770                 775                 780

Gly Glu Ser Glu Leu Lys Ala Tyr Thr Arg Tyr Gln Leu Arg Gly Tyr
785                 790                 795                 800

Ile Glu Asp Ser Gln Asp Leu Glu Ile Tyr Leu Ile Arg Tyr Asn Ala
            805                 810                 815

Lys His Glu Thr Leu Asp Val Pro Gly Thr Glu Ser Leu Trp Pro Leu
            820                 825                 830

Ser Val Glu Ser Pro Ile Gly Arg Cys Gly Glu Pro Asn Arg Cys Ala
            835                 840                 845

Pro His Phe Glu Trp Asn Pro Asp Leu Asp Cys Ser Cys Arg Asp Gly
```

```
            850                 855                 860
Glu Lys Cys Ala His His Ser His His Phe Ser Leu Asp Ile Asp Val
865                 870                 875                 880

Gly Cys Thr Asp Leu His Glu Asn Leu Gly Val Trp Val Val Phe Lys
                885                 890                 895

Ile Lys Thr Gln Glu Gly His Ala Arg Leu Gly Asn Leu Glu Phe Ile
            900                 905                 910

Glu Glu Lys Pro Leu Leu Gly Glu Ala Leu Ser Arg Val Lys Arg Ala
        915                 920                 925

Glu Lys Lys Trp Arg Asp Lys Arg Glu Lys Leu Gln Leu Glu Thr Lys
    930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
                965                 970                 975

Ala Ala Asp Lys Leu Val His Arg Ile Arg Glu Ala Tyr Leu Ser Glu
            980                 985                 990

Leu Pro Val Ile Pro Gly Val Asn Ala Glu Ile Phe Glu Glu Leu Glu
        995                 1000                1005

Gly His Ile Ile Thr Ala Ile Ser Leu Tyr Asp Ala Arg Asn Val
    1010                1015                1020

Val Lys Asn Gly Asp Phe Asn Asn Gly Leu Thr Cys Trp Asn Val
    1025                1030                1035

Lys Gly His Val Asp Val Gln Gln Ser His His Arg Ser Asp Leu
    1040                1045                1050

Val Ile Pro Glu Trp Glu Ala Glu Val Ser Gln Ala Val Arg Val
    1055                1060                1065

Cys Pro Gly Cys Gly Tyr Ile Leu Arg Val Thr Ala Tyr Lys Glu
    1070                1075                1080

Gly Tyr Gly Glu Gly Cys Val Thr Ile His Glu Ile Glu Asn Asn
    1085                1090                1095

Thr Asp Glu Leu Lys Phe Lys Asn Arg Glu Glu Glu Val Tyr
    1100                1105                1110

Pro Thr Asp Thr Gly Thr Cys Asn Asp Tyr Thr Ala His Gln Gly
    1115                1120                1125

Thr Ala Gly Cys Ala Asp Ala Cys Asn Ser Arg Asn Ala Gly Tyr
    1130                1135                1140

Glu Asp Ala Tyr Glu Val Asp Thr Thr Ala Ser Val Asn Tyr Lys
    1145                1150                1155

Pro Thr Tyr Glu Glu Glu Thr Tyr Thr Asp Val Arg Arg Asp Asn
    1160                1165                1170

His Cys Glu Tyr Asp Arg Gly Tyr Val Asn Tyr Pro Pro Val Pro
    1175                1180                1185

Ala Gly Tyr Val Thr Lys Glu Leu Glu Tyr Phe Pro Glu Thr Asp
    1190                1195                1200

Thr Val Trp Ile Glu Ile Gly Glu Thr Glu Gly Lys Phe Ile Val
    1205                1210                1215

Asp Ser Val Glu Leu Leu Leu Met Glu Glu
    1220                1225

<210> SEQ ID NO 48
<211> LENGTH: 1228
<212> TYPE: PRT
<213> ORGANISM: Bacillus thuringiensis
```

<400> SEQUENCE: 48

```
Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65              70                  75                  80

Val Gly Glu Leu Trp Pro Arg Gly Arg Asp Gln Trp Glu Ile Phe Leu
            85                  90                  95

Glu His Val Glu Gln Leu Ile Asn Gln Gln Ile Thr Glu Asn Ala Arg
        100                 105                 110

Asn Thr Ala Leu Ala Arg Leu Gln Gly Leu Gly Asp Ser Phe Arg Ala
    115                 120                 125

Tyr Gln Gln Ser Leu Glu Asp Trp Leu Glu Asn Arg Asp Asp Ala Arg
130                 135                 140

Thr Arg Ser Val Leu His Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
        355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
```

-continued

```
                405                 410                 415
Thr Asn Pro Gln Asn Ile Ser Asp Arg Gly Thr Ala Asn Tyr Ser Gln
            420                 425                 430
Pro Tyr Glu Ser Pro Gly Leu Gln Leu Lys Asp Ser Glu Thr Glu Leu
            435                 440                 445
Pro Pro Glu Thr Thr Glu Arg Pro Asn Tyr Glu Ser Tyr Ser His Arg
450                 455                 460
Leu Ser His Ile Gly Ile Ile Leu Gln Ser Arg Val Asn Val Pro Val
465                 470                 475                 480
Tyr Ser Trp Thr His Arg Ser Ala Asp Arg Thr Asn Thr Ile Gly Pro
            485                 490                 495
Asn Arg Ile Thr Gln Ile Pro Met Val Lys Ala Ser Glu Leu Pro Gln
            500                 505                 510
Gly Thr Thr Val Val Arg Gly Pro Gly Phe Thr Gly Gly Asp Ile Leu
            515                 520                 525
Arg Arg Thr Asn Thr Gly Gly Phe Gly Pro Ile Arg Val Thr Val Asn
            530                 535                 540
Gly Pro Leu Thr Gln Arg Tyr Arg Ile Gly Phe Arg Tyr Ala Ser Thr
545                 550                 555                 560
Val Asp Phe Asp Phe Val Ser Arg Gly Thr Thr Val Asn Asn
                565                 570                 575
Phe Arg Phe Leu Arg Thr Met Asn Ser Gly Asp Glu Leu Lys Tyr Gly
            580                 585                 590
Asn Phe Val Arg Arg Ala Phe Thr Thr Pro Phe Thr Phe Thr Gln Ile
            595                 600                 605
Gln Asp Ile Ile Arg Thr Ser Ile Gln Gly Leu Ser Gly Asn Gly Glu
            610                 615                 620
Val Tyr Ile Asp Lys Ile Glu Ile Ile Pro Val Thr Ala Thr Phe Glu
625                 630                 635                 640
Ala Glu Tyr Asp Leu Glu Arg Ala Gln Glu Ala Val Asn Ala Leu Phe
            645                 650                 655
Thr Asn Thr Asn Pro Arg Arg Leu Lys Thr Asp Val Thr Asp Tyr His
            660                 665                 670
Ile Asp Gln Val Ser Asn Leu Val Ala Cys Leu Ser Asp Glu Phe Cys
            675                 680                 685
Leu Asp Glu Lys Arg Glu Leu Leu Glu Lys Val Lys Tyr Ala Lys Arg
            690                 695                 700
Leu Ser Asp Glu Arg Asn Leu Leu Gln Asp Pro Asn Phe Thr Ser Ile
705                 710                 715                 720
Asn Lys Gln Pro Asp Phe Ile Ser Thr Asn Glu Gln Ser Asn Phe Thr
            725                 730                 735
Ser Ile His Glu Gln Ser Glu His Gly Trp Trp Gly Ser Glu Asn Ile
            740                 745                 750
Thr Ile Gln Glu Gly Asn Asp Val Phe Lys Glu Asn Tyr Val Thr Leu
            755                 760                 765
Pro Gly Thr Phe Asn Glu Cys Tyr Pro Thr Tyr Leu Tyr Gln Lys Ile
            770                 775                 780
Gly Glu Ser Glu Leu Lys Ala Tyr Thr Arg Tyr Gln Leu Arg Gly Tyr
785                 790                 795                 800
Ile Glu Asp Ser Gln Asp Leu Glu Ile Tyr Leu Ile Arg Tyr Asn Ala
            805                 810                 815
Lys His Glu Thr Leu Asp Val Pro Gly Thr Glu Ser Leu Trp Pro Leu
            820                 825                 830
```

-continued

```
Ser Val Glu Ser Pro Ile Gly Arg Cys Gly Glu Pro Asn Arg Cys Ala
            835                 840                 845
Pro His Phe Glu Trp Asn Pro Asp Leu Asp Cys Ser Cys Arg Asp Gly
850                 855                 860
Glu Lys Cys Ala His His Ser His His Phe Ser Leu Asp Ile Asp Val
865                 870                 875                 880
Gly Cys Thr Asp Leu His Glu Asn Leu Gly Val Trp Val Val Phe Lys
                885                 890                 895
Ile Lys Thr Gln Glu Gly His Ala Arg Leu Gly Asn Leu Glu Phe Ile
            900                 905                 910
Glu Glu Lys Pro Leu Leu Gly Ala Leu Ser Arg Val Lys Arg Ala
            915                 920                 925
Glu Lys Lys Trp Arg Asp Lys Arg Glu Lys Leu Gln Leu Glu Thr Lys
            930                 935                 940
Arg Val Tyr Thr Glu Ala Lys Glu Ala Val Asp Ala Leu Phe Val Asp
945                 950                 955                 960
Ser Gln Tyr Asp Arg Leu Gln Ala Asp Thr Asn Ile Gly Met Ile His
                965                 970                 975
Ala Ala Asp Lys Leu Val His Arg Ile Arg Glu Ala Tyr Leu Ser Glu
            980                 985                 990
Leu Pro Val Ile Pro Gly Val Asn Ala Glu Ile Phe Glu Glu Leu Glu
            995                 1000                1005
Gly His Ile Ile Thr Ala Ile Ser Leu Tyr Asp Ala Arg Asn Val
    1010                1015                1020
Val Lys Asn Gly Asp Phe Asn Asn Gly Leu Thr Cys Trp Asn Val
    1025                1030                1035
Lys Gly His Val Asp Val Gln Gln Ser His His Arg Ser Asp Leu
    1040                1045                1050
Val Ile Pro Glu Trp Glu Ala Glu Val Ser Gln Ala Val Arg Val
    1055                1060                1065
Cys Pro Gly Cys Gly Tyr Ile Leu Arg Val Thr Ala Tyr Lys Glu
    1070                1075                1080
Gly Tyr Gly Glu Gly Cys Val Thr Ile His Glu Ile Glu Asn Asn
    1085                1090                1095
Thr Asp Glu Leu Lys Phe Lys Asn Arg Glu Glu Glu Val Tyr
    1100                1105                1110
Pro Thr Asp Thr Gly Thr Cys Asn Asp Tyr Thr Ala His Gln Gly
    1115                1120                1125
Thr Ala Gly Cys Ala Asp Ala Cys Asn Ser Arg Asn Ala Gly Tyr
    1130                1135                1140
Glu Asp Ala Tyr Glu Val Asp Thr Thr Ala Ser Val Asn Tyr Lys
    1145                1150                1155
Pro Thr Tyr Glu Glu Glu Thr Tyr Thr Asp Val Arg Arg Asp Asn
    1160                1165                1170
His Cys Glu Tyr Asp Arg Gly Tyr Val Asn Tyr Pro Pro Val Pro
    1175                1180                1185
Ala Gly Tyr Val Thr Lys Glu Leu Glu Tyr Phe Pro Glu Thr Asp
    1190                1195                1200
Thr Val Trp Ile Glu Ile Gly Glu Thr Glu Gly Lys Phe Ile Val
    1205                1210                1215
Asp Ser Val Glu Leu Leu Leu Met Glu Glu
    1220                1225
```

-continued

```
<210> SEQ ID NO 49
<211> LENGTH: 1228
<212> TYPE: PRT
<213> ORGANISM: Bacillus thuringiensis

<400> SEQUENCE

```
Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
            420                 425                 430

Pro Tyr Glu Ser Pro Gly Leu Gln Leu Lys Asp Ser Glu Thr Glu Leu
            435                 440                 445

Pro Pro Glu Thr Thr Glu Arg Pro Asn Tyr Glu Ser Tyr Ser His Arg
        450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
            515                 520                 525

Arg Arg Thr Asn Thr Gly Gly Phe Gly Pro Ile Arg Val Thr Val Asn
530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
            595                 600                 605

Gln Asp Ile Ile Arg Thr Ser Ile Gln Gly Leu Ser Gly Asn Gly Glu
    610                 615                 620

Val Tyr Ile Asp Lys Ile Glu Ile Ile Pro Val Thr Ala Thr Phe Glu
625                 630                 635                 640

Ala Glu Tyr Asp Leu Glu Arg Ala Gln Glu Ala Val Asn Ala Leu Phe
                645                 650                 655

Thr Asn Thr Asn Pro Arg Arg Leu Lys Thr Asp Val Thr Asp Tyr His
            660                 665                 670

Ile Asp Gln Val Ser Asn Leu Val Ala Cys Leu Ser Asp Glu Phe Cys
            675                 680                 685

Leu Asp Glu Lys Arg Glu Leu Leu Glu Lys Val Lys Tyr Ala Lys Arg
            690                 695                 700

Leu Ser Asp Glu Arg Asn Leu Leu Gln Asp Pro Asn Phe Thr Ser Ile
705                 710                 715                 720

Asn Lys Gln Pro Asp Phe Ile Ser Thr Asn Glu Gln Ser Asn Phe Thr
                725                 730                 735

Ser Ile His Glu Gln Ser Glu His Gly Trp Trp Gly Ser Glu Asn Ile
            740                 745                 750

Thr Ile Gln Glu Gly Asn Asp Val Phe Lys Glu Asn Tyr Val Thr Leu
            755                 760                 765

Pro Gly Thr Phe Asn Glu Cys Tyr Pro Thr Tyr Leu Tyr Gln Lys Ile
            770                 775                 780

Gly Glu Ser Glu Leu Lys Ala Tyr Thr Arg Tyr Gln Leu Arg Gly Tyr
785                 790                 795                 800
```

```
Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
        820                 825                 830

Ser Val Glu Ser Pro Ile Gly Arg Cys Gly Glu Pro Asn Arg Cys Ala
        835                 840                 845

Pro His Phe Glu Trp Asn Pro Asp Leu Asp Cys Ser Cys Arg Asp Gly
850                 855                 860

Glu Lys Cys Ala His His Ser His His Phe Ser Leu Asp Ile Asp Val
865                 870                 875                 880

Gly Cys Thr Asp Leu His Glu Asn Leu Gly Val Trp Val Val Phe Lys
            885                 890                 895

Ile Lys Thr Gln Glu Gly His Ala Arg Leu Gly Asn Leu Glu Phe Ile
            900                 905                 910

Glu Glu Lys Pro Leu Leu Gly Glu Ala Leu Ser Arg Val Lys Arg Ala
            915                 920                 925

Glu Lys Lys Trp Arg Asp Lys Arg Glu Lys Leu Gln Leu Glu Thr Lys
        930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
                965                 970                 975

Ala Ala Asp Lys Leu Val His Arg Ile Arg Glu Ala Tyr Leu Ser Glu
                980                 985                 990

Leu Pro Val Ile Pro Gly Val Asn Ala Glu Ile Phe Glu Glu Leu Glu
            995                 1000                1005

Gly His Ile Ile Thr Ala Ile Ser Leu Tyr Asp Ala Arg Asn Val
        1010                1015                1020

Val Lys Asn Gly Asp Phe Asn Asn Gly Leu Thr Cys Trp Asn Val
        1025                1030                1035

Lys Gly His Val Asp Val Gln Gln Ser His His Arg Ser Asp Leu
    1040                1045                1050

Val Ile Pro Glu Trp Glu Ala Glu Val Ser Gln Ala Val Arg Val
    1055                1060                1065

Cys Pro Gly Cys Gly Tyr Ile Leu Arg Val Thr Ala Tyr Lys Glu
    1070                1075                1080

Gly Tyr Gly Glu Gly Cys Val Thr Ile His Glu Ile Glu Asn Asn
    1085                1090                1095

Thr Asp Glu Leu Lys Phe Lys Asn Arg Glu Glu Glu Val Tyr
    1100                1105                1110

Pro Thr Asp Thr Gly Thr Cys Asn Asp Tyr Thr Ala His Gln Gly
    1115                1120                1125

Thr Ala Gly Cys Ala Asp Ala Cys Asn Ser Arg Asn Ala Gly Tyr
    1130                1135                1140

Glu Asp Ala Tyr Glu Val Asp Thr Thr Ala Ser Val Asn Tyr Lys
    1145                1150                1155

Pro Thr Tyr Glu Glu Glu Thr Tyr Thr Asp Val Arg Arg Asp Asn
    1160                1165                1170

His Cys Glu Tyr Asp Arg Gly Tyr Val Asn Tyr Pro Pro Val Pro
    1175                1180                1185

Ala Gly Tyr Val Thr Lys Glu Leu Glu Tyr Phe Pro Glu Thr Asp
    1190                1195                1200

Thr Val Trp Ile Glu Ile Gly Glu Thr Glu Gly Lys Phe Ile Val
```

```
                1205                1210                1215
Asp Ser Val Glu Leu Leu Leu Met Glu Glu
           1220                1225

<210> SEQ ID NO 50
<211> LENGTH: 1228
<212> TYPE: PRT
<213> ORGANISM: Bacillus thuringiensis

<400> SEQUENCE: 50

Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Gly Leu Thr
                245                 250                 255

Leu Gly Val Leu Gly Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350
```

```
Thr Ile Gln Ser Arg Pro Ile Gly Gly Leu Asn Thr Ser Thr His
            355                 360                 365
Gly Ala Thr Asn Thr Ser Ile Asn Pro Val Thr Leu Arg Phe Ala Ser
    370                 375                 380
Arg Asp Val Tyr Arg Thr Glu Ser Tyr Ala Gly Val Leu Leu Trp Gly
385                 390                 395                 400
Ile Tyr Leu Glu Pro Ile His Gly Val Pro Thr Val Arg Phe Asn Phe
                405                 410                 415
Thr Asn Pro Gln Asn Ile Ser Asp Arg Gly Thr Ala Asn Tyr Ser Gln
            420                 425                 430
Pro Tyr Glu Ser Pro Gly Leu Gln Leu Lys Asp Ser Glu Thr Glu Leu
        435                 440                 445
Pro Pro Glu Thr Thr Glu Arg Pro Asn Tyr Glu Ser Tyr Ser His Arg
    450                 455                 460
Leu Ser His Ile Gly Ile Ile Leu Gln Ser Arg Val Asn Val Pro Val
465                 470                 475                 480
Tyr Ser Trp Thr His Arg Ser Ala Asp Arg Thr Asn Thr Ile Gly Pro
                485                 490                 495
Asn Arg Ile Thr Gln Ile Pro Met Val Lys Ala Ser Glu Leu Pro Gln
            500                 505                 510
Gly Thr Thr Val Val Arg Gly Pro Gly Phe Thr Gly Gly Asp Ile Leu
        515                 520                 525
Arg Arg Thr Asn Thr Gly Gly Phe Gly Pro Ile Arg Val Thr Val Asn
    530                 535                 540
Gly Pro Leu Thr Gln Arg Tyr Arg Ile Gly Phe Arg Tyr Ala Ser Thr
545                 550                 555                 560
Val Asp Phe Asp Phe Phe Ala Ser Arg Gly Gly Thr Thr Val Asn Asn
                565                 570                 575
Phe Arg Phe Leu Arg Thr Met Asn Ser Gly Asp Glu Leu Lys Tyr Gly
            580                 585                 590
Asn Phe Val Arg Arg Ala Phe Thr Thr Pro Phe Thr Phe Thr Gln Ile
        595                 600                 605
Gln Asn Ile Ile Arg Thr Ser Ile Gln Gly Leu Ser Gly Asn Gly Glu
    610                 615                 620
Val Tyr Ile Asp Lys Ile Glu Ile Ile Pro Val Thr Ala Thr Phe Glu
625                 630                 635                 640
Ala Glu Tyr Asp Leu Glu Arg Ala Gln Glu Ala Val Asn Ala Leu Phe
                645                 650                 655
Thr Asn Thr Asn Pro Arg Arg Leu Lys Thr Asp Val Thr Asp Tyr His
            660                 665                 670
Ile Asp Gln Val Ser Asn Leu Val Ala Cys Leu Ser Asp Glu Phe Cys
        675                 680                 685
Leu Asp Glu Lys Arg Glu Leu Leu Glu Lys Val Lys Tyr Ala Lys Arg
    690                 695                 700
Leu Ser Asp Glu Arg Asn Leu Leu Gln Asp Pro Asn Phe Thr Ser Ile
705                 710                 715                 720
Asn Lys Gln Pro Asp Phe Ile Ser Thr Asn Glu Gln Ser Asn Phe Thr
                725                 730                 735
Ser Ile His Glu Gln Ser Glu His Gly Trp Trp Gly Ser Glu Asn Ile
            740                 745                 750
Thr Ile Gln Glu Gly Asn Asp Val Ser Lys Glu Asn Tyr Val Thr Leu
        755                 760                 765
Pro Gly Thr Phe Asn Glu Cys Tyr Pro Thr Tyr Leu Tyr Gln Lys Ile
```

```
            770                 775                 780
Gly Glu Ser Glu Leu Lys Ala Tyr Thr Arg Tyr Gln Leu Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Leu Asp Val Pro Gly Thr Glu Ser Leu Trp Pro Leu
                820                 825                 830

Ser Val Glu Ser Pro Ile Gly Arg Cys Gly Glu Pro Asn Arg Cys Ala
                835                 840                 845

Pro His Phe Glu Trp Asn Pro Asp Leu Asp Cys Ser Cys Arg Asp Gly
                850                 855                 860

Glu Lys Cys Ala His His Ser His His Phe Ser Leu Asp Ile Asp Val
865                 870                 875                 880

Gly Cys Thr Asp Leu His Glu Asn Leu Gly Val Trp Val Phe Lys
                885                 890                 895

Ile Lys Thr Gln Glu Gly His Ala Arg Leu Gly Asn Leu Glu Phe Ile
                900                 905                 910

Glu Glu Lys Pro Leu Leu Gly Glu Ala Leu Ser Arg Val Lys Arg Ala
                915                 920                 925

Glu Lys Lys Trp Arg Asp Lys Arg Glu Lys Leu Gln Leu Glu Thr Lys
                930                 935                 940

Arg Val Tyr Thr Glu Ala Lys Glu Ala Val Asp Ala Leu Phe Val Asp
945                 950                 955                 960

Ser Gln Tyr Asp Arg Leu Gln Ala Asp Thr Asn Ile Gly Met Ile His
                965                 970                 975

Ala Ala Asp Lys Leu Val His Arg Ile Arg Glu Ala Tyr Leu Ser Glu
                980                 985                 990

Leu Pro Val Ile Pro Gly Val Asn Ala Glu Ile Phe Glu Glu Leu Glu
                995                 1000                1005

Gly His Ile Ile Thr Ala Ile Ser Leu Tyr Asp Ala Arg Asn Val
        1010            1015                1020

Val Lys Asn Gly Asp Phe Asn Asn Gly Leu Thr Cys Trp Asn Val
        1025            1030                1035

Lys Gly His Val Asp Val Gln Gln Ser His His Arg Ser Asp Leu
        1040            1045                1050

Val Ile Pro Glu Trp Glu Ala Glu Val Ser Gln Ala Val Arg Val
        1055            1060                1065

Cys Pro Gly Cys Gly Tyr Ile Leu Ser Val Thr Ala Tyr Lys Glu
        1070            1075                1080

Gly Tyr Gly Glu Gly Cys Val Thr Ile His Glu Ile Glu Asn Asn
        1085            1090                1095

Thr Asp Glu Leu Lys Phe Lys Asn Arg Glu Glu Glu Val Tyr
        1100            1105                1110

Pro Thr Asp Thr Gly Thr Cys Asn Asp Tyr Thr Ala His Gln Gly
        1115            1120                1125

Thr Ala Gly Cys Ala Asp Ala Cys Asn Ser Arg Asn Ala Gly Tyr
        1130            1135                1140

Glu Asp Ala Tyr Glu Val Asp Thr Thr Ala Ser Val Asn Tyr Lys
        1145            1150                1155

Pro Thr Tyr Glu Glu Glu Tyr Thr Asp Val Arg Arg Asp Asn
        1160            1165                1170

His Cys Glu Tyr Asp Arg Gly Tyr Val Asn Tyr Pro Pro Val Pro
        1175            1180                1185
```

```
Ala Gly Tyr Val Thr Lys Glu Leu Glu Tyr Phe Pro Glu Thr Asp
    1190                1195                1200

Thr Val Trp Ile Glu Ile Gly Glu Thr Glu Gly Lys Phe Met Val
    1205                1210                1215

Asp Ser Val Glu Leu Leu Leu Met Glu Glu
    1220                1225

<210> SEQ ID NO 51
<211> LENGTH: 1155
<212> TYPE: PRT
<213> ORGANISM: Bacillus thuringiensis

<400> SEQUENCE: 51

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335
```

```
Leu Tyr Gly Thr Met Gly Asn Ala Ala Pro Gln Gln Arg Ile Val Ala
            340                 345                 350
Gln Leu Gly Gln Gly Val Tyr Arg Thr Leu Ser Ser Thr Leu Tyr Arg
        355                 360                 365
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Ser Val Ser Ile Ile
        435                 440                 445
Arg Ala Pro Met Phe Ser Trp Ile His Arg Ser Ala Glu Phe Asn Asn
    450                 455                 460
Ile Ile Pro Ser Ser Gln Ile Thr Gln Ile Pro Leu Thr Lys Ser Thr
465                 470                 475                 480
Asn Leu Gly Ser Gly Thr Ser Val Val Lys Gly Pro Gly Phe Thr Gly
                485                 490                 495
Gly Asp Ile Leu Arg Arg Thr Ser Pro Gly Gln Ile Ser Thr Leu Arg
            500                 505                 510
Val Asn Ile Thr Ala Pro Leu Ser Gln Arg Tyr Arg Val Arg Ile Arg
        515                 520                 525
Tyr Ala Ser Thr Thr Asn Leu Gln Phe His Thr Ser Ile Asp Gly Arg
    530                 535                 540
Pro Ile Asn Gln Gly Asn Phe Ser Ala Thr Met Ser Ser Gly Ser Asn
545                 550                 555                 560
Leu Gln Ser Gly Ser Phe Arg Thr Val Gly Phe Thr Thr Pro Phe Asn
                565                 570                 575
Phe Ser Asn Gly Ser Ser Val Phe Thr Leu Ser Ala His Val Phe Asn
            580                 585                 590
Ser Gly Asn Glu Val Tyr Ile Asp Arg Ile Glu Phe Val Pro Ala Glu
        595                 600                 605
Val Thr Phe Glu Ala Glu Tyr Asp Leu Glu Arg Ala Gln Lys Ala Val
    610                 615                 620
Asn Glu Leu Phe Thr Ser Ser Asn Gln Ile Gly Leu Lys Thr Asp Val
625                 630                 635                 640
Thr Asp Tyr His Ile Asp Gln Val Ser Asn Leu Val Glu Cys Leu Ser
                645                 650                 655
Asp Glu Phe Cys Leu Asp Glu Lys Lys Glu Leu Ser Glu Lys Val Lys
            660                 665                 670
His Ala Lys Arg Leu Ser Asp Glu Arg Asn Leu Leu Gln Asp Pro Asn
        675                 680                 685
Phe Arg Gly Ile Asn Arg Gln Leu Asp Arg Gly Trp Arg Gly Ser Thr
    690                 695                 700
Asp Ile Thr Ile Gln Gly Gly Asp Asp Val Phe Lys Gly Asn Tyr Val
705                 710                 715                 720
Thr Leu Leu Gly Thr Phe Asp Glu Cys Tyr Pro Thr Tyr Leu Tyr Gln
                725                 730                 735
Lys Ile Asp Glu Ser Lys Leu Lys Ala Tyr Thr Arg Tyr Gln Leu Arg
            740                 745                 750
```

-continued

```
Gly Tyr Ile Glu Asp Ser Gln Asp Leu Glu Ile Tyr Leu Ile Arg Tyr
            755                 760                 765
Asn Ala Lys His Glu Thr Val Asn Val Pro Gly Thr Gly Ser Leu Trp
        770                 775                 780
Pro Leu Ser Ala Pro Ser Pro Ile Gly Lys Cys Ala His His Ser His
785                 790                 795                 800
His Phe Ser Leu Asp Ile Asp Val Gly Cys Thr Asp Leu Asn Glu Asp
                805                 810                 815
Leu Gly Val Trp Val Ile Phe Lys Ile Lys Thr Gln Asp Gly His Ala
            820                 825                 830
Arg Leu Gly Asn Leu Glu Phe Leu Glu Glu Lys Pro Leu Val Gly Glu
        835                 840                 845
Ala Leu Ala Arg Val Lys Arg Ala Glu Lys Lys Trp Arg Asp Lys Arg
850                 855                 860
Glu Lys Leu Glu Trp Glu Thr Asn Ile Val Tyr Lys Glu Ala Lys Glu
865                 870                 875                 880
Ser Val Asp Ala Leu Phe Val Asn Ser Gln Tyr Asp Arg Leu Gln Ala
                885                 890                 895
Asp Thr Asn Ile Ala Met Ile His Ala Ala Asp Lys Arg Val His Ser
            900                 905                 910
Ile Arg Glu Ala Tyr Leu Pro Glu Leu Ser Val Ile Pro Gly Val Asn
        915                 920                 925
Ala Ala Ile Phe Glu Glu Leu Glu Gly Arg Ile Phe Thr Ala Phe Ser
930                 935                 940
Leu Tyr Asp Ala Arg Asn Val Ile Lys Asn Gly Asp Phe Asn Asn Gly
945                 950                 955                 960
Leu Ser Cys Trp Asn Val Lys Gly His Val Asp Val Glu Glu Gln Asn
                965                 970                 975
Asn His Arg Ser Val Leu Val Val Pro Glu Trp Glu Ala Glu Val Ser
            980                 985                 990
Gln Glu Val Arg Val Cys Pro Gly Arg Gly Tyr Ile Leu Arg Val Thr
        995                 1000                1005
Ala Tyr Lys Glu Gly Tyr Gly Glu Gly Cys Val Thr Ile His Glu
        1010                1015                1020
Ile Glu Asn Asn Thr Asp Glu Leu Lys Phe Ser Asn Cys Val Glu
        1025                1030                1035
Glu Glu Val Tyr Pro Asn Asn Thr Val Thr Cys Asn Asp Tyr Thr
        1040                1045                1050
Ala Thr Gln Glu Glu Tyr Glu Gly Thr Tyr Thr Ser Arg Asn Arg
        1055                1060                1065
Gly Tyr Asp Gly Ala Tyr Glu Ser Asn Ser Ser Val Pro Ala Asp
        1070                1075                1080
Tyr Ala Ser Ala Tyr Glu Glu Lys Ala Tyr Thr Asp Gly Arg Arg
        1085                1090                1095
Asp Asn Pro Cys Glu Ser Asn Arg Gly Tyr Gly Asp Tyr Thr Pro
        1100                1105                1110
Leu Pro Ala Gly Tyr Val Thr Lys Glu Leu Glu Tyr Phe Pro Glu
        1115                1120                1125
Thr Asp Lys Val Trp Ile Glu Ile Gly Glu Thr Glu Gly Thr Phe
        1130                1135                1140
Ile Val Asp Ser Val Glu Leu Leu Leu Met Glu Glu
        1145                1150                1155
```

The invention claimed is:

1. A nucleic acid molecule comprising a nucleotide sequence that encodes an engineered Cry1Ba (eCry1Ba) insecticidal protein comprising a mutation at a position corresponding to amino acids 2 and 150; or amino acids 2, 150 and 178; or amino acids 2, 150 and 189; or amino acids 2, 150 and 199, of SEQ ID NO: 5, wherein the amino acid corresponding to position 2 is any amino acid and (a) the amino acid corresponding to position 150 is Lys; or (b) the amino acid corresponding to position 150 is Lys and the amino acid corresponding to position 178 is Ser; or (c) the amino acid corresponding to position 150 is Lys and the amino acid corresponding to position 189 is Ser; or (d) the amino acid corresponding to position 150 is Lys and the amino acid corresponding to position 199 is Lys, and wherein said protein has improved solubility or insecticidal activity against at least European corn borer (*Ostrinia nubilalis*) when compared to a native or wild-type Cry1Ba protein, and wherein optionally the nucleotide sequence is optimized for expression in a transgenic host cell.

2. The nucleic acid molecule of claim 1, wherein the protein comprises an amino acid sequence of SEQ ID NO: 7, SEQ ID NO: 8, SEQ ID NO: 9 or SEQ ID NO: 10.

3. The nucleic acid molecule of claim 1, wherein the eCry1Ba protein has activity against lepidopteran or coleopteran insects.

4. The nucleic acid molecule of claim 3, wherein the lepidopteran insects are selected from the group consisting of European corn borer, southwestern corn borer, sugarcane borer, corn earworm, soybean looper and velvet bean caterpillar.

5. The nucleic acid molecule of claim 1, wherein the transgenic host cell is a bacterial cell or a plant cell.

6. The nucleic acid molecule of claim 5, wherein the plant cell is a maize plant cell.

7. The nucleic acid molecule of claim 6, wherein the nucleotide sequence comprises SEQ ID NO:13.

8. A chimeric gene comprising a heterologous promoter sequence operatively linked to the nucleic acid molecule of any one of claim 1 or 2-7.

9. The chimeric gene of claim 8, wherein the promoter is a plant-expressible promoter.

10. The chimeric gene of claim 9, wherein the plant-expressible promoter is selected from the group consisting of ubiquitin, cmp, corn TrpA, mtl, bacteriophage T3 gene 9 5' UTR, corn sucrose synthetase 1, corn alcohol dehydrogenase 1, corn light harvesting complex, corn heat shock protein, pea small subunit RuBP carboxylase, Ti plasmid opine synthase, Ti plaid nopaline synthase, petunia chalcone isomerase, bean glycine rich protein 1, Potato patatin, lectin, CaMV 35S, and the S-E9 small subunit RuBP carboxylase promoter.

11. A recombinant vector comprising the chimeric gene of claim 10.

12. The vector of claim 11, wherein the vector is a plasmid, cosmid, phagemid, artificial chromosome, phage or viral vector.

13. A transgenic non-human host cell comprising the chimeric gene of claim 8.

14. The transgenic host cell of claim 13 that is a bacterial cell or a plant cell.

15. The transgenic host call of claim 14, wherein the bacterial cell is an *E. coli, Bacillus thuringiensis, Bacillus subtilis, Bacillus megaterium; Bacillus cereus, Agrobacterium* or a *Pseudomonas* cell.

16. The transgenic host cell of claim 14, wherein the plant cell is a corn, wheat, oat rice, barley, sugar cane, turf grass, pasture grass, cotton, sunflower, cole crop vegetable, sugar beet, tobacco, or an oilseed rape cell.

17. A transgenic plant comprising the plant cell of claim 16.

18. The transgenic plant of claim 17, wherein the plant is a monocotyledonous plant or a dicotyledonous plant.

19. The transgenic plant of claim 18, wherein the monocotyledonous plant is selected from the group consisting of corn, wheat, oat, rice, barley, sugar cane, turf grass and a pasture grass.

20. The transgenic plant of claim 19, wherein said plant is a corn plant.

21. The transgenic plant of claim 18, wherein the dicotyledonous plant is selected from the group consisting of soybean, cotton, sunflower, cole crop vegetable, sugar beet, tobacco, and oilseed rape.

22. A progeny of any generation of the plant of claim 17, wherein the progeny comprises the nucleic acid molecule.

23. A seed from any generation of the transgenic plant of claim 17, wherein the seed comprises the nucleic acid molecule.

24. A method of making an insect-resistant transgenic plant, comprising introducing the nucleic acid molecule of claim 1 into a plant thereby producing a transgenic plant, wherein the nucleic acid molecule causes the expression of the engineered Cry1Ba protein in an amount that renders the transgenic plant insect resistant.

25. The method of claim 24, wherein the introducing step is carried out by transforming a plant with the nucleic acid molecule.

26. The method of claim 24, wherein the introducing step is carried out by crossing a transgenic plant comprising the nucleic acid molecule with a different plant.

27. The method of any one of claims 24-26, wherein the plant is maize.

28. The method of claim 24, wherein the plant is resistant to lepidopteran insects.

29. The method of claim 28, wherein the lepidopteran insects are selected from the group consisting of European corn borer, southwestern corn borer, sugarcane borer, corn earworm, soybean looper and velvet bean caterpillar.

* * * * *